US011426422B2

(12) United States Patent
Yu et al.

(10) Patent No.: US 11,426,422 B2
(45) Date of Patent: Aug. 30, 2022

(54) SHP2 INHIBITORS AND METHODS OF USE THEREOF

(71) Applicant: Research Development Foundation, Carson City, NV (US)

(72) Inventors: Hongtao Yu, Dallas, TX (US); Eunhee Choi, Dallas, TX (US)

(73) Assignee: Research Development Foundation, Carson City, NV (US)

(*) Notice: Subject to any disclaimer, the term of this patent is extended or adjusted under 35 U.S.C. 154(b) by 0 days.

(21) Appl. No.: 16/261,819

(22) Filed: Jan. 30, 2019

(65) Prior Publication Data

US 2019/0231805 A1 Aug. 1, 2019

Related U.S. Application Data

(60) Provisional application No. 62/623,958, filed on Jan. 30, 2018.

(51) Int. Cl.

| | | |
|---|---|---|
| *A61K 31/7088* | (2006.01) | |
| *A61K 9/127* | (2006.01) | |
| *A61K 9/51* | (2006.01) | |
| *A61P 5/50* | (2006.01) | |
| *C12N 15/113* | (2010.01) | |
| *A61P 35/00* | (2006.01) | |
| *A61P 3/10* | (2006.01) | |
| *A61K 31/497* | (2006.01) | |
| *A61K 31/506* | (2006.01) | |
| *A61K 31/53* | (2006.01) | |
| *A61K 45/06* | (2006.01) | |
| *A61K 47/20* | (2006.01) | |
| *A61K 47/26* | (2006.01) | |
| *A61K 47/38* | (2006.01) | |
| *A61K 9/00* | (2006.01) | |

(52) U.S. Cl.
CPC .......... *A61K 31/7088* (2013.01); *A61K 9/127* (2013.01); *A61K 9/51* (2013.01); *A61K 31/497* (2013.01); *A61K 31/506* (2013.01); *A61K 31/53* (2013.01); *A61P 3/10* (2018.01); *A61P 5/50* (2018.01); *A61P 35/00* (2018.01); *C12N 15/1138* (2013.01); *A61K 9/0053* (2013.01); *A61K 45/06* (2013.01); *A61K 47/20* (2013.01); *A61K 47/26* (2013.01); *A61K 47/38* (2013.01); *C12N 2310/313* (2013.01); *C12N 2310/322* (2013.01)

(58) Field of Classification Search
CPC .................................................. A61K 31/7088
USPC ....................................................... 514/255
See application file for complete search history.

(56) References Cited

U.S. PATENT DOCUMENTS

| 2004/0077574 A1 | 4/2004 | Klinghoffer et al. |
| 2017/0015680 A1 | 1/2017 | Chen et al. |

FOREIGN PATENT DOCUMENTS

| WO | WO 2016/203404 | 12/2016 |
| WO | WO 2017/156397 | 9/2017 |

OTHER PUBLICATIONS

OMIM-14670-Insulin Receptor-INCR (1966), pp. 1-27.*
Ardon et al., "Sequencing analysis of insulin receptor defects and detection of two novel mutations in INSR gene", *Mol. Genet. Metab. Rep.*, 1:71-84, 2014.
Choi et al., "Mitotic regulators and the SHP2-MAPK pathway promote IR endocytosis and feedback regulation of insulin signaling", *Nature Comm.*, 10:1473, 2019.
GenBank Accession No. D13540, retrieved on Mar. 29, 2019, https://www.ncbi.nlm.nih.gov/nuccore/D13540.1/), Dec. 18, 2007.
Giri et al., "Protein Tyrosine Phosphatase SHP2 Mediates Chronic Insulin-Induced Endothelial Inflammation", *Arterioscler. Thromb. Vasc. Biol.*, 32:1943-1950, 2012.
He et al., "Shp2 Controls Female Body Weight and Energy Balance by Integrating Leptin and Estrogen Signals", *Mol. Cell. Biol.*, 1867-1878, 2012.
International Search Report and Written Opinion issued in corresponding PCT Application No. PCT/US2019/015755, dated Jun. 10, 2019.
Luo et al., "The Tyrosine Phosphatase SHP2: A Key Molecule Linked both Type 2 Diabetes and Cancers?", *Med. Chem.*, 4(4):435-438, 2014.
Nagata et al., "Hepatic Src Homology Phosphatase 2 Regulates Energy Balance in Mice", *Endocrinology*, 153(7):3158-3169, 2012.
Ran et al., "Sticking It to Cancer with Molecular Glue for SHP2", *Cancer Cell*, 30:194-196, 2016.
Xu et al., "Role of protein tyrosine phosphatases in the modulation of insulin signaling and their implication in the pathogenesis of obesity-linked insulin resistance", *Rev. Endocr. Metab. Disord.*, 15(1):79-97, 2014.

* cited by examiner

*Primary Examiner* — Taofiq A Solola
(74) *Attorney, Agent, or Firm* — Parker Highlander PLLC

(57) ABSTRACT

Provided are methods for the treatment of insulin resistance and insulin receptor diseases with SHP2 inhibitors, such as allosteric inhibitors of SHP2 and RNAi or siRNA that target SHP2 expression. Compositions and methods for delivery of SHP2 inhibitors, such as liver-targeting liposomes or nanoparticles, are also provided.

25 Claims, 22 Drawing Sheets
(20 of 22 Drawing Sheet(s) Filed in Color)
Specification includes a Sequence Listing.

FIG. 1E

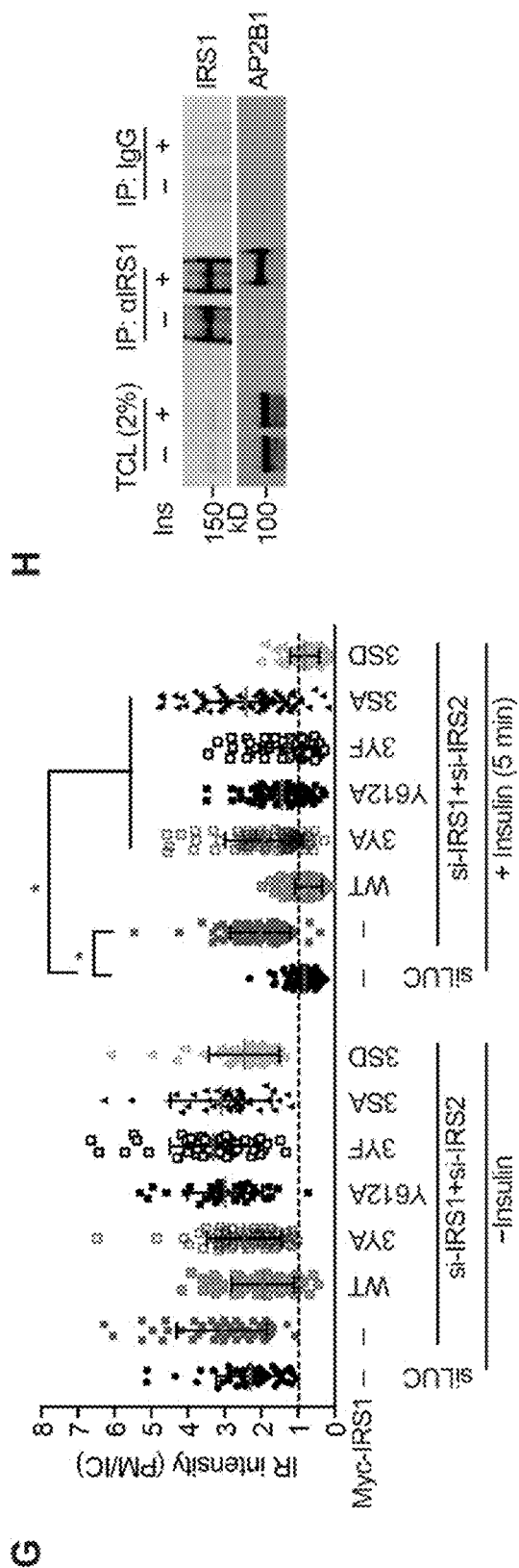
FIGS. 1G-H

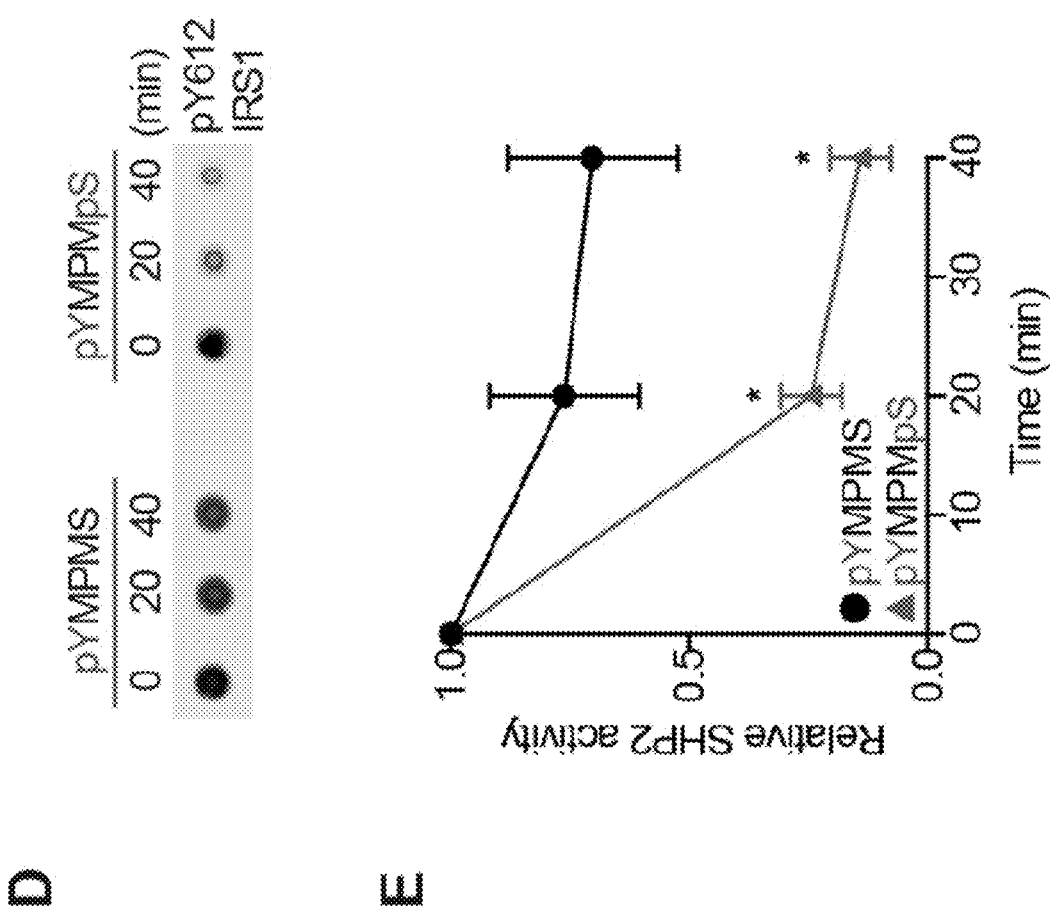
FIGS. 2D-E

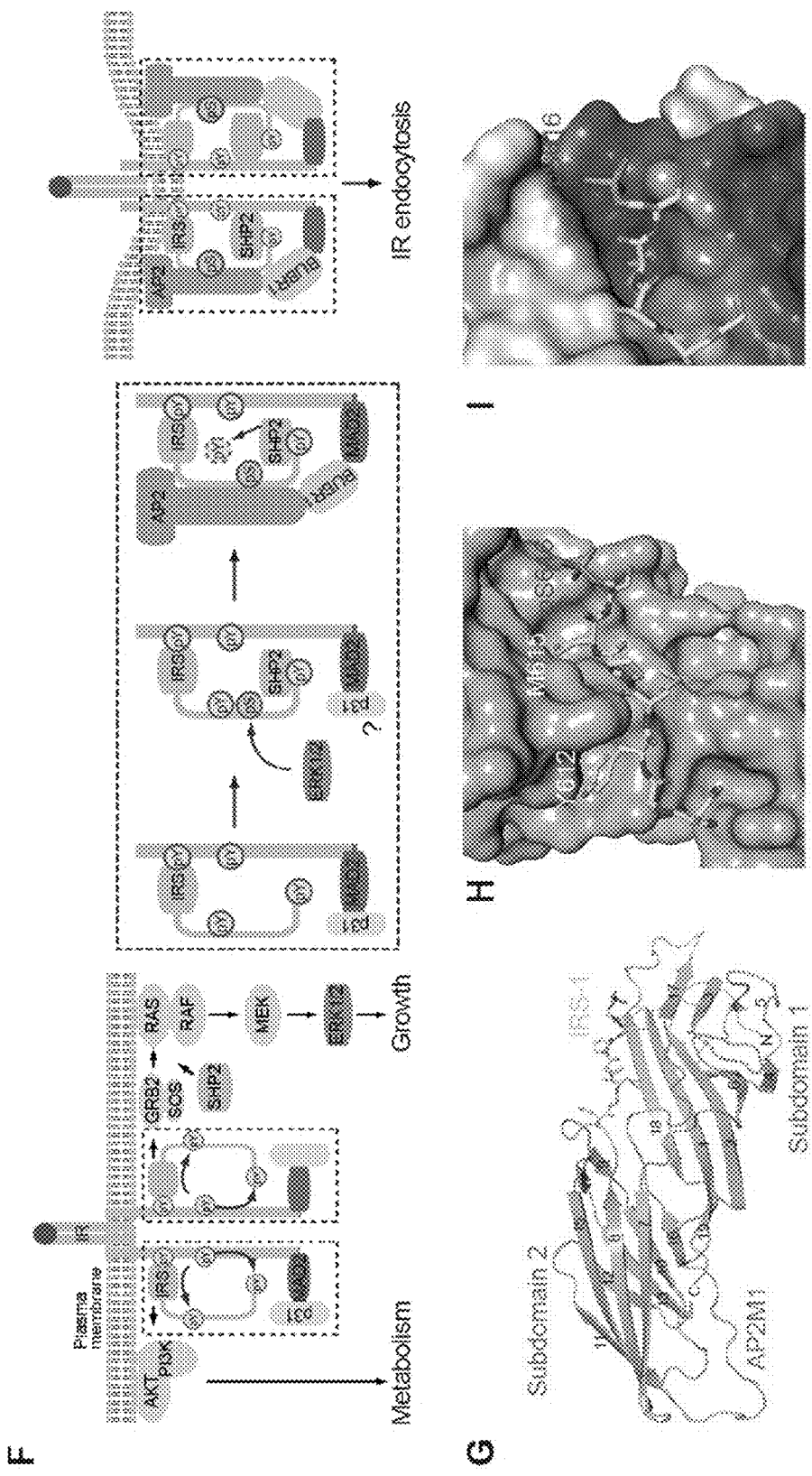
FIGS. 2F-I

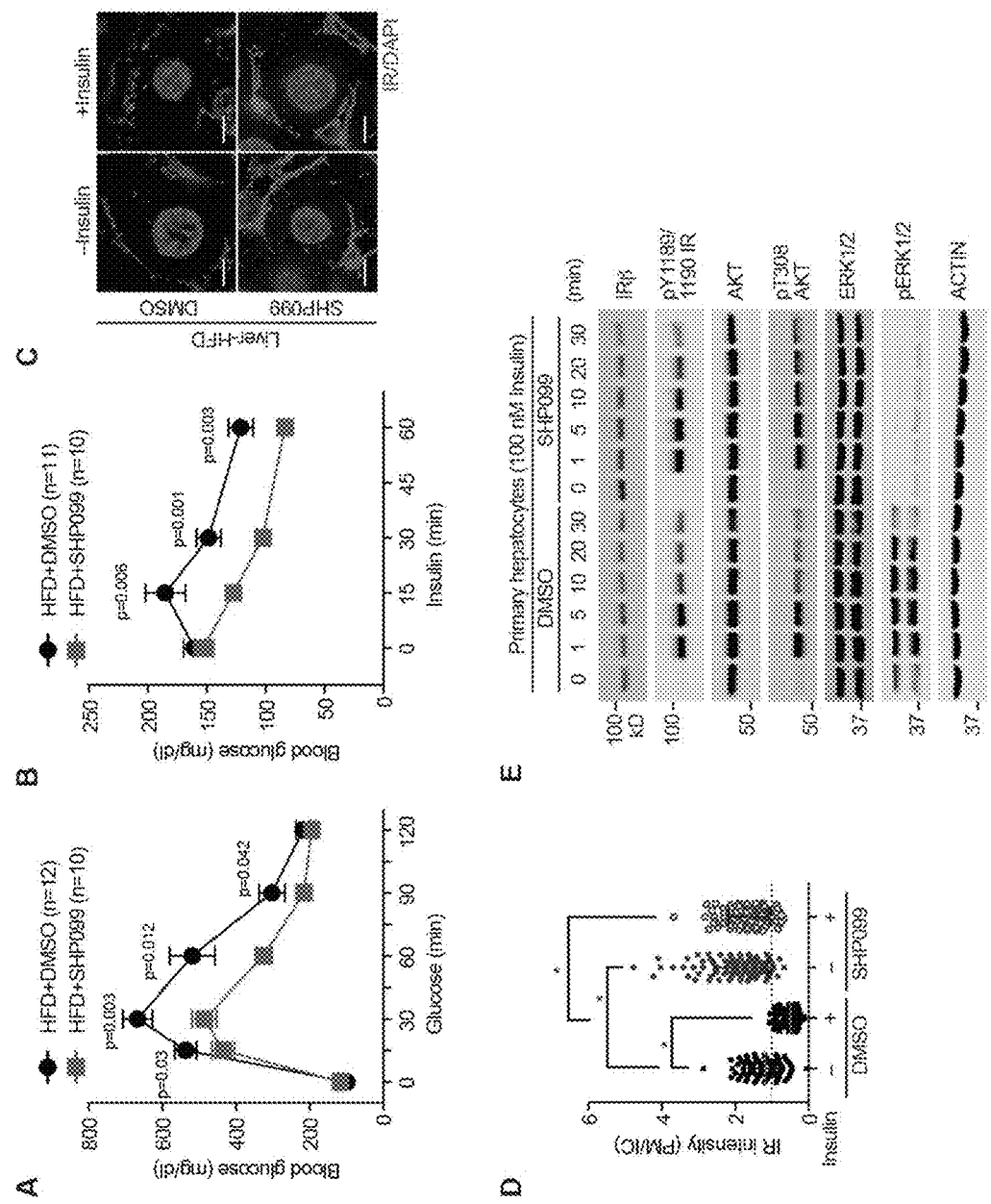
FIGS. 3A-E

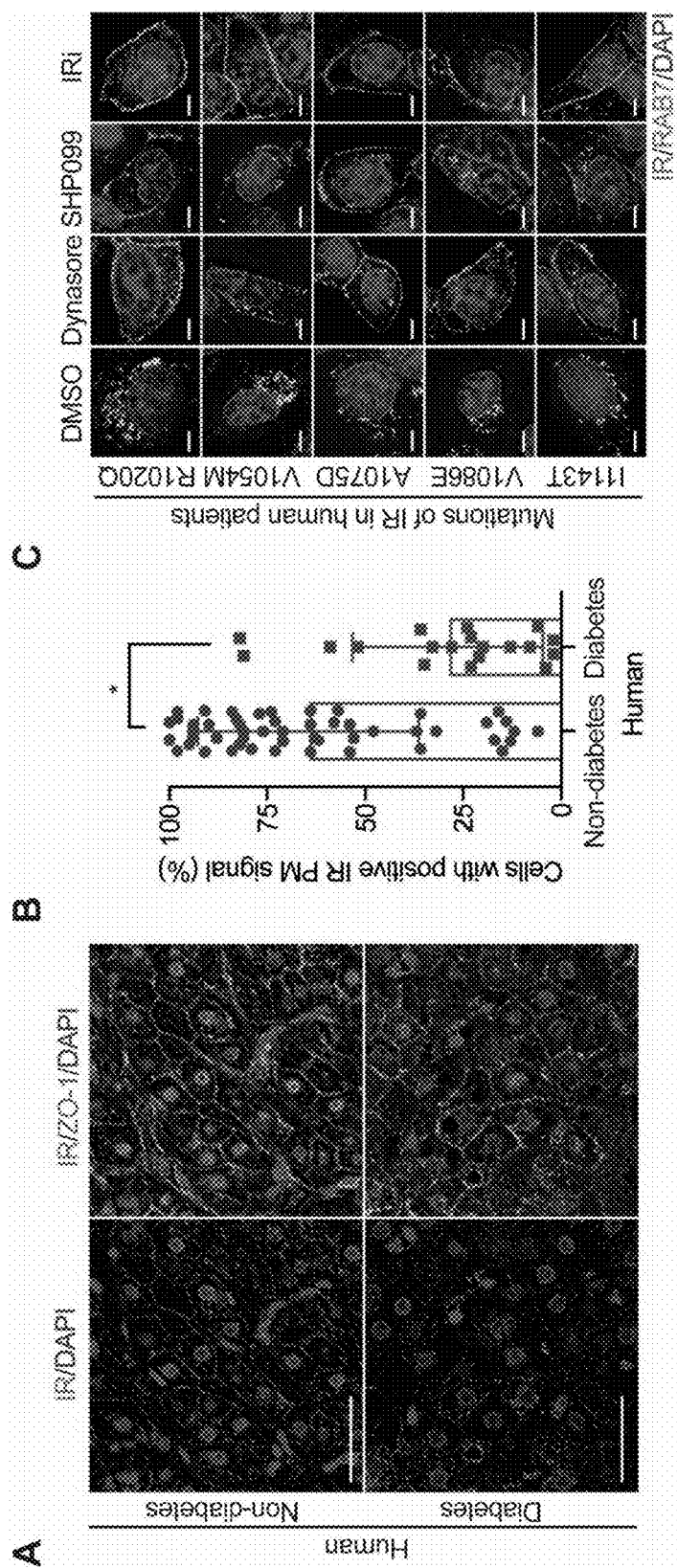
FIGS. 4A-C

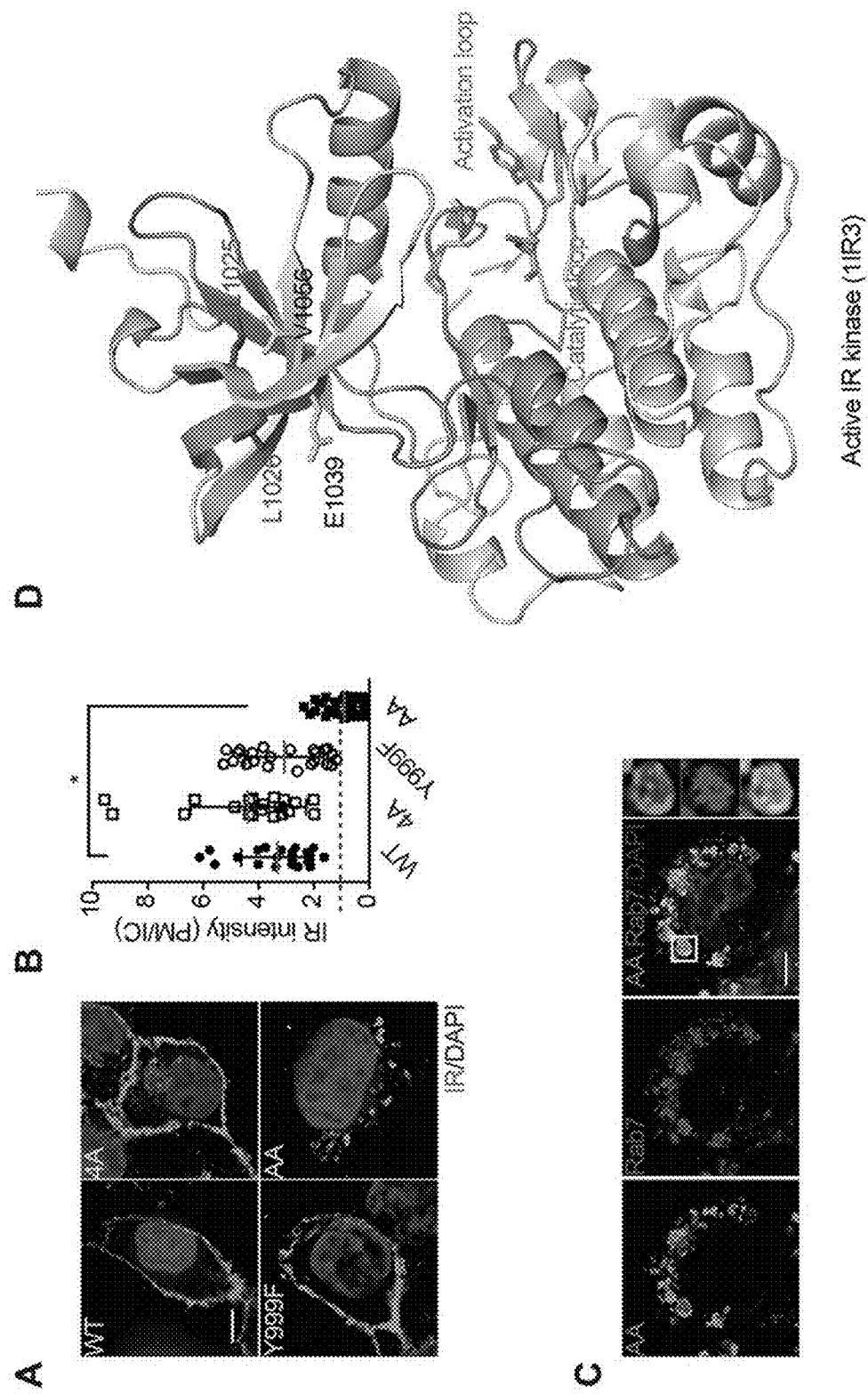
FIGS. 5A-D

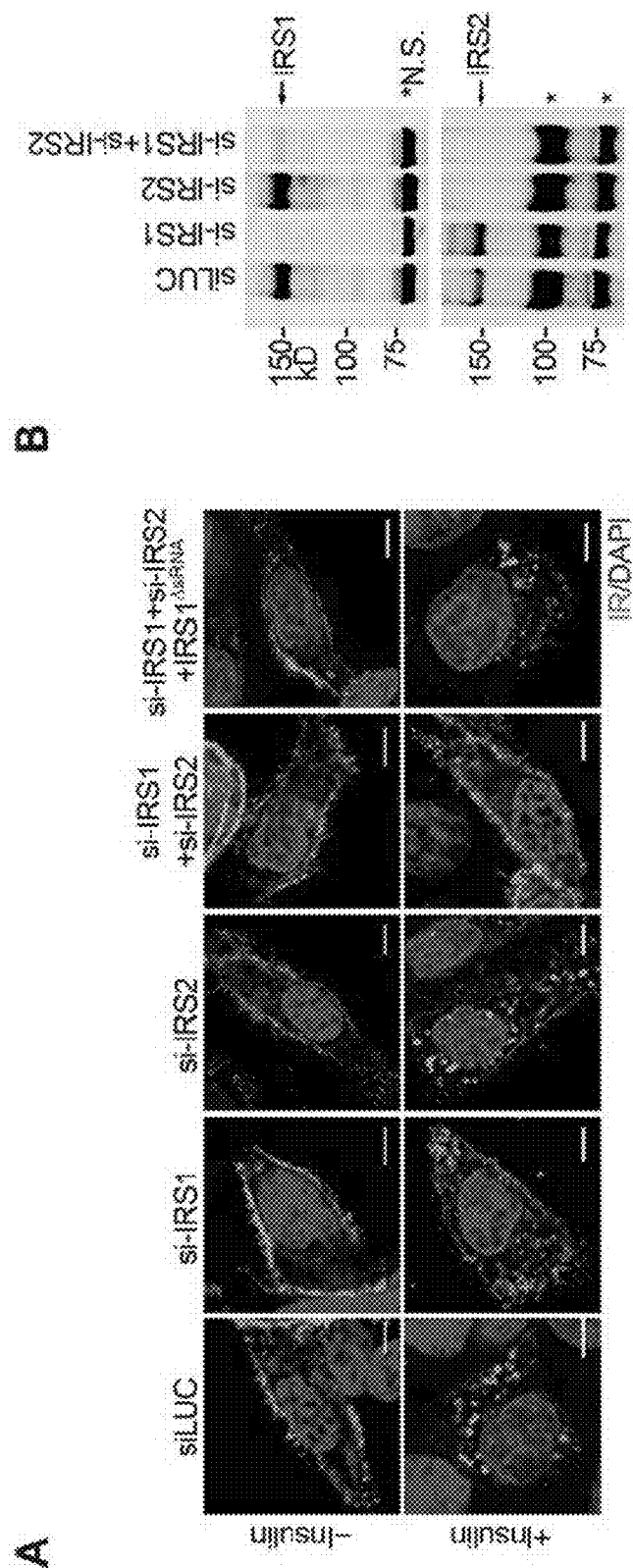
FIGS. 6A-B

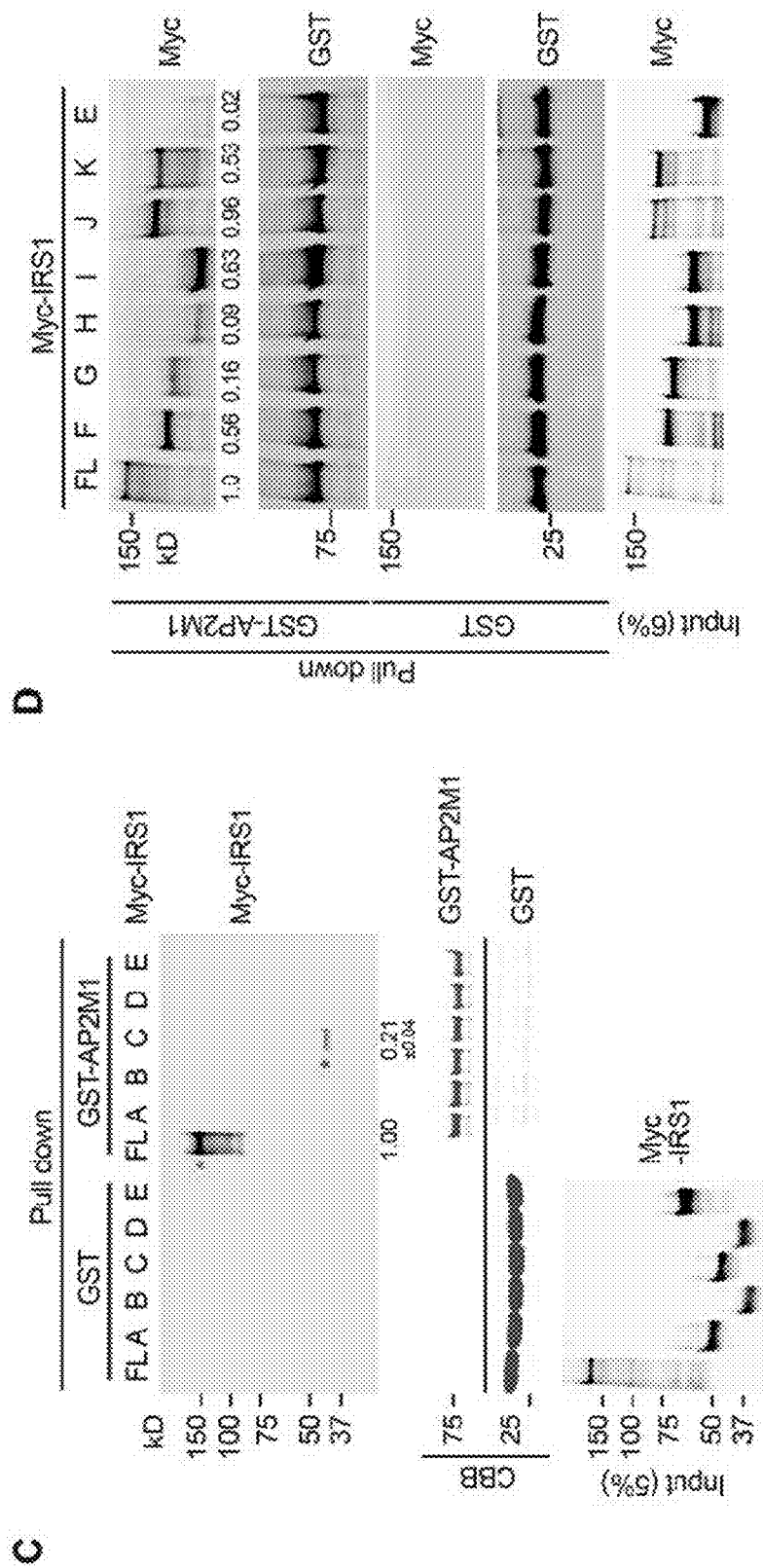
FIGS. 6C-D

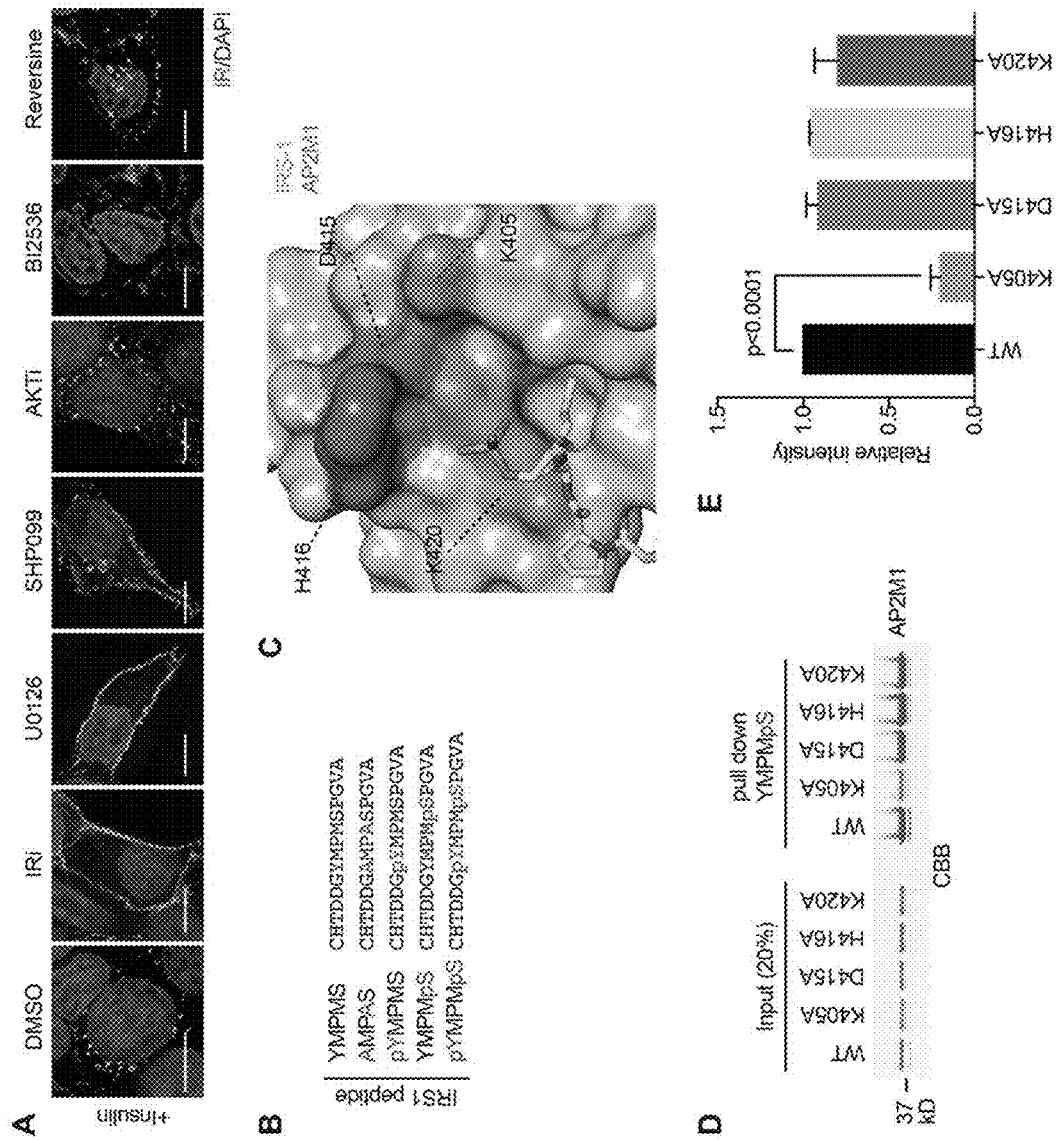
FIGS. 7A-E

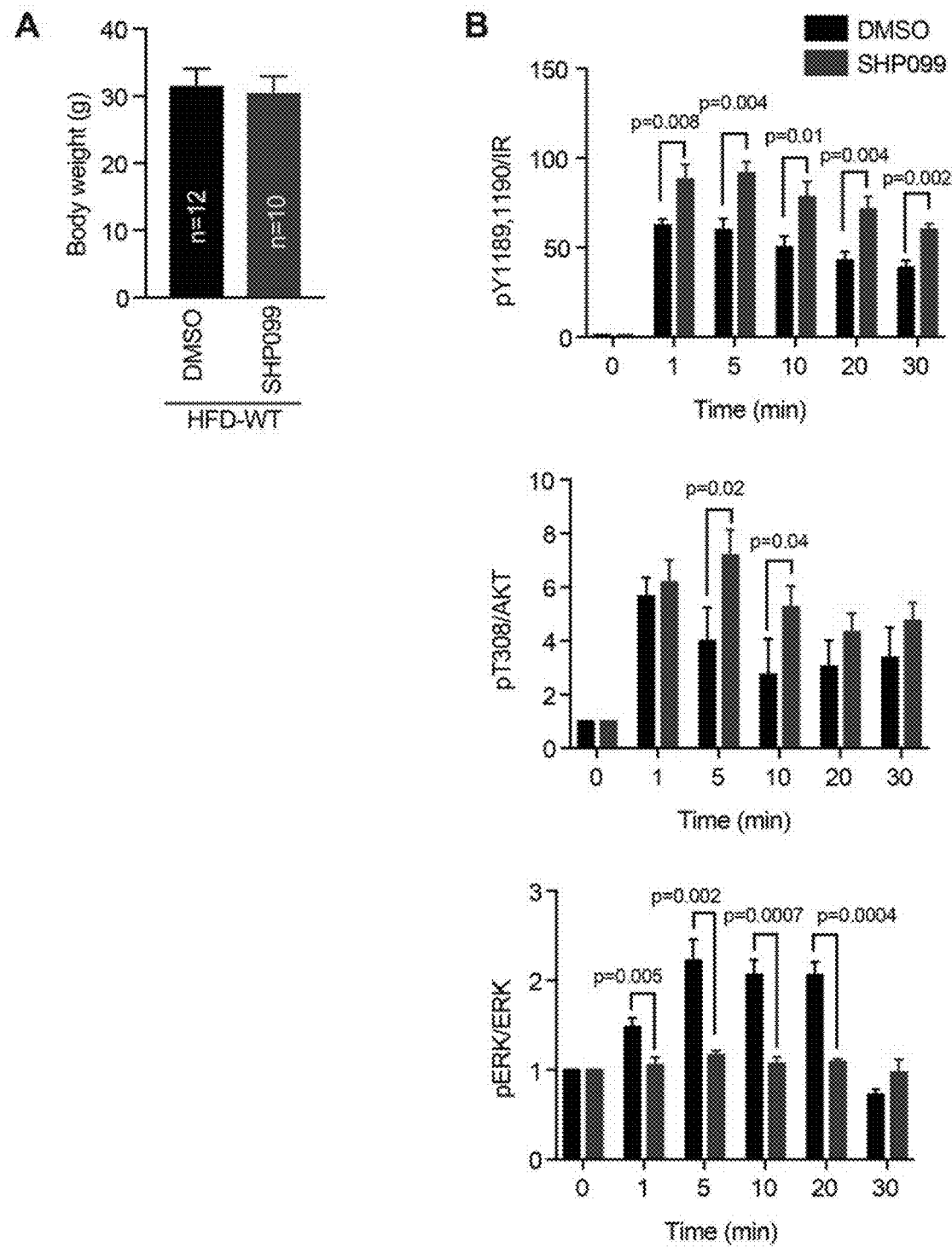
FIGS. 8A-B

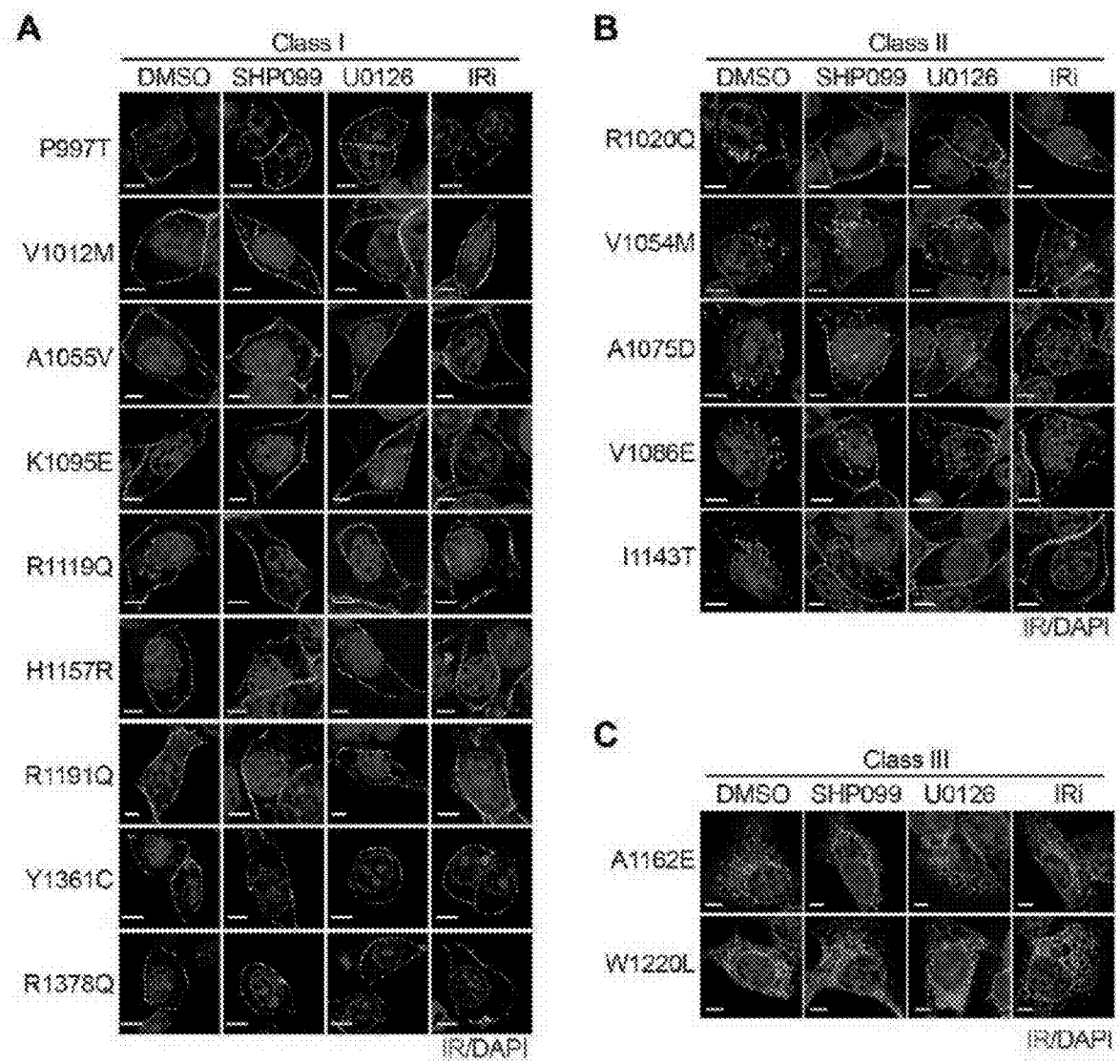
FIGS. 9A-C

SEQUENCE LISTING

<160> NUMBER OF SEQ ID NOS: 27

<210> SEQ ID NO 1
<211> LENGTH: 23
<212> TYPE: DNA
<213> ORGANISM: Artificial sequence

```
<220> FEATURE:
<223> OTHER INFORMATION: Synthetic oligo

<400> SEQUENCE: 1
aagaauccua ugguggaaac att                                           23

<210> SEQ ID NO 2
<211> LENGTH: 23
<212> TYPE: DNA
<213> ORGANISM: Artificial sequence
<220> FEATURE:
<223> OTHER INFORMATION: Synthetic oligo

<400> SEQUENCE: 2 uguuccacc auaggauucu utt                                            23

<210> SEQ ID NO 3
<211> LENGTH: 21
<212> TYPE: RNA
<213> ORGANISM: Artificial sequence
<220> FEATURE:
<223> OTHER INFORMATION: Synthetic oligo

<400> SEQUENCE: 3
aagaauccua ugguggaaac a                                             21

<210> SEQ ID NO 4
<211> LENGTH: 21
<212> TYPE: RNA
<213> ORGANISM: Artificial sequence
<220> FEATURE:
<223> OTHER INFORMATION: Synthetic oligo

<400> SEQUENCE: 4 uguuccacc auaggauucu u                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic oligo

<400> SEQUENCE: 5
gaaccugauu gguaucuact t                                             21

<210> SEQ ID NO 6
<211> LENGTH: 19
<212> TYPE: RNA
<213> ORGANISM: Artificial sequence
<220> FEATURE:
<223> OTHER INFORMATION: Synthetic oligo

<400> SEQUENCE: 6
ucauuccgga uacugcgau                                                19

<210> SEQ ID NO 7
<211> LENGTH: 5
<212> TYPE: PRT
<213> ORGANISM: Artificial sequence
<220> FEATURE:
<223> OTHER INFORMATION: Synthetic peptide

<400> SEQUENCE: 7

Tyr Met Pro Met Ser
1               5
```

<210> SEQ ID NO 8
<211> LENGTH: 15
<212> TYPE: PRT
<213> ORGANISM: Artificial sequence
<220> FEATURE:
<223> OTHER INFORMATION: Synthetic peptide

<400> SEQUENCE: 8

Cys His Thr Asp Asp Gly Tyr Met Pro Met Ser Pro Gly Val Ala
1               5                   10                  15

<210> SEQ ID NO 9
<211> LENGTH: 5
<212> TYPE: PRT
<213> ORGANISM: Artificial sequence
<220> FEATURE:
<223> OTHER INFORMATION: Synthetic peptide

<400> SEQUENCE: 9

Ala Met Pro Ala Ser
1               5

<210> SEQ ID NO 10
<211> LENGTH: 15
<212> TYPE: PRT
<213> ORGANISM: Artificial sequence
<220> FEATURE:
<223> OTHER INFORMATION: Synthetic peptide

<400> SEQUENCE: 10

Cys His Thr Asp Asp Gly Ala Met Pro Ala Ser Pro Gly Val Ala
1               5                   10                  15

<210> SEQ ID NO 11
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PHOSPHORYLATION

<400> SEQUENCE: 11

Tyr Met Pro Met Ser
1               5

<210> SEQ ID NO 12
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: PHOSPHORYLATION

<400> SEQUENCE: 12

Cys His Thr Asp Asp Gly Tyr Met Pro Met Ser Pro Gly Val Ala
1               5                   10                  15

<210> SEQ ID NO 13
<211> LENGTH: 5
<212> TYPE: PRT
<213> ORGANISM: Artificial sequence

```
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 13

Tyr Met Pro Met Ser
1               5

<210> SEQ ID NO 14
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: PHOSPHORYLATION

<400> SEQUENCE: 14

Cys His Thr Asp Asp Gly Tyr Met Pro Met Ser Pro Gly Val Ala
1               5                   10                  15

<210> SEQ ID NO 15
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 15

Tyr Met Pro Met Ser
1               5

<210> SEQ ID NO 16
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 16

Cys His Thr Asp Asp Gly Tyr Met Pro Met Ser Pro Gly Val Ala
1               5                   10                  15

<210> SEQ ID NO 17
<211> LENGTH: 19
<212> TYPE: PRT
<213> ORGANISM: Artificial sequence
<220> FEATURE:
<223> OTHER INFORMATION: Synthetic peptide
```

<400> SEQUENCE: 17

Cys Lys Asn Glu Lys Lys Asn Lys Ile Glu Arg Asn Asn Lys Leu Lys
1               5                   10                  15

Gln Pro Pro

<210> SEQ ID NO 18
<211> LENGTH: 61
<212> TYPE: PRT
<213> ORGANISM: Homo sapiens

<400> SEQUENCE: 18

Asp Asp Gly Tyr Met Pro Met Ser Pro Gly Val Ala Pro Val Pro Ser
1               5                   10                  15

Gly Arg Lys Gly Ser Gly Asp Tyr Met Pro Met Ser Pro Lys Ser Val
                20                  25                  30

Ser Ala Pro Gln Gln Ile Ile Asn Pro Ile Arg Arg His Pro Gln Arg
            35                  40                  45

Val Pro Asp Asn Gly Tyr Met Met Met Ser Pro Ser Gly
        50                  55                  60

<210> SEQ ID NO 19
<211> LENGTH: 61
<212> TYPE: PRT
<213> ORGANISM: Mus musculus

<400> SEQUENCE: 19

Asp Asp Gly Tyr Met Pro Met Leu Pro Gly Val Ala Pro Val Pro Ser
1               5                   10                  15

Asn Arg Lys Gly Asn Gly Asp Tyr Met Pro Met Ser Pro Lys Ser Val
                20                  25                  30

Ser Ala Pro Gln Gln Ile Ile Asn Pro Ile Arg Arg His Pro Gln Arg
            35                  40                  45

Val Pro Asp Asn Gly Tyr Met Met Met Ser Pro Ser Gly
        50                  55                  60

<210> SEQ ID NO 20
<211> LENGTH: 61
<212> TYPE: PRT
<213> ORGANISM: Rattus norvegicus

<400> SEQUENCE: 20

Asp Asp Gly Tyr Met Pro Met Leu Pro Gly Val Ala Pro Val Pro Ser
1               5                   10                  15

Asn Arg Lys Gly Asn Gly Asp Tyr Met Pro Met Ser Pro Lys Ser Val
                20                  25                  30

Ser Ala Pro Gln Gln Ile Ile Asn Pro Ile Arg Arg His Pro Gln Arg
            35                  40                  45

Val Pro Asp Asn Gly Tyr Met Met Met Ser Pro Ser Gly
        50                  55                  60

<210> SEQ ID NO 21
<211> LENGTH: 56
<212> TYPE: PRT
<213> ORGANISM: Xenopus tropicalis

<400> SEQUENCE: 21

Asp Asp Gly Tyr Met Pro Met Ser Pro Gly Val Ala Pro Val Pro Thr
1               5                   10                  15

Lys Ser Asn Asp Tyr Met Pro Met Ser Pro Lys Ser Val Ser Ala Pro 20                  25                  30

Gln Gln Ile Ile Asn Pro Arg Arg His Ser Ala Val Asp Ser Asn Gly
            35                  40                  45

Tyr Met Met Met Ser Pro Ser Gly
        50                  55

<210> SEQ ID NO 22
<211> LENGTH: 58
<212> TYPE: PRT
<213> ORGANISM: Danio rerio

<400> SEQUENCE: 22

Asp Asp Gly Tyr Met Pro Met Leu Pro Gly Val Ala Pro Ala Thr Pro
1               5                   10                  15

Thr Thr Lys Ser Ser Asp Tyr Met Pro Met Ser Pro Lys Ser Val Ser
                20                  25                  30

Ala Pro Gln Gln Ile Ile Asn Pro Arg Gln His Ser His Val Asp Ser
            35                  40                  45

Asn Gly Tyr Met Met Met Ser Pro Ser Gly
        50                  55

<210> SEQ ID NO 23
<211> LENGTH: 68
<212> TYPE: PRT
<213> ORGANISM: Homo sapiens

<400> SEQUENCE: 23

Asp Asp Gly Tyr Met Pro Met Thr Pro Gly Ala Ala Leu Ala Gly Ser
1               5                   10                  15

Gly Ser Gly Ser Cys Arg Ser Asp Asp Tyr Met Pro Met Ser Pro Ala
                20                  25                  30

Ser Val Ser Ala Pro Lys Gln Ile Leu Gln Pro Arg Ala Ala Ala Ala
            35                  40                  45

Ala Ala Ala Ala Val Pro Ser Ala Gly Pro Ala Gly Pro Ala Pro Thr
        50                  55                  60

Ser Ala Ala Gly
65

<210> SEQ ID NO 24
<211> LENGTH: 64
<212> TYPE: PRT
<213> ORGANISM: Mus musculus

<400> SEQUENCE: 24

Asp Asp Gly Tyr Met Pro Met Thr Pro Gly Ala Ala Leu Arg Ser Gly
1               5                   10                  15

Gly Pro Asn Ser Cys Lys Ser Asp Asp Tyr Met Pro Met Ser Pro Thr
                20                  25                  30

Ser Val Ser Ala Pro Lys Gln Ile Leu Gln Pro Arg Leu Ala Ala Ala
            35                  40                  45

Leu Pro Pro Ser Gly Ala Ala Val Pro Ala Pro Pro Ser Gly Val Gly
        50                  55                  60

<210> SEQ ID NO 25
<211> LENGTH: 64
<212> TYPE: PRT
<213> ORGANISM: Rattus norvegicus

<400> SEQUENCE: 25

```
Asp Asp Gly Tyr Met Pro Met Thr Pro Gly Ala Ala Leu Arg Ser Gly
1               5                   10                  15

Gly Pro Asn Ser Cys Lys Ser Asp Asp Tyr Met Pro Met Ser Pro Thr
            20                  25                  30

Ser Val Ser Ala Pro Lys Gln Ile Leu Gln Pro Arg Ser Ala Ala Ala
        35                  40                  45

Leu Pro Pro Ser Gly Ala Ala Val Pro Ala Pro Pro Ser Gly Val Gly
    50                  55                  60

<210> SEQ ID NO 26
<211> LENGTH: 44
<212> TYPE: PRT
<213> ORGANISM: Xenopus tropicalis

<400> SEQUENCE: 26

Asp Asp Gly Tyr Met Pro Met Ser His Gly Val Gly Val Ser Ser Ser
1               5                   10                  15

Asp Tyr Val Pro Met Ser Pro Ala Ser Val Ser Ala Pro Gln Gln Ile
            20                  25                  30

Leu Gln Pro Arg Cys Cys Ser Glu Thr Phe Glu Phe
        35                  40

<210> SEQ ID NO 27
<211> LENGTH: 45
<212> TYPE: PRT
<213> ORGANISM: Danio rerio

<400> SEQUENCE: 27

Asp Asp Gly Tyr Met Pro Met Thr Pro Gly Val Ala Pro Gln Gly Gly
1               5                   10                  15

Lys Ala Asp Asn Tyr Met Pro Met Ser Ser Met Cys Val Ser Ala Pro
            20                  25                  30

Lys Gln Ile Ile Asn Pro Arg Thr His Pro Leu Thr Ile
        35                  40                  45
```

SHP2 INHIBITORS AND METHODS OF USE THEREOF

This application claims the benefit of U.S. Provisional Patent Application No. 62/623,958, filed Jan. 30, 2018, the entirety of which is incorporated herein by reference.

This invention was made with government support under Grant No. GM124096 awarded by the National Institutes of Health. The government has certain rights in the invention.

BACKGROUND OF THE INVENTION

1. Field of the Invention

The present invention relates generally to the field of molecular biology and medicine. More particularly, it relates to treatments for diseases involving insulin receptors, such as diabetes.

2. Description of Related Art

The incidence of insulin resistance diseases, including type 2 diabetes, around the world has increased dramatically in recent years, reaching epidemic levels. Insulin resistance, characterized by a reduced response to insulin in the liver, skeletal muscle and adipose tissue, is a central factor in the development of type 2 diabetes (Samuel and Shulman, 2012; White, 2003).

Insulin resistance diseases typically affect insulin production or sensitivity and may result in clinical complications including early death. Insulin resistance diseases include genetic diseases affecting insulin receptor (IR) function such as, e.g., Rabson-Mendenhall syndrome and Donohue syndrome, often called Leprechaunism (Challis and Semple, 2013). While Donohue syndrome often results in death within the first few years of life, Rabson-Mendenhall has a slower progression, and patients with Rabson-Mendenhall are highly susceptible to diabetic complications and ketoacidosis. Presently, effective treatments do not exist for Rabson-Mendenhall or Donohue syndrome. Other genetic insulin receptor defects can present later in life and result in significant insulin resistance. Clearly, there exists a need for new and improved treatments for diseases associated with insulin resistance including type 2 diabetes, Donohue syndrome (Leprechaunism), and Rabson-Mendenhall syndrome.

SUMMARY OF THE INVENTION

The present disclosure overcomes limitations in the prior art by providing, in some aspects, new compositions and methods for the treatment of insulin resistance diseases. The present invention is based, in part, on the finding that inhibiting SHP2 (e.g., with a SHP2 allosteric inhibitor or a SHP2 siRNA) can be used to reduce insulin receptor (IR) endocytosis and alleviate insulin resistance in vivo. In some aspects, a SHP2 inhibitor may be used to treat insulin resistance or an insulin receptor disease such as, e.g., type 2 diabetes, Donohue syndrome or Leprechaunism, or Rabson-Mendenhall syndrome. In some aspects, liver-targeting liposomes or nanoparticles comprising a SHP2 siRNA or RNAi are provided and may be used to treat an IR disease. In some embodiments, the patient has both cancer and an IR disease, such as type 2 diabetes.

An aspect of the present invention relates to a method of treating a disease in a mammalian subject comprising administering a therapeutically effective amount of a compound or an siRNA to the subject; wherein the siRNA inhibits expression of SHP2 in the subject, and wherein the compound is an allosteric inhibitor of SHP2; and wherein the disease is Rabson-Mendenhall syndrome, insulin resistance, Donohue syndrome or Leprechaunism, or type II diabetes. In some embodiments, the compound is further defined as:

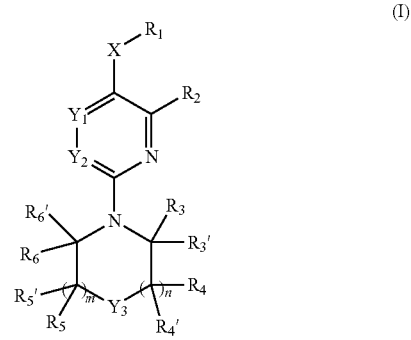

(I)

wherein:
$R_1$ is cycloalkyl$_{(C\leq12)}$, cycloalkenyl$_{(C\leq12)}$, aryl$_{(C\leq12)}$, heteroaryl$_{(C\leq12)}$, heterocycloalkyl$_{(C\leq12)}$, or a substituted version of any of these groups;
X is a covalent bond, O, NR$_{10}$, S(O)$_p$, C(O), COR$_{11}$, CR$_{10}$R$_{10}$'; wherein:
 p is 0, 1, or 2;
 $R_{10}$ and $R_{10}$' are each independently hydrogen, halo, alkyl$_{(C\leq6)}$, or substituted alkyl$_{(C\leq6)}$;
 $R_{11}$ is alkanediyl$_{(C\leq6)}$ or substituted alkanediyl$_{(C\leq6)}$;
$Y_1$ and $Y_2$ are each independently N or CR$_9$, wherein:
 $R_9$ is hydrogen, amino, cyano, halo, hydroxy, alkyl$_{(C\leq6)}$, substituted alkyl$_{(C\leq6)}$, alkoxy$_{(C\leq6)}$, substituted alkoxy$_{(C\leq6)}$, amido$_{(C\leq6)}$, substituted amido$_{(C\leq6)}$, acyl$_{(C\leq6)}$, substituted acyl$_{(C\leq6)}$, thioacyl$_{(C\leq6)}$, substituted thioacyl$_{(C\leq6)}$, alkylsulfinyl$_{(C\leq6)}$, substituted alkylsulfinyl$_{(C\leq6)}$, alkylsulfonyl$_{(C\leq6)}$, substituted alkylsulfonyl$_{(C\leq6)}$, —C(X$_1$)R$_a$, or —NR$_b$C(X$_2$)R$_c$, wherein:
  $X_1$ and $X_2$ are each independently O, S, or NR$_d$, wherein R$_d$ is hydrogen, alkyl$_{(C\leq6)}$, or substituted alkyl$_{(C\leq6)}$; and
  R$_a$ and R$_c$ are each independently alkyl$_{(C\leq6)}$, substituted alkyl$_{(C\leq6)}$, alkoxy$_{(C\leq6)}$, substituted alkoxy$_{(C\leq6)}$, alkylamino$_{(C\leq6)}$, substituted alkylamino$_{(C\leq6)}$, dialkylamino$_{(C\leq6)}$, substituted dialkylamino$_{(C\leq6)}$; and
  R$_b$ is hydrogen, alkyl$_{(C\leq6)}$, or substituted alkyl$_{(C\leq6)}$;
$R_2$ is amino, alkylamino$_{(C\leq8)}$, substituted alkylamino$_{(C\leq8)}$, dialkylamino$_{(C\leq8)}$, or substituted dialkylamino$_{(C\leq8)}$;
$R_3$, $R_3$', $R_4$, $R_4$', $R_5$, $R_5$', $R_6$, or $R_6$' are each independently hydrogen, amino, halo, hydroxy, alkyl$_{(C\leq6)}$, substituted alkyl$_{(C\leq6)}$, cycloalkyl$_{(C\leq6)}$, substituted cycloalkyl$_{(C\leq6)}$, alkoxy$_{(C\leq6)}$, substituted alkoxy$_{(C\leq6)}$, alkylamino$_{(C\leq6)}$, substituted alkylamino$_{(C\leq6)}$, dialkylamino$_{(C\leq6)}$, or substituted dialkylamino$_{(C\leq6)}$; or
$R_3$ and $R_3$', $R_4$ and $R_4$', $R_5$ and $R_5$' or $R_6$ and $R_6$' are taken together and are oxo; or
any two of $R_3$, $R_3$', $R_4$, $R_4$', $R_5$, $R_5$', $R_6$, $R_6$', and $R_7$ are taken together and form a cycloalkane$_{(C\leq12)}$, cycloalkene$_{(C\leq12)}$, arene$_{(C\leq12)}$, heteroarene$_{(C\leq12)}$, heterocycloalkane$_{(C\leq12)}$, or a substituted version of any of these groups;

m and n is 0, 1, or 2; and $Y_3$ is N or $CR_7R_8$, wherein:

$R_7$ and $R_8$ are each independently hydrogen, amino, or alkyl$_{(C \leq 12)}$, cycloalkyl$_{(C \leq 12)}$, aryl$_{(C \leq 12)}$, heteroaryl$_{(C \leq 12)}$, alkylamino$_{(C \leq 12)}$, dialkylamino$_{(C \leq 12)}$, or a substituted version of any of these groups; or $R_7$ and $R_8$ are taken together and form a cycloalkane$_{(C \leq 12)}$, cycloalkene$_{(C \leq 12)}$, arene$_{(C \leq 12)}$, heteroarene$_{(C \leq 12)}$, heterocycloalkane$_{(C \leq 12)}$, or a substituted version of any of these groups; or $R_7$ and $R_8$ are taken together and for a heterocycloalkane$_{(C \leq 12)}$ or a substituted heterocycloalkane$_{(C \leq 12)}$ which is further optionally substituted with an oxo group, an acyloxy$_{(C \leq 8)}$ group, or a substituted acyloxy$_{(C \leq 8)}$ group;

or a pharmaceutically acceptable salt thereof.

In some embodiments, the compound is further defined as:

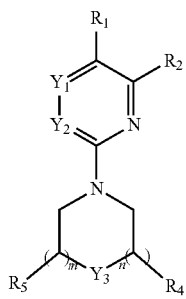

(II)

wherein:

$R_1$ is cycloalkyl$_{(C \leq 12)}$, cycloalkenyl$_{(C \leq 12)}$, aryl$_{(C \leq 12)}$, heteroaryl$_{(C \leq 12)}$, heterocycloalkyl$_{(C \leq 12)}$, or a substituted version of any of these groups;

$Y_1$ and $Y_2$ are each independently N or $CR_9$, wherein:

$R_9$ is hydrogen, amino, cyano, halo, hydroxy, alkyl$_{(C \leq 6)}$, substituted alkyl$_{(C \leq 6)}$, alkoxy$_{(C \leq 6)}$, substituted alkoxy$_{(C \leq 6)}$, amido$_{(C \leq 6)}$, substituted amido$_{(C \leq 6)}$, acyl$_{(C \leq 6)}$, substituted acyl$_{(C \leq 6)}$, thioacyl$_{(C \leq 6)}$, substituted thioacyl$_{(C \leq 6)}$, alkylsulfinyl$_{(C \leq 6)}$, substituted alkylsulfinyl$_{(C \leq 6)}$, alkylsulfonyl$_{(C \leq 6)}$, substituted alkylsulfonyl$_{(C \leq 6)}$, —C($X_1$)$R_a$, or —N$R_b$C($X_2$)$R_c$, wherein:

$X_1$ and $X_2$ are each independently O, S, or $NR_d$, wherein $R_d$ is hydrogen, alkyl$_{(C \leq 6)}$, or substituted alkyl$_{(C \leq 6)}$; and $R_a$ and $R_c$ are each independently alkyl$_{(C \leq 6)}$, substituted alkyl$_{(C \leq 6)}$, alkoxy$_{(C \leq 6)}$, substituted alkoxy$_{(C \leq 6)}$, alkylamino$_{(C \leq 6)}$, substituted alkylamino$_{(C \leq 6)}$, dialkylamino$_{(C \leq 6)}$, substituted dialkylamino$_{(C \leq 6)}$; and $R_b$ is hydrogen, alkyl$_{(C \leq 6)}$, or substituted alkyl$_{(C \leq 6)}$;

$R_2$ is amino, alkylamino$_{(C \leq 8)}$, substituted alkylamino$_{(C \leq 8)}$, dialkylamino$_{(C \leq 8)}$, or substituted dialkylamino$_{(C \leq 8)}$;

$R_4$ or $R_5$ are each independently hydrogen, amino, halo, hydroxy, alkyl$_{(C \leq 6)}$, substituted alkyl$_{(C \leq 6)}$, cycloalkyl$_{(C \leq 6)}$, substituted cycloalkyl$_{(C \leq 6)}$, alkoxy$_{(C \leq 6)}$, substituted alkoxy$_{(C \leq 6)}$, alkylamino$_{(C \leq 6)}$, substituted alkylamino$_{(C \leq 6)}$, dialkylamino$_{(C \leq 6)}$, or substituted dialkylamino$_{(C \leq 6)}$; or m and n is 0, 1, or 2; and $Y_3$ is N or $CR_7R_8$, wherein:

$R_7$ and $R_8$ are each independently hydrogen, amino, or alkyl$_{(C \leq 12)}$, cycloalkyl$_{(C \leq 12)}$, aryl$_{(C \leq 12)}$, heteroaryl$_{(C \leq 12)}$, alkylamino$_{(C \leq 12)}$, dialkylamino$_{(C \leq 12)}$, or a substituted version of any of these groups; or $R_7$ and $R_8$ are taken together and form a cycloalkane$_{(C \leq 12)}$, cycloalkene$_{(C \leq 12)}$, arene$_{(C \leq 12)}$, heteroarene$_{(C \leq 12)}$, heterocycloalkane$_{(C \leq 12)}$, or a substituted version of any of these groups;

or a pharmaceutically acceptable salt thereof.

In some embodiments, the compound is further defined as:

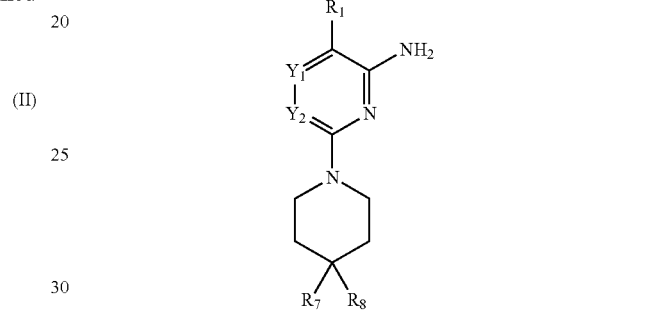

(II)

wherein:

$R_1$ is cycloalkyl$_{(C \leq 12)}$, cycloalkenyl$_{(C \leq 12)}$, aryl$_{(C \leq 12)}$, heteroaryl$_{(C \leq 12)}$, heterocycloalkyl$_{(C \leq 12)}$, or a substituted version of any of these groups;

$Y_1$ and $Y_2$ are each independently N or $CR_9$, wherein:

$R_9$ is hydrogen, amino, cyano, halo, hydroxy, alkyl$_{(C \leq 6)}$, substituted alkyl$_{(C \leq 6)}$, alkoxy$_{(C \leq 6)}$, substituted alkoxy$_{(C \leq 6)}$, amido$_{(C \leq 6)}$, substituted amido$_{(C \leq 6)}$, acyl$_{(C \leq 6)}$, substituted acyl$_{(C \leq 6)}$, thioacyl$_{(C \leq 6)}$, substituted thioacyl$_{(C \leq 6)}$, alkylsulfinyl$_{(C \leq 6)}$, substituted alkylsulfinyl$_{(C \leq 6)}$, alkylsulfonyl$_{(C \leq 6)}$, substituted alkylsulfonyl$_{(C \leq 6)}$, —C($X_1$)$R_a$, or —N$R_b$C($X_2$)$R_c$, wherein:

$X_1$ and $X_2$ are each independently O, S, or $NR_d$, wherein $R_d$ is hydrogen, alkyl$_{(C \leq 6)}$, or substituted alkyl$_{(C \leq 6)}$; and $R_a$ and $R_c$ are each independently alkyl$_{(C \leq 6)}$, substituted alkyl$_{(C \leq 6)}$, alkoxy$_{(C \leq 6)}$, substituted alkoxy$_{(C \leq 6)}$, alkylamino$_{(C \leq 6)}$, substituted alkylamino$_{(C \leq 6)}$, dialkylamino$_{(C \leq 6)}$, substituted dialkylamino$_{(C \leq 6)}$; and $R_b$ is hydrogen, alkyl$_{(C \leq 6)}$, or substituted alkyl$_{(C \leq 6)}$; and $R_7$ and $R_8$ are each independently hydrogen, amino, or alkyl$_{(C \leq 12)}$, cycloalkyl$_{(C \leq 12)}$, aryl$_{(C \leq 12)}$, heteroaryl$_{(C \leq 12)}$, alkylamino$_{(C \leq 12)}$, dialkylamino$_{(C \leq 12)}$, or a substituted version of any of these groups; or $R_7$ and $R_8$ are taken together and form a cycloalkane$_{(C \leq 12)}$, cycloalkene$_{(C \leq 12)}$, arene$_{(C \leq 12)}$, heteroarene$_{(C \leq 12)}$, heterocycloalkane$_{(C \leq 12)}$, or a substituted version of any of these groups;

or a pharmaceutically acceptable salt thereof.

In some embodiments, the compound is further defined as:

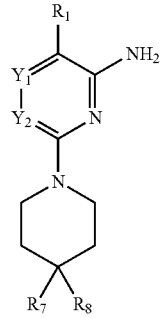

(II)

wherein:
R$_1$ is aryl$_{(C\leq12)}$ or substituted aryl$_{(C\leq12)}$;
Y$_1$ and Y$_2$ are each independently N or CR$_9$, wherein:
R$_9$ is hydrogen, amino, alkyl$_{(C\leq6)}$, substituted alkyl$_{(C\leq6)}$, alkoxy$_{(C\leq6)}$, substituted alkoxy$_{(C\leq6)}$, amido$_{(C\leq6)}$, substituted amido$_{(C\leq6)}$, acyl$_{(C\leq6)}$, or substituted acyl$_{(C\leq6)}$;
R$_7$ is hydrogen or alkyl$_{(C\leq12)}$, cycloalkyl$_{(C\leq12)}$, aryl$_{(C\leq12)}$, heteroaryl$_{(C\leq12)}$, or a substituted version of any of these groups; and
R$_8$ is amino, substituted alkyl$_{(C\leq12)}$, alkylamino$_{(C\leq12)}$, substituted alkylamino$_{(C\leq12)}$, dialkylamino$_{(C\leq12)}$, or substituted dialkylamino$_{(C\leq12)}$;
or a pharmaceutically acceptable salt thereof.

In some embodiments, R$_1$ is substituted aryl$_{(C\leq12)}$. In some embodiments, R$_1$ is dichlorophenyl or 2,3-dichlorophenyl. In some embodiments, Y$_1$ is N. In some embodiments, Y$_2$ is CH. R$_7$ may be alkyl$_{(C\leq12)}$ or substituted alkyl$_{(C\leq12)}$. In some embodiments, R$_7$ is alkyl$_{(C\leq6)}$ or methyl. R$_8$ may be amino, aminomethyl, or methylamino. In some embodiments, R$_8$ is amino. In some embodiments, the compound is a compound in Table 1. In some embodiments, the compound is:

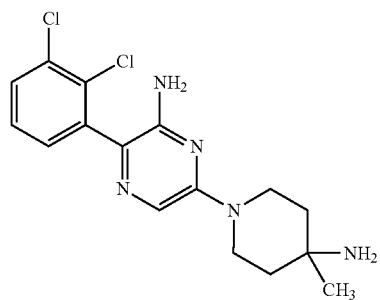 [SMILES: CC1(N)CCN(c2cnc(-c3cccc(Cl)c3Cl)c(N)n2)CC1]

or a pharmaceutically acceptable salt thereof.

In other embodiments, the compound is:

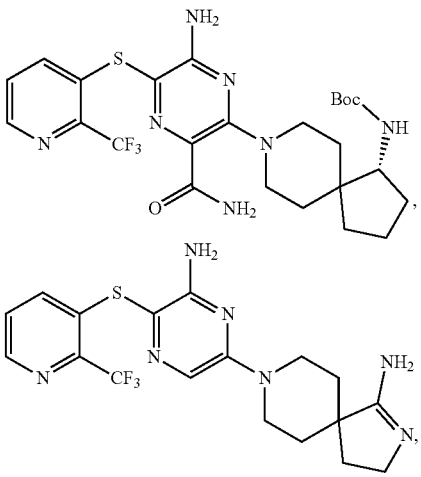

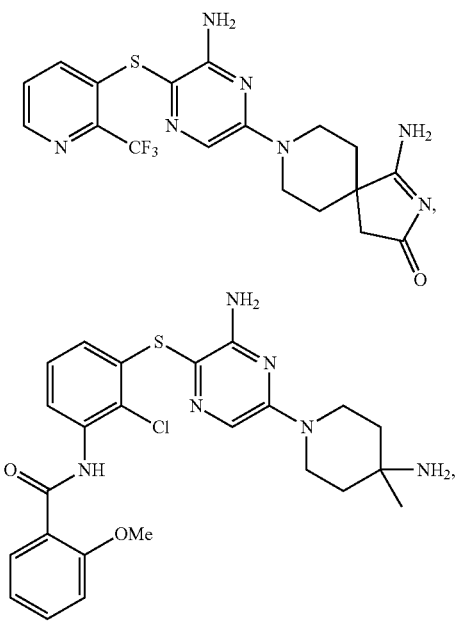

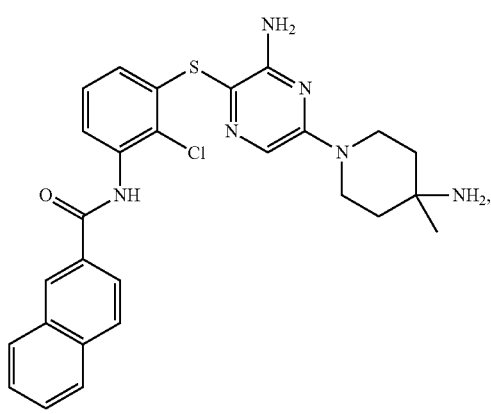

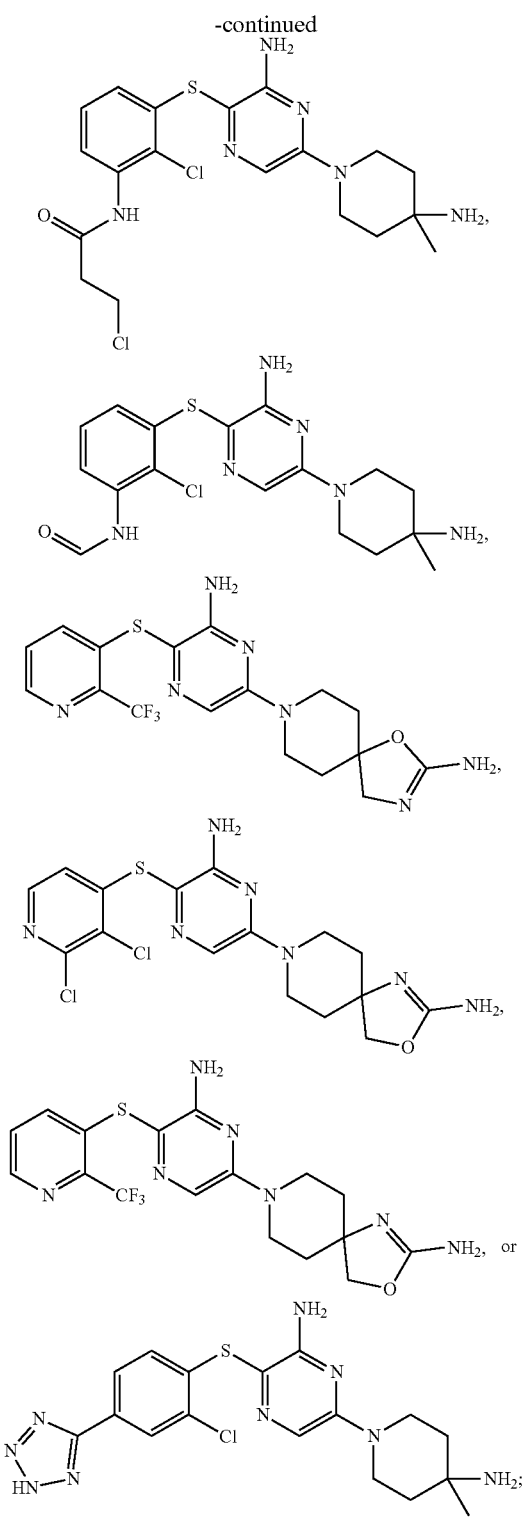

or a pharmaceutically acceptable salt thereof.

The siRNA may comprise or consist of the sequence AAGAAUCCUAUGGUGGAAACA-dTdT (SEQ ID NO:1), UGUUUCCACCAUAGGAUUCUU-dTdT (SEQ ID NO:2), AAGAAUCCUAUGGUGGAAACA (SEQ ID NO:3), or UGUUUCCACCAUAGGAUUCUU (SEQ ID NO:4). The subject may be a human. In some embodiments, the subject has an insulin receptor disease (IR). The subject may have type II diabetes. The subject may have a familial or genetic form of diabetes. The subject may have Leprechaunism or Rabson-Mendenhall syndrome. In some embodiments, the subject has a mutation in or affecting the insulin receptor (IR). In some embodiments, the subject is a human and has a P997T, V1012M, A1055V, K1095E, R1119Q, H1157R, R1191Q, Y1361C, R1378Q, R1020Q, V1054M, A1075D, V1086E, I1143T, A1162E, or W1220L mutation in the insulin receptor. A second compound may be administered to the subject to treat diabetes The second compound may be metformin, a sulfonylurea, a meglitinide, a thiazolidinedione, a DPP-4 inhibitor, a GLP-1 receptor agonist, a SGLT2 inhibitor, or insulin. In some embodiments, the method is further defined as a method for increasing insulin sensitivity or insulin receptor expression in the subject. The subject may have a cancer such as, e.g., juvenile myelomonocytic leukemia (JMML), neuroblastoma, melanoma, acute myeloid leukemia, breast cancer, lung cancer, colon cancer, liver cancer, or pancreatic cancer. In some embodiments, a second compound is administered to the subject to treat the cancer. In some embodiments, the second compound is altretamine, busulfan, carboplatin, carmustine, chlorambucil, cisplatin, cyclophosphamide, dacarbazine, lomustine, melphalan, oxaliplatin, temozolomide, thiotepa, a taxane, a vinca alkaloid, paclitaxel, docetaxel, vincristine, vinblastine, vinorelbine or vinflunine, 5-fluorouracil (5-FU), or 5-fluoro-2-4(1H,3H)-pyrimidinedione, 6-mercaptopurine (6-MP), capecitabine, cytarabine, floxuridine, fludarabine, flutamide, gemcitabine, hydroxyurea, methotrexate, pemetrexed, daunorubicin, doxorubicin, epirubicin, idarubicin, actinomycin-D, bleomycin, mitomycin-C, mitoxantrone, topotecan, irinotecan, etoposide, or teniposide.

Another aspect of the present invention relates to a pharmaceutical composition comprising a SHP2 siRNA, wherein: (i) the SHP2 siRNA is comprised in a liposome, exosome, or nanoparticle that preferentially accumulates in, or is targeted to, the liver; (ii) the SHP2 siRNA is conjugated to N-acetylgalactosamine; or (iii) the SHP2 siRNA has a phosphorothioate or 2'-methoxyethyl modification. The siRNA may comprise or consist of the sequence AAGAAUCCUAUGGUGGAAACA-dTdT (SEQ ID NO:1), UGUUUCCACCAUAGGAUUCUU-dTdT (SEQ ID NO:2), AAGAAUCCUAUGGUGGAAACA (SEQ ID NO:3), or UGUUUCCACCAUAGGAUUCUU (SEQ ID NO:4). The siRNA may be a single-stranded or self-hybridizing, and may optionally contain a linker. The pharmaceutical composition may further comprise an allosteric inhibitor of SHP2 of the present invention or as disclosed above. The composition may further comprise an anti-cancer agent such as, e.g., altretamine, busulfan, carboplatin, carmustine, chlorambucil, cisplatin, cyclophosphamide, dacarbazine, lomustine, melphalan, oxaliplatin, temozolomide, thiotepa, a taxane, a vinca alkaloid, paclitaxel, docetaxel, vincristine, vinblastine, vinorelbine or vinflunine, 5-fluorouracil (5-FU), or 5-fluoro-2-4(1H,3H)-pyrimidinedione, 6-mercaptopurine (6-MP), capecitabine, cytarabine, floxuridine, fludarabine, flutamide, gemcitabine, hydroxyurea, methotrexate, pemetrexed, daunorubicin, doxorubicin, epirubicin, idarubicin, actinomycin-D, bleomycin, mitomycin-C, mitoxantrone, topotecan, irinotecan, etoposide, or teniposide. In some embodiments, the composition further comprises a modular degradable dendrimer. In some embodiments, the siRNA is comprised in the modular degradable dendrimer.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 1A-H. IRS1/2 are required for insulin-activated IR endocytosis. (FIG. 1A) Schematic illustration of sequence motifs (left) and mutants (right) of IRβ. TM, transmembrane domain. (FIG. 1B) HepG2 cells stably expressing IR-GFP WT, 4A, Y999F, or Y999F/4A were serum starved, treated without or with 100 nM insulin for the indicated durations, and stained with anti-GFP antibodies. Quantification of the ratios of PM and IC IR-GFP signals of cells was shown (mean±SD; *p<0.0001). (FIG. 1C) HepG2 cells stably expressing IR-GFP WT were transfected with the indicated siRNAs or siRNA-resistant Myc-IRS1, serum starved, treated without or with 100 nM insulin for 5 min, and stained with anti-GFP antibodies. Quantification of the ratios of PM and IC IR-GFP signals of cells was shown (mean±SD; *p<0.0001). (FIG. 1D) Domains and YXXD motifs of human IRS1. PH, pleckstrin homology domain; PTB, phosphotyrosine-binding domain. IRS1 fragments that can or cannot bind to AP2M1 are presented as red or black bars, respectively. (FIG. 1E) Sequence alignment of a conserved region in IRS1/2. Three YXXΦ motifs are boxed with red dashed lines. The phosphorylation sites of IR and MAPK are indicated as red and blue dots, respectively. (FIG. 1F) Binding of IRS1 WT and mutants to GST or GST-AP2M1. The relative band intensities are shown below (3YA, Y612A/Y632A/Y662A; mean±SD; n=3 independent experiments). (FIG. 1G) 293FT cells stably expressing IR-GFP WT were transfected with the indicated siRNAs or siRNA-resistant Myc-IRS1, serum starved, treated without or with 100 nM insulin for 5 min, and stained with anti-GFP (IR; green), anti-Myc (IRS1; red), and DAPI (blue). See also FIG. 6E for representative images. Quantification of the ratios of PM and IC IR-GFP signals of cells was shown (3YF, Y612F/Y632F/Y662F; 3SA, S616A/S636A/S666A; 3SD, S616D/S636D/S666D; mean±SD; *p<0.0001). (FIG. 1H) 293FT cells were serum starved and treated without or with 100 nM insulin for 5 min. Total cell lysate (TCL), anti-IRS1 IP, and IgG IP were blotted with anti-IRS1 and anti-AP2B1 antibodies.

FIGS. 2A-I. The MAPK pathway and SHP2 promote insulin-activated IR endocytosis. (FIG. 2A) HepG2 cells expressing IR-GFP WT were starved, treated with the indicated inhibitors for 2 h, treated without or with 100 nM insulin for 20 min, and stained with anti-GFP (IR; green) and DAPI (blue). See also FIG. 7A for representative images. Quantification of the ratios of PM and IC IR-GFP signals of cells was shown (mean±SD; *p<0.0001). (FIG. 2B) Binding of IRS1 peptides to AP2M1 (residues 160-435). Input and proteins bound to IRS1-peptide beads were analyzed by SDS-PAGE and stained with Coomassie (CBB). The relative band intensities are shown below (mean±SD; n=4 independent experiments). (FIG. 2C) ITC analysis of binding between IRS1 peptides and AP2M1 (residue 160-435), with the $K_d$ indicated. (FIG. 2D) The IRS1 peptides were incubated with active SHP2 for the indicated durations, spotted onto membranes, and detected with the anti-pY612-IRS1 antibody. (FIG. 2E) Quantification of the relative SHP2 activity in FIG. 2D (mean±SD; n=4 independent experiments; *p<0.0001). (FIG. 2F) Model of the regulation of insulin-activated IR endocytosis by a phosphorylation switch on IRS1/2. Insulin-bound IR phosphorylates itself and IRS1/2, and activates the PI3K-AKT and MAPK pathways. SHP2 acts upstream of RAS-RAF and promotes the activation of MAPK pathway. p31$^{comet}$ binds to the IR-bound MAD2 and blocks IR-AP2 association to prevent premature IR endocytosis. In feedback regulation, activated ERK1/2 phosphorylate S616 and other sites on IRS1. SHP2 binds to the C-terminal phospho-tyrosine site on IRS1 and dephosphorylates pY612 of the doubly phosphorylated IRS1 (pY612/pS616), thus promoting IRS1-AP2M1 association. p31$^{comet}$ is released from MAD2 by an unknown mechanism, allowing MAD2 to bind to BUBR1-AP2B1. MAD2- and IRS1/2-dependent AP2 recruitment and clustering trigger clathrin-mediated IR endocytosis. (FIG. 2G) Cartoon diagram of the crystal structure of AP2M1 (residues 160-435) bound to pS-IRS1. pS-IRS1 is shown in sticks. (FIG. 2H) Surface drawing of AP2M1, with pS-IRS1 shown in sticks. (FIG. 2I) A zoomed-in view of the surface drawing of AP2M1 colored by its electrostatic potential (blue, positive; red, negative; white, neutral). pS-IRS1 is shown in sticks.

FIGS. 3A-E. Inhibition of IR endocytosis by SHP099 prevents diet-induced diabetes in mice. (FIG. 3A) Glucose tolerance test in 14 h fasted male mice fed a HFD for 5 weeks. The mice were administered vehicle (DMSO) or SHP099 for 6 days. At 1 day after drug treatment, glucose tolerance test was performed. Mean±SEM. (FIG. 3B) Insulin tolerance test of mice treated as described in FIG. 3A. Mean±SEM. (FIG. 3C) HFD-fed WT mice were administered vehicle (DMSO) or SHP099 for 6 days. At 2 h after the last administration, the mice were injected with or without 5 U insulin via inferior vena cava. The liver sections were stained with anti-IR (red) and DAPI (blue). Scale bars, 5 μm. (FIG. 3D) Quantification of the ratios of PM and IC IR signals of the livers in C (mean±SD; *p<0.0001). (FIG. 3E) Primary hepatocytes were treated with DMSO or 10 μM SHP099 for 2 h and treated with 100 nM insulin for the indicated durations. Cell lysates were blotted with the indicated antibodies.

FIGS. 4A-E. Dysregulation of IR endocytosis as a potential contributing factor to human insulin resistance syndromes. (FIG. 4A) Representative images of liver specimens from human non-diabetes and diabetes patients stained with DAPI (blue) and anti-IR (red) and anti-ZO-1 (green) antibodies. Scale bars, 40 μm. (FIG. 4B) Quantification of the percentage of cells with positive IR PM signals in liver specimens in FIG. 4A (mean±SD; *p<0.0001). (FIG. 4C) HepG2 cells stably expressing IR-GFP R1020Q, V1054M, A1075D, V1086E, or I1143T were serum starved and stained with anti-GFP and anti-RAB7 antibodies. Scale bar, 5 μm. (FIG. 4D) Quantification of the ratios of PM and IC IR-GFP signals of cells in FIG. 4C (mean±SD; *p<0.0001). (FIG. 4E) Targeting feedback regulation of IR endocytosis for diabetes treatment. Left panel depicts the feedback regulation of IR endocytosis by ERK1/2 and SHP2 during unperturbed insulin signaling. Right panel illustrates the mechanism by which inhibitors of MEK (MEKi) or SHP2 (SHP099) block growth-promoting IR signaling and IR endocytosis, and prolong insulin signaling through the PI3K-AKT pathway, which controls metabolism.

FIGS. 5A-D. Y999 phosphorylation and the MAD2 interaction motif of IR, but not the di-leucine motif, are required for IR endocytosis. (FIG. 5A) HepG2 cells stably expressing IR-GFP WT, 4A, Y999F, or AA were serum starved and stained with anti-GFP antibodies. Scale bar, 10 μm. (FIG. 5B) Quantification of the ratios of plasma membrane (PM) and intracellular (IC) IR-GFP signals of cells in A (mean±SD; *p<0.0001). (FIG. 5C) HepG2 cells stably expressing IR-GFP AA were serum starved and stained with anti-GFP and anti-RAB7 antibodies. The boxed region was magnified and shown on the right. Scale bar, 10 μm. (FIG. 5D) Cartoon diagram of the crystal structure of the active IR kinase domain (PDB ID 1IR3). The di-leucine motif (L1025 and L1026) and neighboring residues (E1039 and V1056) are shown as sticks. Activation and catalytic loops are shown in green and orange, respectively.

FIGS. 6A-E. The YXXΦ motifs of IRS1/2 bind to AP2M1 and are required for insulin-activated IR endocytosis. (FIG. 6A) Representative images of IR staining in FIG. 1C. IR (green) and DAPI (blue); Scale bars, 10 μm. (FIG. 6B) Western blot analysis of cell lysates in FIG. 6A. Asterisks indicate non-specific bands. (FIG. 6C) Binding of IRS1 WT and mutants to GST or GST-AP2M1. Input and protein bound to beads were blotted with anti-Myc (IRS1) antibodies and stained with Coomassie (CBB). The relative band intensities are shown below (mean±SD; n=3 independent experiments). (FIG. 6D) Binding of IRS1 WT and mutants to GST or GST-AP2M1. Input and protein bound to beads were blotted with the indicated antibodies. The relative band intensities are shown below (n=2 independent experiments). (FIG. 6E) Representative images of IR and IRS1 staining in FIG. 1G. IR (green), IRS1 (red), and DAPI (blue). Scale bars, 10 μm.

FIGS. 7A-E. Phospho-regulation of IR endocytosis and the IRS1-AP2M1 interaction. (FIG. 7A) Representative images of IR staining in FIG. 2A. IR (green) and DAPI (blue); Scale bars, 10 μm. (FIG. 7B) Sequences of IRS1 peptides used in FIGS. 2B-E. (YMPMS (SEQ ID NO:7), CHTDDGYMPMSPGVA (SEQ ID NO:8); AMPAS (SEQ ID NO:9), CHTDDGAMPASPGVA (SEQ ID NO:10); pYMPMS (SEQ ID NO:11), CHTDDGpYMPMSPGVA (SEQ ID NO:12); YMPMpS (SEQ ID NO:13), CHTDDGYMPMpSPGVA (SEQ ID NO:14); pYMPMpS (SEQ ID NO:15), CHTDDGpYMPMpSPGVA (SEQ ID NO:16)) YXXΦ motifs and phospho-residues are shown in blue and red letters, respectively. (FIG. 7C) Surface drawing of AP2M1 with the bound pS-IRS1 shown in sticks. The potential acceptor residues for IRS1 pS616 are labeled. (FIG. 7D) Binding of the pS-IRS1 peptide to WT and mutants of AP2M1 (residues 160-435). Input and proteins bound to pS-IRS1 peptides were analyzed by SDS-PAGE and stained with Coomassie (CBB). (FIG. 7E) Quantification of the relative band intensities in D. Mean±SD; n=3 independent experiments.

FIGS. 8A-B. Effects of the SHP2 inhibitor on body weight and insulin signaling in HFD-WT mice. (FIG. 8A) Relative body weight change of WT mice administrated vehicle or SHP099 at 7 days post administration. Mean±SD. (FIG. 8B) Quantification of the relative band intensities in FIG. 3E. Mean±SD; n=3 independent experiments.

FIGS. 9A-D. Characterization of IR mutations found in human patients. (FIG. 9A) HepG2 cells expressing IR-GFP Class I mutants (P997T, V1012M, A1055V, K1095E, R1119Q, H1157R, R1191Q, Y1361C, or R1378Q) were starved for 14 h, treated with the indicated inhibitors for 4 h, and stained with anti-GFP (IR; green) and DAPI (blue). Scale bar, 5 m. (FIG. 9B) HepG2 cells expressing IR-GFP Class II mutants (R1020Q, V1054M, A1075D, V1086E, or I1143T) were analyzed as described in FIG. 9A. (FIG. 9C) HepG2 cells expressing IR-GFP Class III mutants (A1162E or W1220L) were analyzed as described in A. (FIG. 9D) HepG2 cells expressing IR-GFP WT, R1020Q, or V1054M were serum starved for 14 h and treated with DMSO or 80 μM Dynasore for 4 h. Cell lysates were blotted with the indicated antibodies.

DESCRIPTION OF ILLUSTRATIVE EMBODIMENTS

Figures 1A, 1B, 1C:
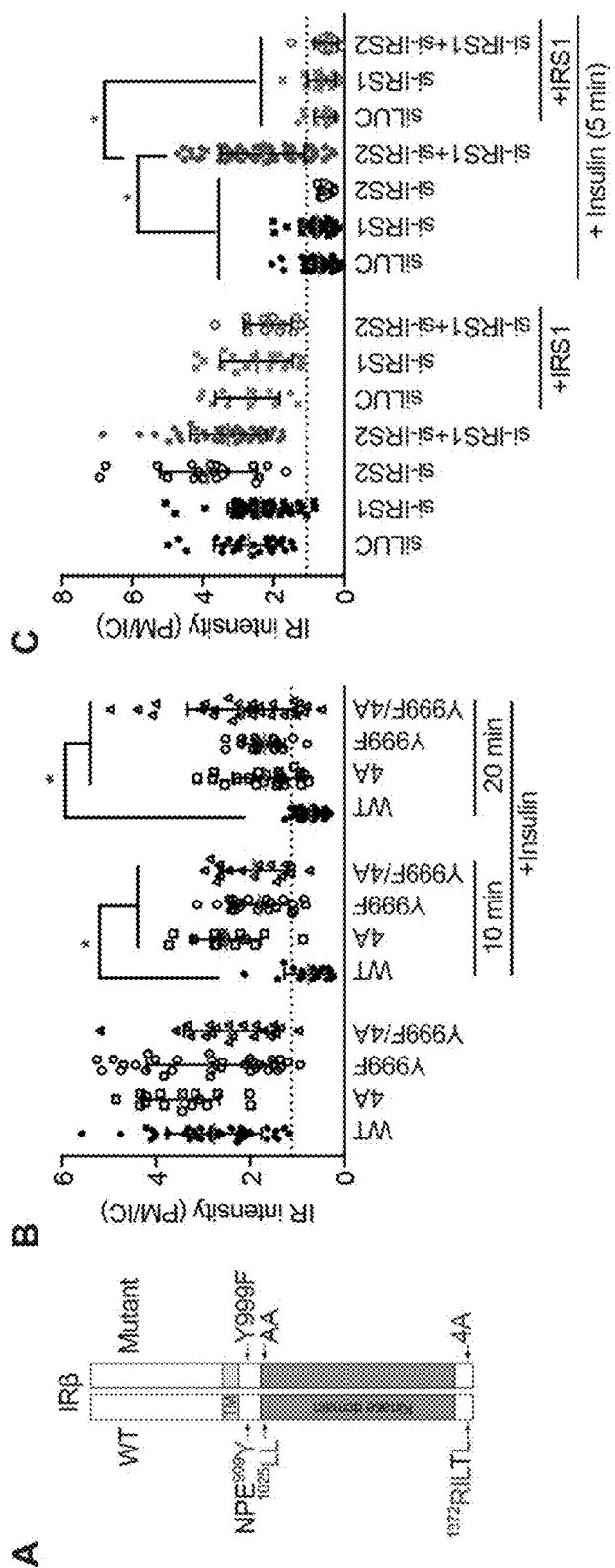

The present provides, in some aspects, methods for the treatment of diseases associated with insulin resistance or insulin receptor dysfunction. As shown in the below examples, SHP2 inhibition can promote IR signaling, prolong insulin action on glucose metabolism, and alleviate high-fat-diet-induced insulin resistance in vivo. More specifically, it was observed that insulin receptor substrate 1 and 2 (IRS1/2) cooperate with the MAD2 module to promote IR endocytosis, which also requires feedback regulation of IRS1/2 by activated extracellularly regulated kinase 1 and 2 (ERK1/2) and SHP2. SHP2 inhibition inhibited this feedback regulation and growth-promoting IR signaling, prolonging insulin action on glucose metabolism and alleviating high-fat-diet-induced insulin resistance in mice. Liver biopsies from human diabetes patients were observed to exhibit reduced plasma membrane IR levels. Several IR mutants linked to insulin resistance in humans undergo premature endocytosis, which was suppressed by SHP2 inhibition. These results indicate that SHP2 can affect feedback regulation of IR endocytosis. Administering a SHP2 inhibitor (e.g., an allosteric inhibitor of SHP2, a SHP2 antibody, or a SHP2 siRNA) may thus be used to treat insulin resistance or an insulin receptor dysfunction such a, e.g., type 2 diabetes or a genetic disorder affecting the IR.

In some aspects, a disease associated with insulin resistance or insulin receptor dysfunction (e.g., diseases involving one or more mutations in IR that adversely affect IR function, or diseases characterized by increased IR endocytosis) can be treated by administering a SHP2 inhibitor, such as a SHP2 allosteric inhibitor, a SHP2 RNAi, or a SHP2 siRNA, to a mammalian subject, such as a human. Also provided herein are pharmaceutical compositions comprising the SHP2 allosteric inhibitor, RNAi, or siRNA, and in some embodiments the therapeutic compound is comprised in a liposome or nanoparticle, such as a liposome or nanoparticle targeted to the liver. In some aspects, a SHP2 inhibitor (e.g., an allosteric inhibitor of SHP2 or a SHP2 siRNA) may be administered to a subject to reduce insulin resistance, reduce insulin receptor endocytosis, and/or treat type II diabetes. In some embodiments, the subject is a human patient that has both type II diabetes and cancer.

I. Src Homology Region 2 (SH2)-Containing Protein Tyrosine Phosphatase 2 (SHP2)

Src homology region 2 (SH2)-containing protein tyrosine phosphatase 2 (SHP2) (also known as tyrosine-protein phosphatase non-receptor type 11 (PTPN11), protein-tyrosine phosphatase 1D (PTP-1D), or protein-tyrosine phosphatase 2C (PTP-2C)) is a non-receptor phosphotyrosine phosphatase encoded by the PTPN11 gene. SHP2 is widely expressed in most tissues and plays a regulatory role in various cell signaling events that are important for a diversity of cell functions, including mitogenic activation, metabolic control, transcription regulation, and cell migration. SHP2 can affect signaling in RAS-mitogen-activated protein kinase (MAPK), JAK-STAT, and phosphoinositide 3-kinase (PI3K)-AKT pathways. SHP2 contains one protein tyrosine phosphatase (PTP) catalytic domain and two SH2 domains. Two tandem-arranged SH2 domains are found in the N-terminal region of SHP2 and a phosphatase domain is located in the C-terminal domain of SHP2 (Feng et al., 1994).

II. SHP2 Inhibitors

The present disclosure provides compounds and nucleic acids for inhibiting the activity of SHP2. A variety of SHP2 inhibitors have been described and synthesized that may be used in various embodiments to treat a disease associated with insulin resistance or insulin receptor dysfunction. These compounds include allosteric inhibitors of SHP2, such as:

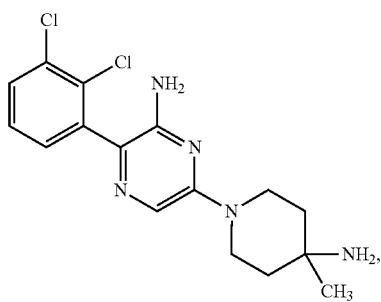

(SHP099)

as well as RNAi and siRNA that can decrease expression of SHP2 or are directed to the PTPN11 transcript. The present disclosure also provides pharmaceutical compositions comprising such compounds.

A. Small Molecule SHP2 Inhibitors

In some embodiments, the SHP2 inhibitor is an allosteric inhibitor of SHP2, e.g., a compound as described in US20170015680, US20170001975, or US20170204080, the entire contents of which are incorporated herein by reference. In another embodiment, the SHP2 inhibitor is a compound described in WO 2016/203404, the entire contents of which are hereby incorporated herein by reference.

These inhibitors are derivatives of the formula(s):

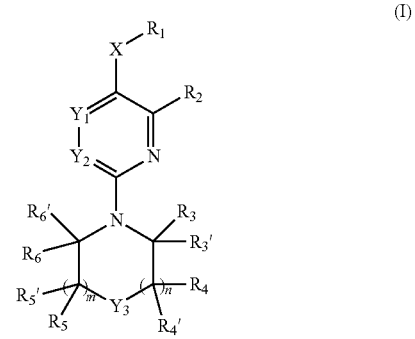

(I)

wherein:
R$_1$ is cycloalkyl$_{(C≤12)}$, cycloalkenyl$_{(C≤12)}$, aryl$_{(C≤12)}$, heteroaryl$_{(C≤12)}$, heterocycloalkyl$_{(C≤12)}$, or a substituted version of any of these groups;
X is a covalent bond, O, NR$_{10}$, S(O)$_p$, C(O), COR$_{11}$, CR$_{10}$R$_{10}$'; wherein:
p is 0, 1, or 2;
R$_{10}$ and R$_{10}$' are each independently hydrogen, halo, alkyl$_{(C≤6)}$, or substituted alkyl$_{(C≤6)}$;
R$_{11}$ is alkanediyl$_{(C≤6)}$ or substituted alkanediyl$_{(C≤6)}$;
Y$_1$ and Y$_2$ are each independently N or CR$_9$, wherein:
R$_9$ is hydrogen, amino, cyano, halo, hydroxy, alkyl$_{(C≤6)}$, substituted alkyl$_{(C≤6)}$, alkoxy$_{(C≤6)}$, substituted alkoxy$_{(C≤6)}$, amido$_{(C≤6)}$, substituted amido$_{(C≤6)}$, acyl$_{(C≤6)}$, substituted acyl$_{(C≤6)}$, thioacyl$_{(C≤6)}$, substituted thioacyl$_{(C≤6)}$, alkylsulfinyl$_{(C≤6)}$, substituted alkylsulfinyl$_{(C≤6)}$, alkylsulfonyl$_{(C≤6)}$, substituted alkylsulfonyl$_{(C≤6)}$, —C(X$_1$)R$_a$, or —NR$_b$C(X$_2$)R$_c$, wherein:
X$_1$ and X$_2$ are each independently O, S, or NR$_d$, wherein R$_d$ is hydrogen, alkyl$_{(C≤6)}$, or substituted alkyl$_{(C≤6)}$; and
R$_a$ and R$_c$ are each independently alkyl$_{(C≤6)}$, substituted alkyl$_{(C≤6)}$, alkoxy$_{(C≤6)}$, substituted alkoxy$_{(C≤6)}$, alkylamino$_{(C≤6)}$, substituted alkylamino$_{(C≤6)}$, dialkylamino$_{(C≤6)}$, substituted dialkylamino$_{(C≤6)}$; and
R$_b$ is hydrogen, alkyl$_{(C≤6)}$, or substituted alkyl$_{(C≤6)}$;
R$_2$ is amino, alkylamino$_{(C≤8)}$, substituted alkylamino$_{(C≤8)}$, dialkylamino$_{(C≤8)}$, or substituted dialkylamino$_{(C≤8)}$;
R$_3$, R$_3$', R$_4$, R$_4$', R$_5$, R$_5$', R$_6$, or R$_6$' are each independently hydrogen, amino, halo, hydroxy, alkyl$_{(C≤6)}$, substituted alkyl$_{(C≤6)}$, cycloalkyl$_{(C≤6)}$, substituted cycloalkyl$_{(C≤6)}$, alkoxy$_{(C≤6)}$, substituted alkoxy$_{(C≤6)}$, alkylamino$_{(C≤6)}$, substituted alkylamino$_{(C≤6)}$, dialkylamino$_{(C≤6)}$, or substituted dialkylamino$_{(C≤6)}$; or
R$_3$ and R$_3$', R$_4$ and R$_4$', R$_5$ and R$_5$' or R$_6$ and R$_6$' are taken together and are oxo; or
any two of R$_3$, R$_3$', R$_4$, R$_4$', R$_5$, R$_5$', R$_6$, R$_6$', and R$_7$ are taken together and form a cycloalkane$_{(C≤12)}$, cycloalkene$_{(C≤12)}$, arene$_{(C≤12)}$, heteroarene$_{(C≤12)}$, heterocycloalkane$_{(C≤12)}$, or a substituted version of any of these groups;
m and n is 0, 1, or 2; and
Y$_3$ is N or CR$_7$R$_8$, wherein:
R$_7$ and R$_8$ are each independently hydrogen, amino, or alkyl$_{(C≤12)}$, cycloalkyl$_{(C≤12)}$, aryl$_{(C≤12)}$, heteroaryl$_{(C≤12)}$, alkylamino$_{(C≤12)}$, dialkylamino$_{(C≤12)}$, or a substituted version of any of these groups; or R7 and R8 are taken together and form a cycloalkane$_{(C≤12)}$, cycloalkene$_{(C≤12)}$, arene$_{(C≤12)}$, heteroarene$_{(C≤12)}$, heterocycloalkane$_{(C≤12)}$, or a substituted version of any of these groups; or R7 and R8 are taken together and for a heterocycloalkane$_{(C≤12)}$ or a substituted heterocycloalkane$_{(C≤12)}$ which is further optionally substituted with an oxo group, an acyloxy$_{(C≤8)}$ group, or a substituted acyloxy$_{(C≤8)}$ group;

or a pharmaceutically acceptable salt thereof.

In some embodiments, the SHP2 inhibitor is a compound described in Table 1 below. For example, it is anticipated that these specific compounds may be used to promote surface expression of IR, or treat a disease associated with insulin resistance or IR dysfunction, as described herein.

TABLE 1

SHP2 Inhibitors (1)

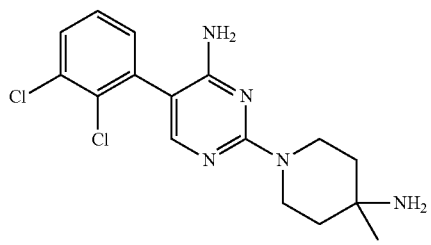 [SMILES: CC1(N)CCN(c2ncc(-c3cccc(Cl)c3Cl)c(N)n2)CC1]

(2)

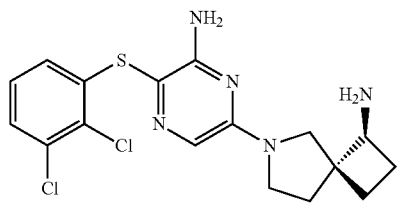 [SMILES: Nc1nc(N2CC[C@]3(CC[C@@H]3N)C2)cnc1Sc1cccc(Cl)c1Cl]

(3)

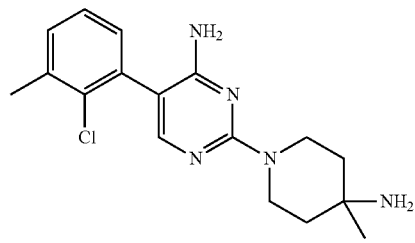 [SMILES: Cc1cccc(-c2cnc(N3CCC(C)(N)CC3)nc2N)c1Cl]

(4)

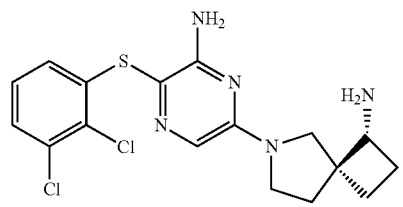 [SMILES: Nc1nc(N2CC[C@@]3(CC[C@H]3N)C2)cnc1Sc1cccc(Cl)c1Cl]

(5)

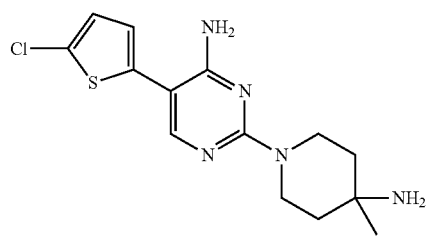 [SMILES: CC1(N)CCN(c2ncc(-c3ccc(Cl)s3)c(N)n2)CC1]

TABLE 1-continued

SHP2 Inhibitors (6)

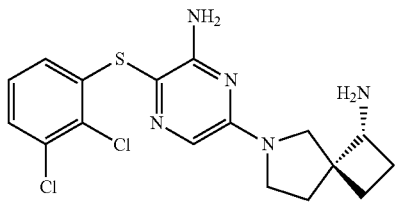 [SMILES: Nc1nc(N2CC[C@]3(CC[C@H]3N)C2)cnc1Sc1cccc(Cl)c1Cl]

(7)

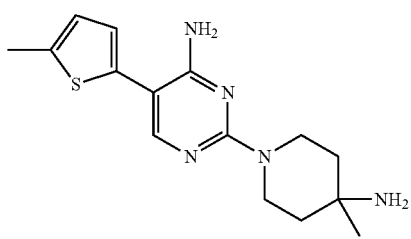 [SMILES: Cc1ccc(-c2cnc(N3CCC(C)(N)CC3)nc2N)s1]

(8)

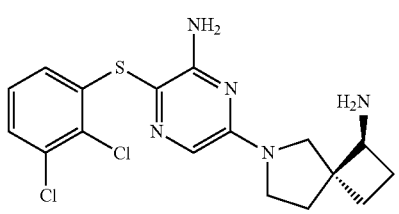 [SMILES: Nc1nc(N2CC[C@@]3(CC[C@@H]3N)C2)cnc1Sc1cccc(Cl)c1Cl]

(9)

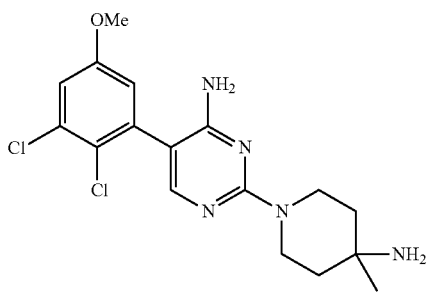 [SMILES: COc1cc(Cl)c(Cl)c(-c2cnc(N3CCC(C)(N)CC3)nc2N)c1]

(10)

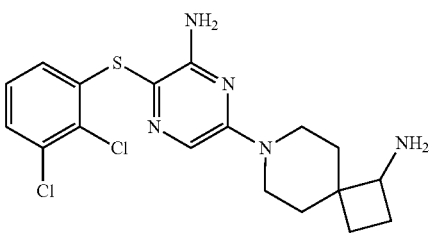 [SMILES: Nc1nc(N2CCC3(CCC3N)CC2)cnc1Sc1cccc(Cl)c1Cl]

(11)

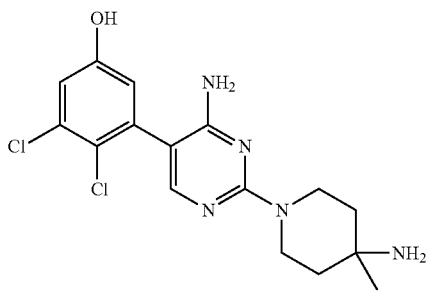 [SMILES: CC1(N)CCN(c2ncc(-c3cc(O)cc(Cl)c3Cl)c(N)n2)CC1]

TABLE 1-continued
SHP2 Inhibitors
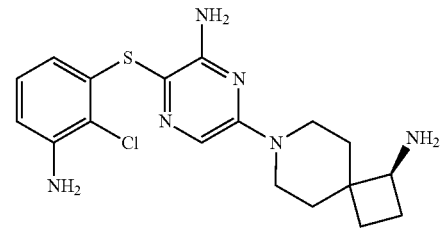 [SMILES: Nc1cccc(Sc2ncc(N3CCC4(CC[C@@H]4N)CC3)nc2N)c1Cl]
(12)
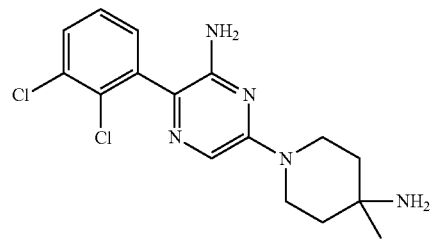 [SMILES: CC1(N)CCN(c2cnc(-c3cccc(Cl)c3Cl)c(N)n2)CC1]
(13)
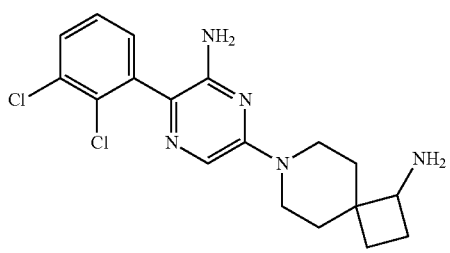 [SMILES: Nc1nc(N2CCC3(CCC3N)CC2)cnc1-c1cccc(Cl)c1Cl]
(14)
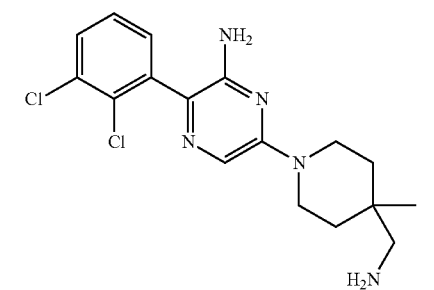 [SMILES: CC1(CN)CCN(c2cnc(-c3cccc(Cl)c3Cl)c(N)n2)CC1]
(15)
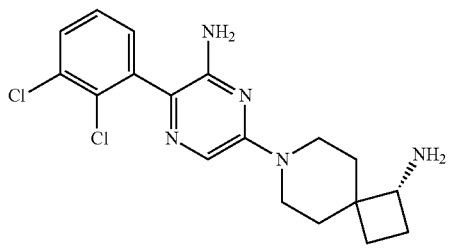 [SMILES: Nc1nc(N2CCC3(CC[C@H]3N)CC2)cnc1-c1cccc(Cl)c1Cl]
(16)
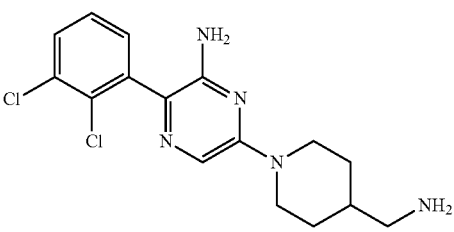 [SMILES: NCC1CCN(c2cnc(-c3cccc(Cl)c3Cl)c(N)n2)CC1]
(17)
TABLE 1-continued
SHP2 Inhibitors
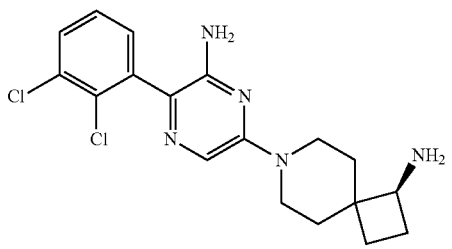 [SMILES: Nc1nc(N2CCC3(CC[C@@H]3N)CC2)cnc1-c1cccc(Cl)c1Cl]
(18)
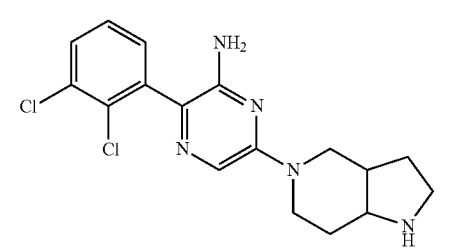 [SMILES: Nc1nc(N2CCC3NCCC3C2)cnc1-c1cccc(Cl)c1Cl]
(19)
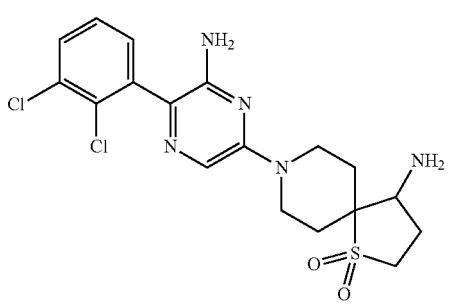 [SMILES: Nc1nc(N2CCC3(CC2)C(N)CCS3(=O)=O)cnc1-c1cccc(Cl)c1Cl]
(20)
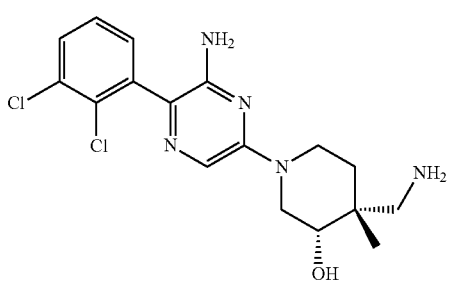 [SMILES: C[C@]1(CN)CCN(c2cnc(-c3cccc(Cl)c3Cl)c(N)n2)C[C@H]1O]
(21)
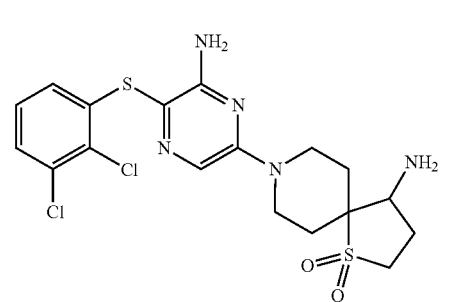 [SMILES: Nc1nc(N2CCC3(CC2)C(N)CCS3(=O)=O)cnc1Sc1cccc(Cl)c1Cl]
(22)

TABLE 1-continued

SHP2 Inhibitors (23)–(34): Chemical structures of SHP2 inhibitors.

TABLE 1-continued

SHP2 Inhibitors

(35) (36) (37) (38) (39) (40) (41) (42) (43) (44) (45)

TABLE 1-continued
SHP2 Inhibitors
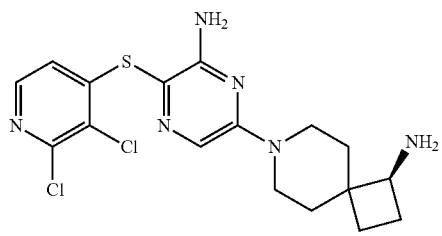 [SMILES: Nc1nc(N2CCC3(CC[C@@H]3N)CC2)cnc1Sc1ccnc(Cl)c1Cl] (46)
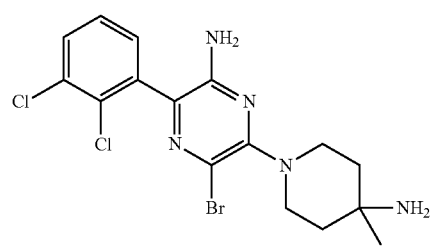 [SMILES: CC1(N)CCN(c2nc(N)c(-c3cccc(Cl)c3Cl)nc2Br)CC1] (47)
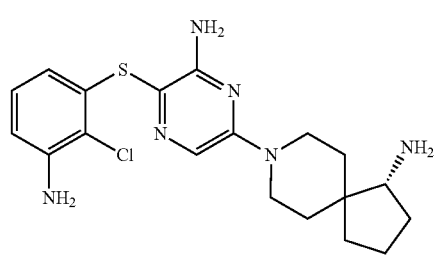 [SMILES: Nc1cccc(Sc2ncc(N3CCC4(CCC[C@H]4N)CC3)nc2N)c1Cl] (48)
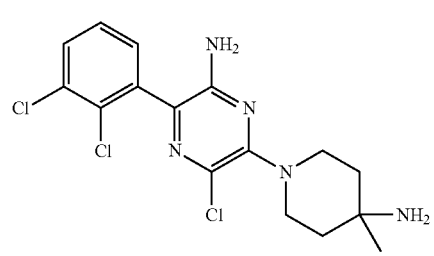 (49)
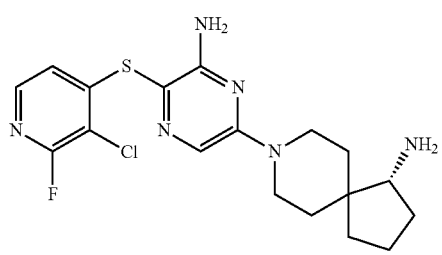 [SMILES: Nc1nc(N2CCC3(CCC[C@H]3N)CC2)cnc1Sc1ccnc(F)c1Cl] (50)
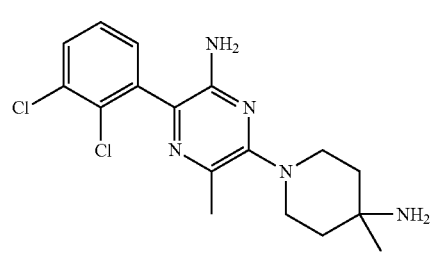 (51)
TABLE 1-continued
SHP2 Inhibitors
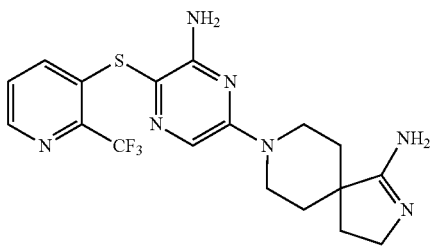 [SMILES: NC1=NCCC12CCN(c1cnc(Sc3cccnc3C(F)(F)F)c(N)n1)CC2] (52)
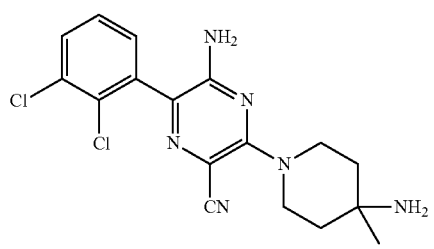 [SMILES: CC1(N)CCN(c2nc(N)c(-c3cccc(Cl)c3Cl)nc2C#N)CC1] (53)
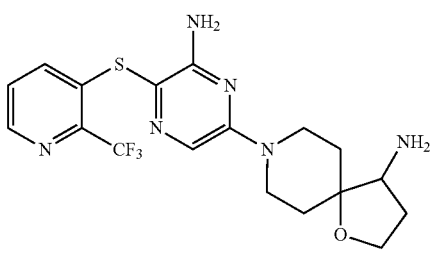 [SMILES: Nc1nc(N2CCC3(CC2)OCCC3N)cnc1Sc1cccnc1C(F)(F)F] (54)
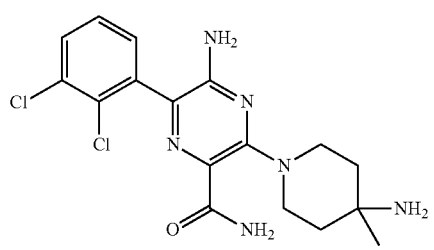 [SMILES: CC1(N)CCN(c2nc(N)c(-c3cccc(Cl)c3Cl)nc2C(N)=O)CC1] (55)
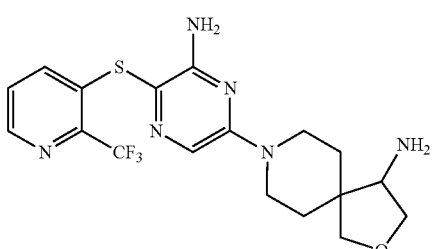 (56)
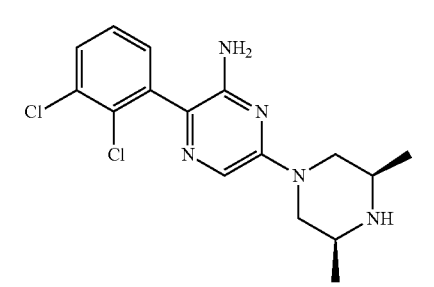 [SMILES: C[C@@H]1CN(c2cnc(-c3cccc(Cl)c3Cl)c(N)n2)C[C@H](C)N1] (57)

TABLE 1-continued

SHP2 Inhibitors

TABLE 1-continued

SHP2 Inhibitors

TABLE 1-continued

SHP2 Inhibitors

TABLE 1-continued
SHP2 Inhibitors
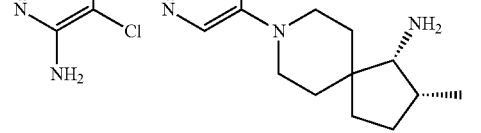
(92)
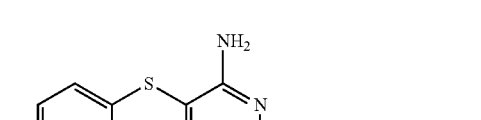
(93)
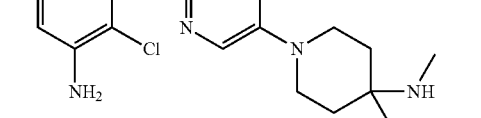
(94)
(95)
(96)
(97)
TABLE 1-continued
SHP2 Inhibitors
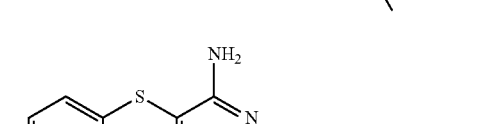
(98)
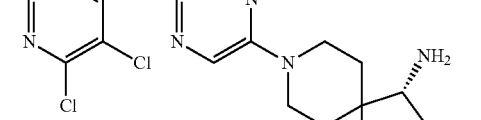
(99)
(100)
(101)
(102)
(103)

TABLE 1-continued

SHP2 Inhibitors (104), (105), (106), (107), (108), (109), (110), (111), (112), (113), (114)

TABLE 1-continued
SHP2 Inhibitors
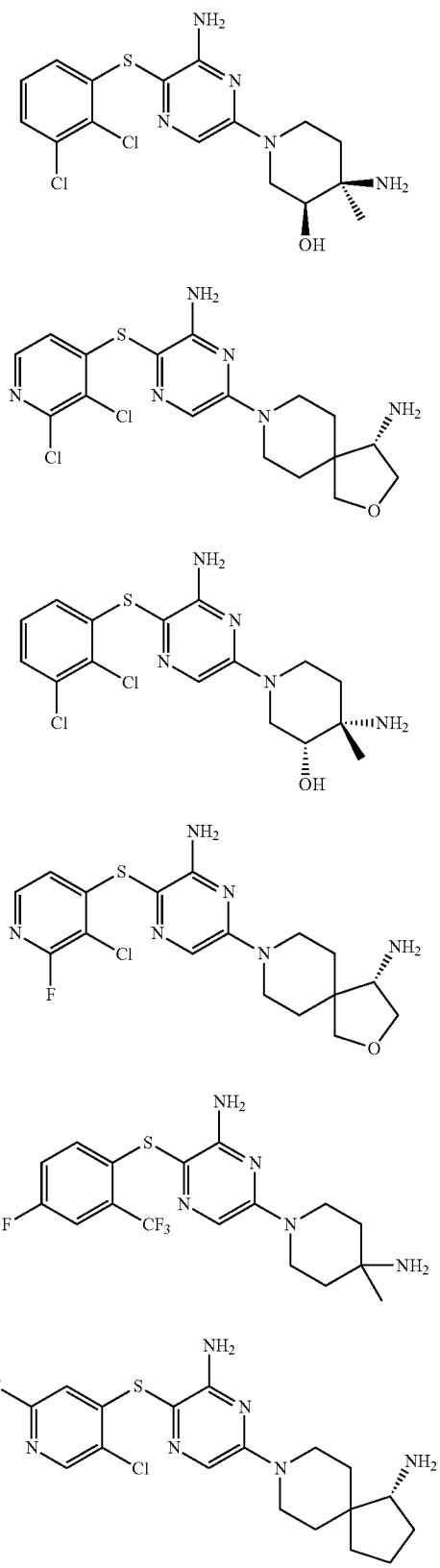
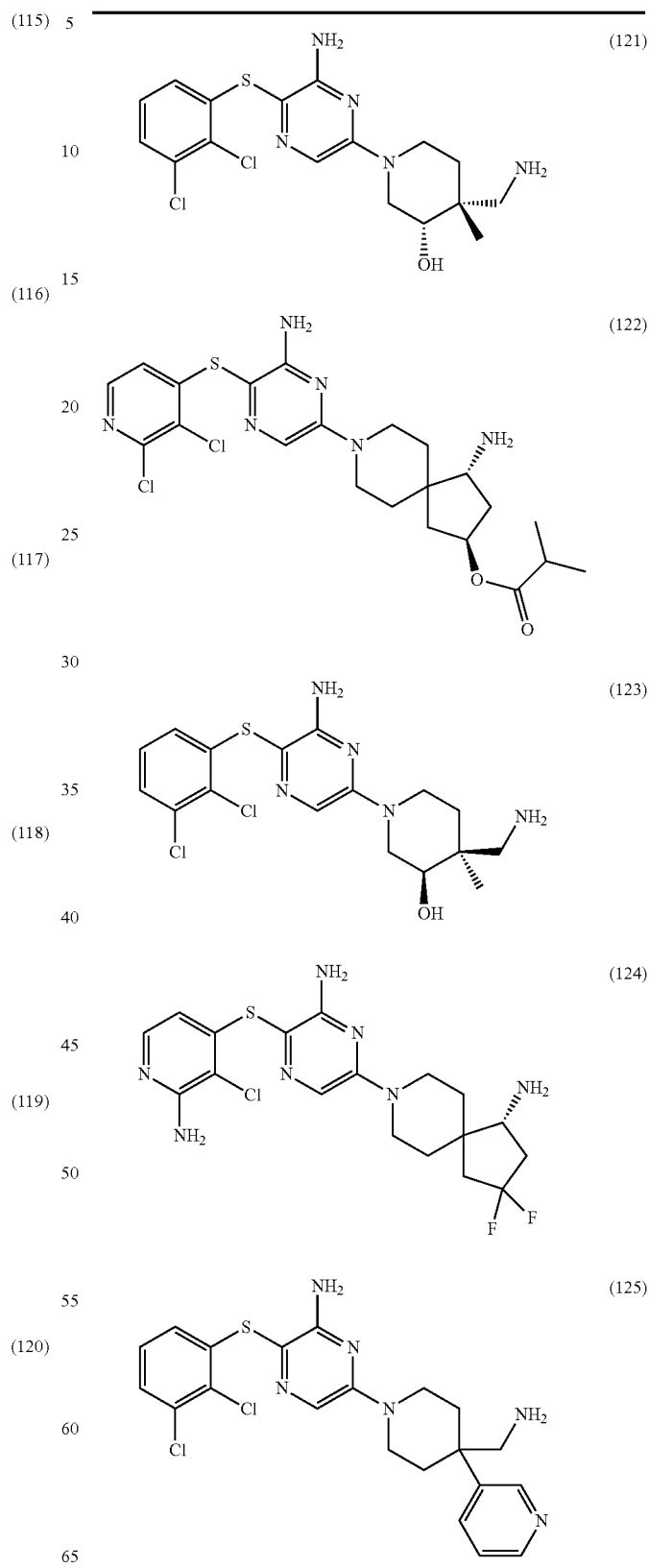

TABLE 1-continued

SHP2 Inhibitors

TABLE 1-continued
SHP2 Inhibitors
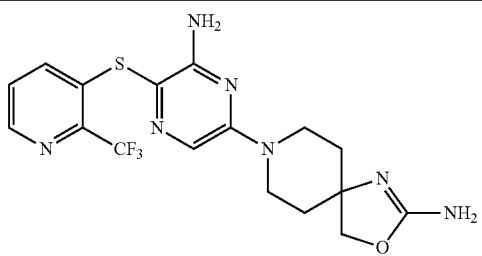 (138)
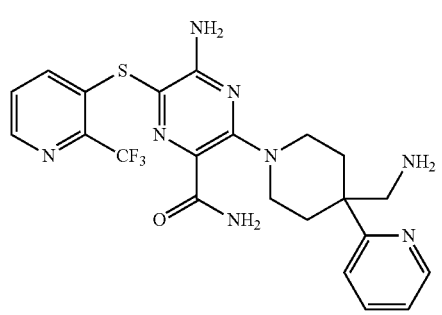 [SMILES: NCC1(c2ccccn2)CCN(c2nc(N)c(Sc3cccnc3C(F)(F)F)nc2C(N)=O)CC1] (139)
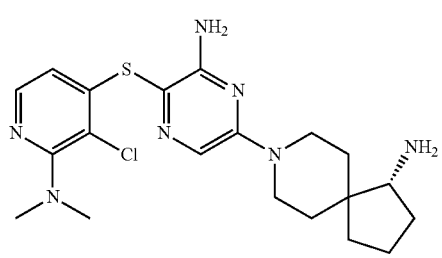 [SMILES: CN(C)c1nccc(Sc2ncc(N3CCC4(CCC[C@H]4N)CC3)nc2N)c1Cl] (140)
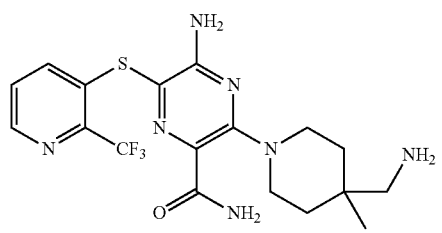 [SMILES: CC1(CN)CCN(c2nc(N)c(Sc3cccnc3C(F)(F)F)nc2C(N)=O)CC1] (141)
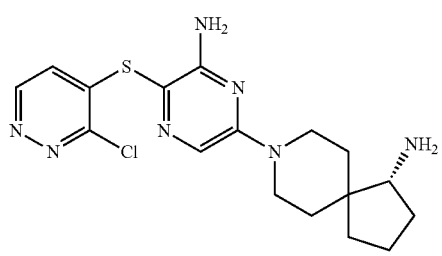 [SMILES: Nc1nc(N2CCC3(CCC[C@H]3N)CC2)cnc1Sc1ccnnc1Cl] (142)
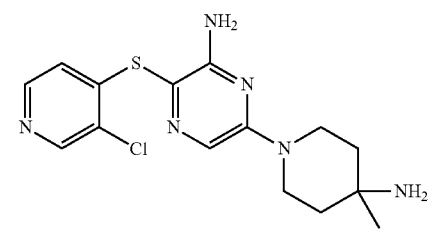 [SMILES: CC1(N)CCN(c2cnc(Sc3ccncc3Cl)c(N)n2)CC1] (143)
TABLE 1-continued
SHP2 Inhibitors
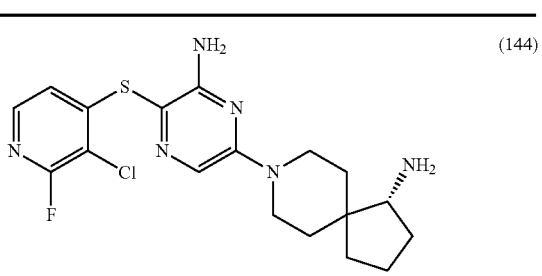 (144)
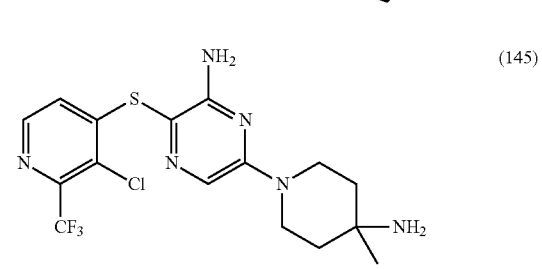 (145)
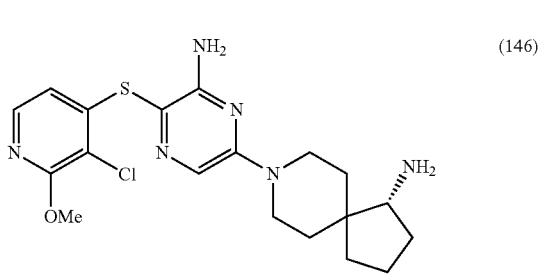 (146)
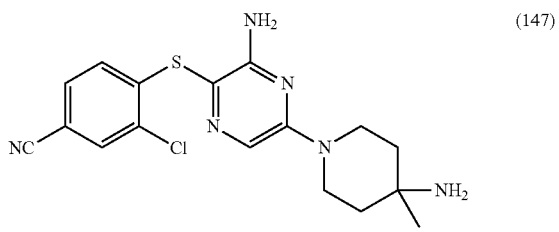 (147)
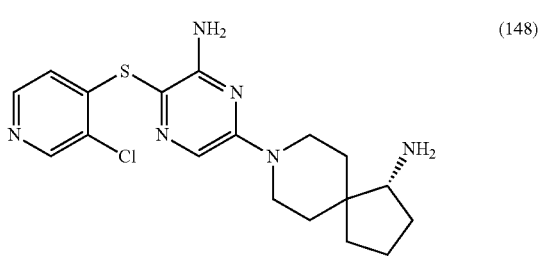 (148)
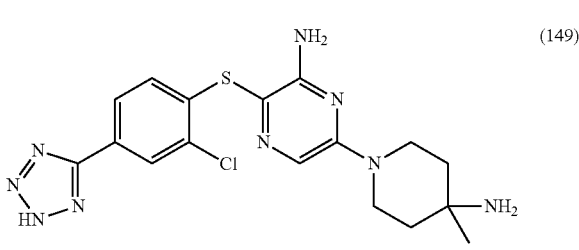 (149)

TABLE 1-continued
SHP2 Inhibitors
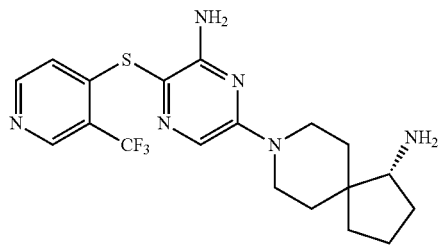 [SMILES: Nc1nc(N2CCC3(CCC[C@H]3N)CC2)cnc1Sc1ccncc1Cl] (150)
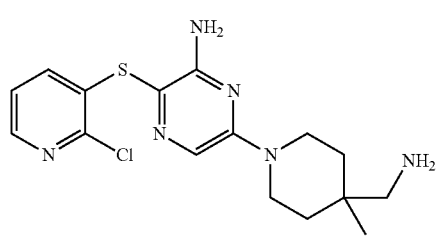 [SMILES: CC1(CN)CCN(c2cnc(Sc3cccnc3Cl)c(N)n2)CC1] (151)
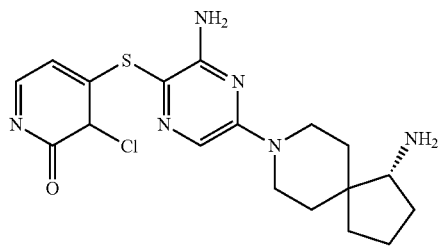 [SMILES: Nc1nc(N2CCC3(CCC[C@H]3N)CC2)cnc1SC1=CC=NC(=O)C1Cl] (152)
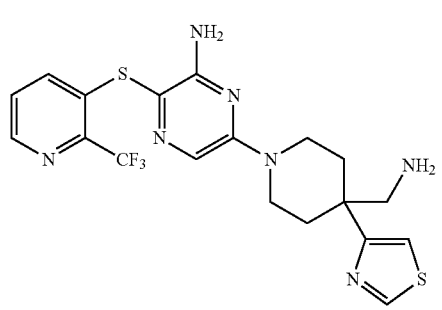 [SMILES: NCC1(c2cscn2)CCN(c2cnc(Sc3cccnc3C(F)(F)F)c(N)n2)CC1] (153)
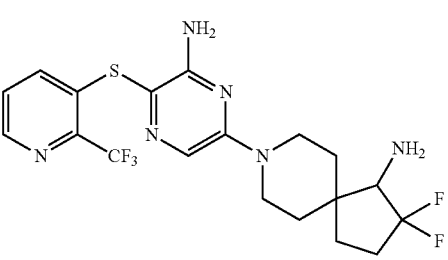 (154)
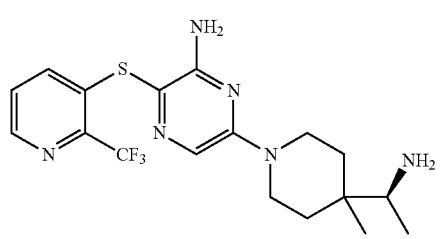 [SMILES: C[C@H](N)C1(C)CCN(c2cnc(Sc3cccnc3C(F)(F)F)c(N)n2)CC1] (155)
TABLE 1-continued
SHP2 Inhibitors
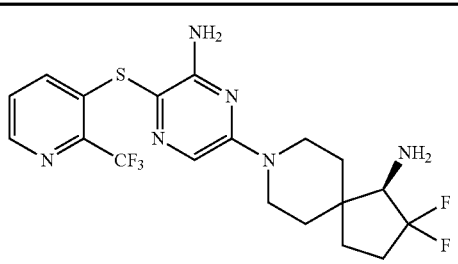 (156)
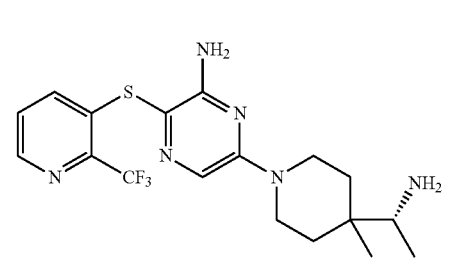 [SMILES: C[C@@H](N)C1(C)CCN(c2cnc(Sc3cccnc3C(F)(F)F)c(N)n2)CC1] (157)
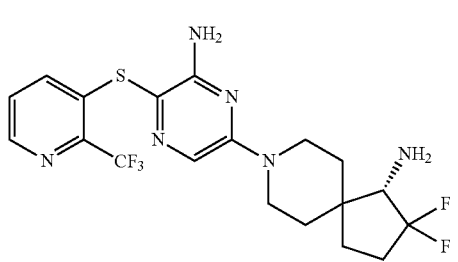 (158)
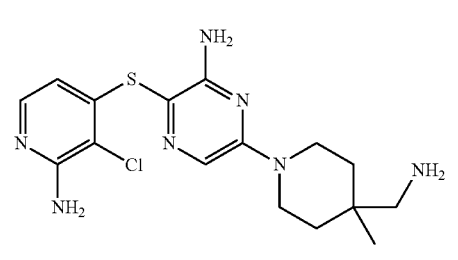 (159)
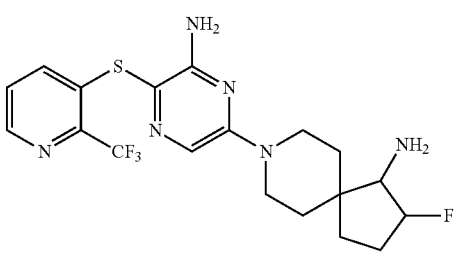 [SMILES: Nc1nc(N2CCC3(CCC(F)C3N)CC2)cnc1Sc1cccnc1C(F)(F)F] (160)
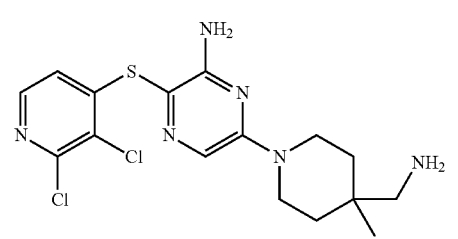 [SMILES: CC1(CN)CCN(c2cnc(Sc3ccnc(Cl)c3Cl)c(N)n2)CC1] (161)

TABLE 1-continued
SHP2 Inhibitors
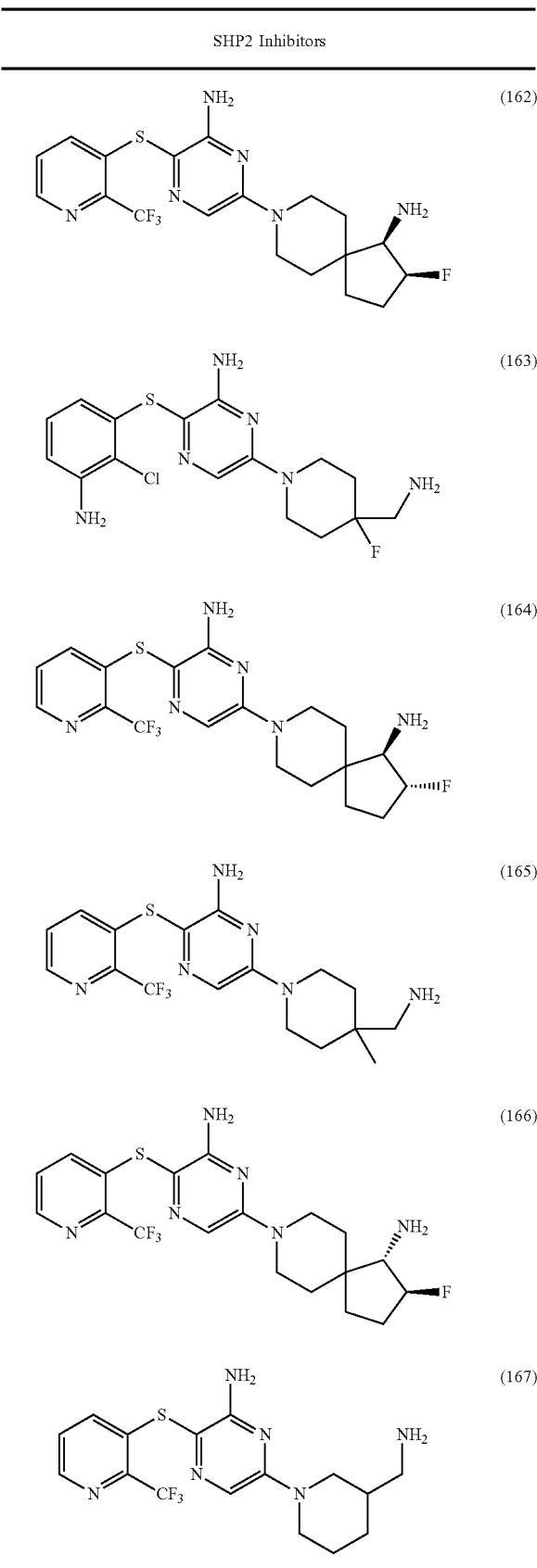
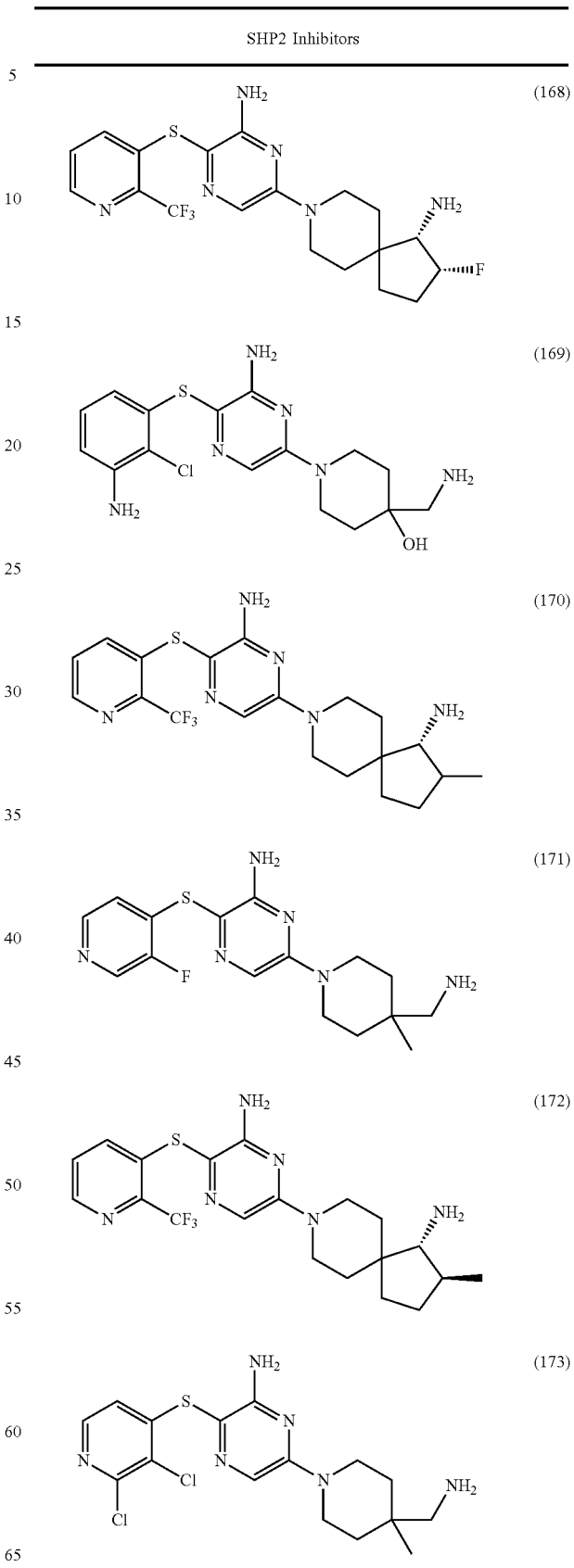

TABLE 1-continued

SHP2 Inhibitors (174) – (185): chemical structures of SHP2 inhibitors.

TABLE 1-continued
SHP2 Inhibitors
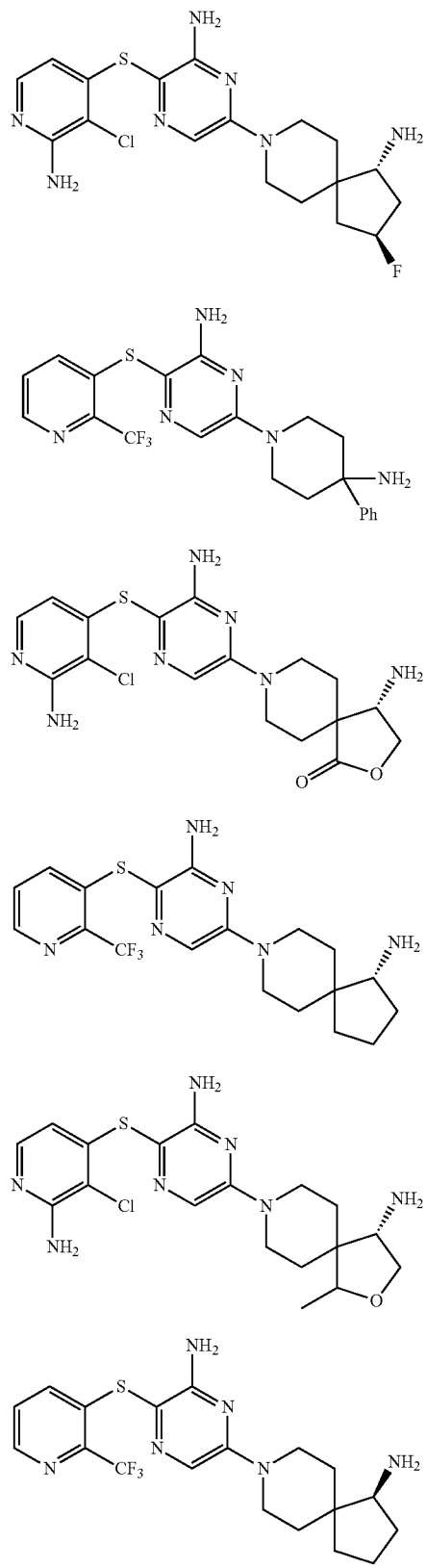
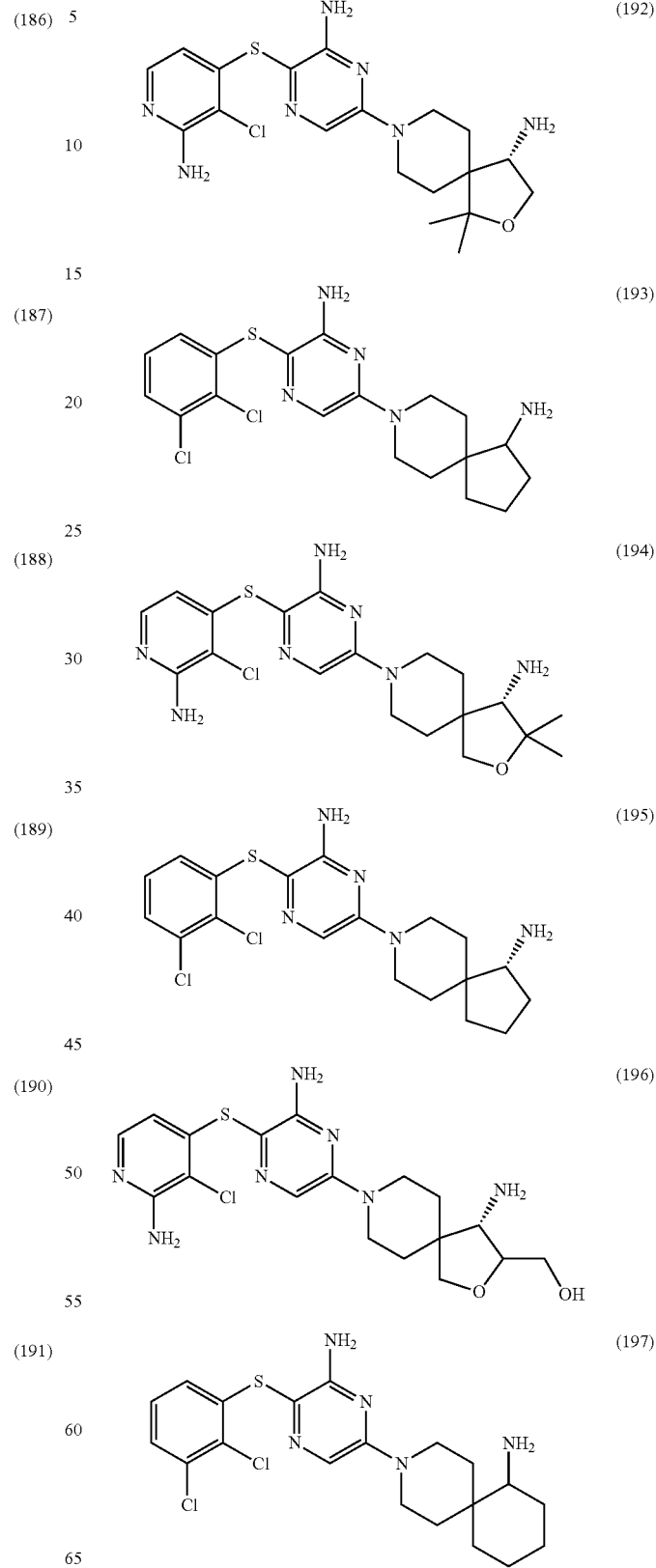

TABLE 1-continued
SHP2 Inhibitors
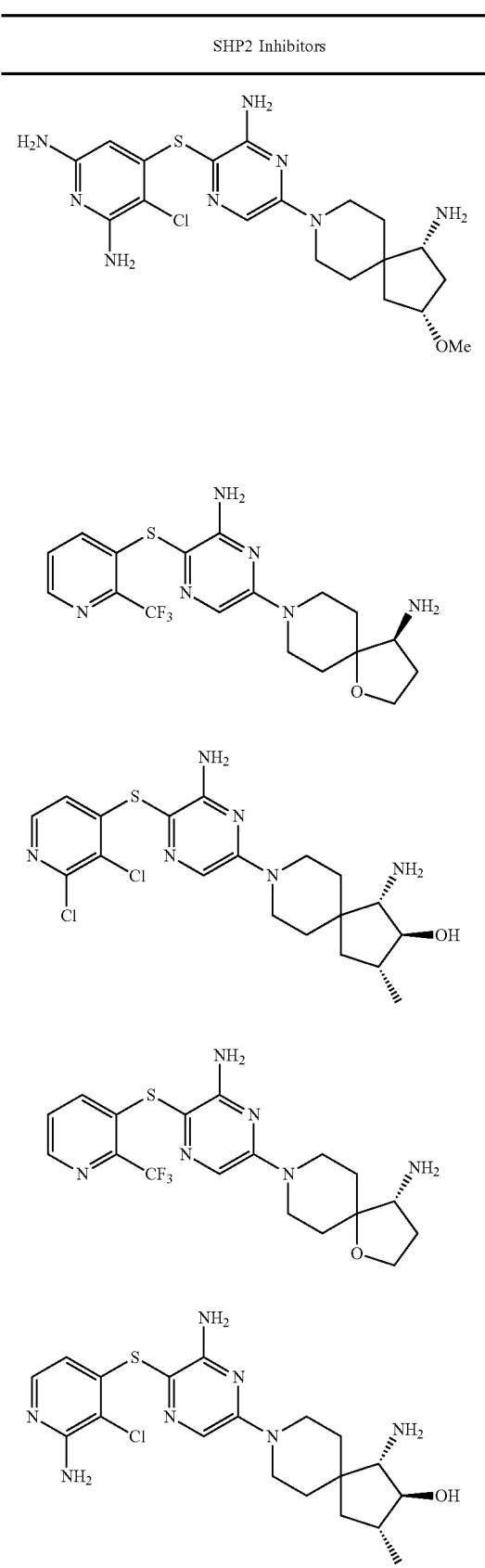
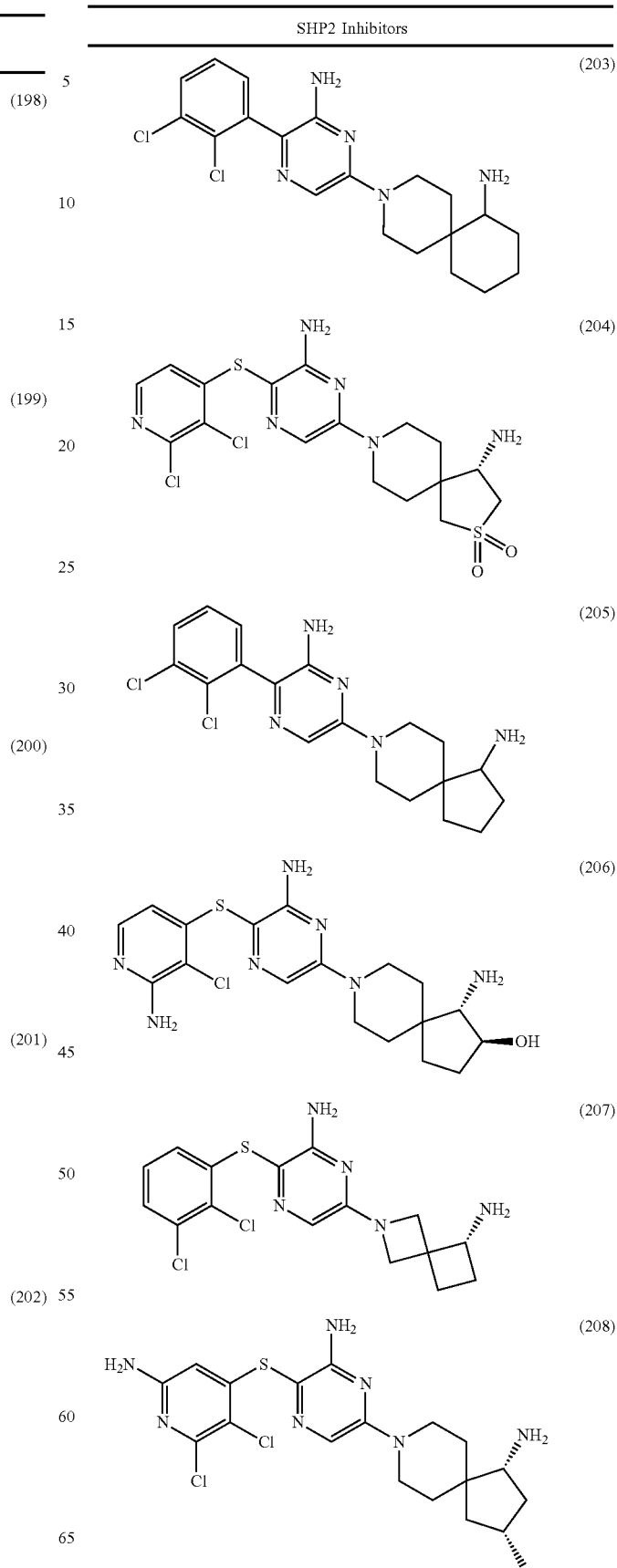

TABLE 1-continued

SHP2 Inhibitors (209)

(210)

(211)

(212)

(213)

(214)

(215)

(216)

(217)

(218)

The compounds of the present invention (also referred to as "compounds of the present disclosure") are shown, for example, above, in the summary of the invention section, and in the claims below. They may be made using the synthetic methods outlined in the references cited herein such as US20170015680, US20170001975, and US20170204080. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch of continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All of the compounds of the present invention may be useful for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all of the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "-" means a single bond, "=" means a double bond, and "≡" means triple bond. The symbol "----" represents an optional bond, which if present is either single or double. The symbol ==== represents a single bond or a double bond. Thus, the formula

covers, for example,

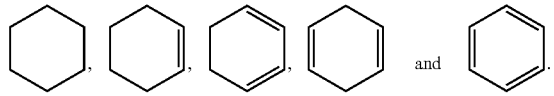

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "〜〜〜", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◥◣" means a single bond where the group attached to the thick end of the wedge is "out of the page." The symbol "⦀⦀⦀⦀" means a single bond where the group attached to the thick end of the wedge is "into the page". The symbol "∽∽∽" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

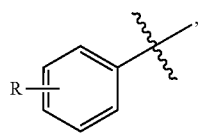

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

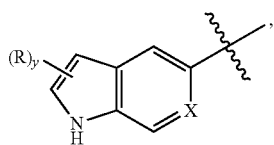

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "alkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

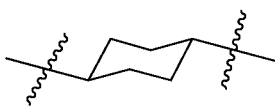 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "cycloalkenyl" when used without the "substituted" modifier refers to a monovalent saturated aliphatic group with a carbon atom as the point of attachment, said carbon atom forming part of one or more non-aromatic ring structures, one or more carbon-carbon double bonds provided that the group remains non-aromatic, no carbon-carbon triple bonds, and no atoms other than carbon and hydrogen. Non-limiting examples include: cyclopentenyl or cyclohexdienyl. As used herein, the term does not preclude the presence of one or more alkyl groups (carbon number limitation permitting) attached to a carbon atom of the non-aromatic ring structure. The term "cycloalkenediyl" when used without the "substituted" modifier refers to a divalent saturated aliphatic group with two carbon atoms as points of attachment, one or more carbon-carbon double bonds provided that the group remains non-aromatic, no carbon-carbon triple bonds, and no atoms other than carbon and hydrogen. A "cycloalkene" refers to the class of compounds having the formula H—R, wherein R is cycloalkenyl as this term is defined above. When any of these terms is used with the "substituted" modifier, one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

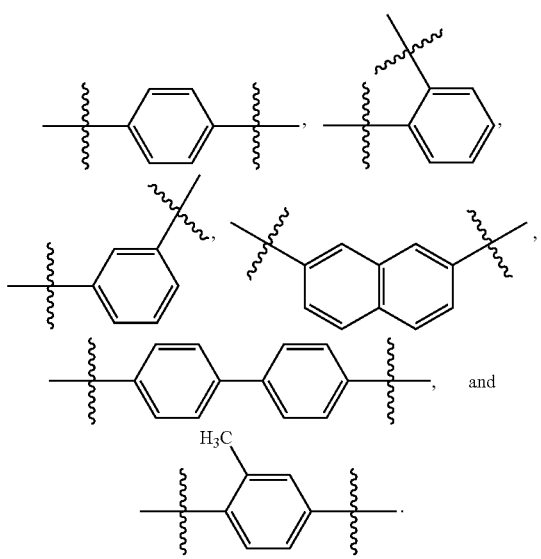

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. Additionally, the sulfur atom, if it is a part of the ring structures, may be oxidized to obtain a sulfinyl or sulfonyl group. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier, one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, apes, horse, cow, sheep, goat, swine, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids such as acetate, valerate, oleate, palmitate, stearate, or laurate, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical agent, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. SHP2 Nucleic Acid Inhibitors

Inhibitory nucleic acids that inhibit the transcription or translation of SHP2 may be used in various embodiments to treat an IR disease or disorder as described herein. An inhibitory nucleic acid can inhibit the transcription of a gene or prevent the translation of a gene transcript in a cell. In some embodiments, the inhibitory nucleic acid may be from 19-29, or 19, 20, 21, 22, 23, 24, 25, 26, 27, 28 or 29 nucleotides long, or any range derivable therein. In some embodiments, the inhibitory nucleic acid is a siRNA or an RNAi that selectively decreases expression of SHP2. For example, in some embodiments, the inhibitory nucleic acid is a siRNA that is 21 nucleotides in length.

Methods for the generation of inhibitory nucleic acids, such as siRNA, are well known in the art. Inhibitory nucleic acids are well known in the art. For example, siRNA, shRNA and double-stranded RNA have been described, e.g., in U.S. Pat. Nos. 6,506,559 and 6,573,099, as well as in U.S. Patent Publication Nos. 2003/0051263, 2003/0055020, 2004/0265839, 2002/0168707, 2003/0159161, and 2004/0064842, all of which are herein incorporated by reference in their entirety.

In designing an RNAi, several factors should be considered, including the nature of the siRNA, the durability of the silencing effect, and the choice of delivery system. To produce an RNAi effect, the RNA siRNA that is introduced into the organism will typically contain an exonic sequence. Furthermore, the RNAi process is homology dependent, so the sequences must be carefully selected so as to maximize gene specificity, while minimizing the possibility of cross-interference between homologous, but not gene-specific sequences. Particularly the siRNA exhibits greater than 80, 85, 90, 95, 98% or preferably 100% identity or complementarity between the sequence of the siRNA and a portion of a RNA sequence encoding SHP2. Sequences less than about 80% identical to the target gene are substantially less effective. Thus, the greater identity between the siRNA and the SHP2 gene to be inhibited, the less likely expression of unrelated genes will be affected.

In addition, the size of the siRNA is an important consideration. For example, siRNA molecules for the inhibition of SHP2 may be between about 19-25 nucleotides (e.g., 19, 20, 21, 22, 23, 24, or 25). In some embodiments the siRNA is a longer RNA (e.g., 40-70 nucleotides, or any range therein) that can form a hairpin structure that can self-hybridize, wherein the RNA can form a double-stranded RNA structure 19-25 nucleotides, or any range therein, in length. For example, the siRNA may contain 19-25 contiguous nucleotides on each side or the siRNA that can hybridize and are separated by loop region. Various siRNA loop sequences (e.g., CTGGAG) are well known in the art and may be included in a siRNA that self-hybridizes.

The sequence of the siRNA molecules is important for the inhibition of gene expression. Examples of siRNA that may be used to inhibit SHP2 include, e.g., the sense sequence: AAGAAUCCUAUGGUGGAAACA-dTdT (SEQ ID NO: 1) or the antisense sequence: UGUUUCCACCAUAG-GAUUCUU-dTdT (SEQ ID NO:2).

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus can been used (Wadhwa et al., 2004).

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid forms a double-stranded structure; the double-stranded structure may result from two separate nucleic acids that are partially or completely complementary. In certain embodiments, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 19-29 or more contiguous nucleobases, including all ranges there between. The inhibitory nucleic acid may comprise, e.g., 19-25 contiguous nucleobases that hybridize with a complementary nucleic acid (which may be another part of the same nucleic acid or a separate complementary nucleic acid) to form a double-stranded structure.

siRNA can be obtained from commercial sources, natural sources, or can be synthesized using any of a number of techniques well-known to those of ordinary skill in the art. For example, commercial sources of predesigned siRNA include Invitrogen's Stealth™ Select technology (Carlsbad, Calif.), Ambion® (Austin, Tex.), Dharmacon (Lafayette, Colo.), and Qiagen® (Valencia, Calif.). An inhibitory nucleic acid that can be applied in the compositions and methods of the present invention may be any nucleic acid sequence that has been found by any source to be a validated downregulator of a SHP2.

In some embodiments, the siRNA molecule is at least 90% homologous, particularly at least 95%, 99%, or 100% similar or identical, or any percentages in between the foregoing, and said ranges are intended to include all whole numbers in between), to at least 10 contiguous nucleotides of any of the nucleic acid sequences encoding a full-length SHP2 protein. Preferably, the siRNA molecule is identical to 21-25 nucleotides of an RNA encoding SHP2.

The siRNA may also comprise an alteration or chemical modification of one or more nucleotides. Such alterations can include the addition of non-nucleotide material, such as to the end(s) of the siRNA or internally (at one or more nucleotides of the RNA). In certain aspects, the RNA molecule contains a 3'-hydroxyl group. Nucleotides in the RNA molecules described herein can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified siRNAs.

III. Insulin Receptor Diseases and Insulin Resistance

The insulin receptor (IR) is the transmembrane receptor for insulin, insulin like growth factor-1, and insulin-like growth factor-2, and is well known to play an important role in glucose homeostasis. IR is encoded by a single gene, INSR, and transcripts can undergo alternative splicing, resulting in two different isoforms: INSR-A and INSR-B. Mutations in the INSR gene can result in a variety of diseases, including diabetes, Donohue syndrome, and Rabson-Mendenhall syndrome. In some embodiments, patients with a genetic defect in the INSR gene may be treated with a SHP2 inhibitor. In some instances, patients with an insulin resistance disorder may have a mutation in any of a variety of genes including, but not limited to, PTPN11, INSR, RAS, RAF, ERK1/2, IRS1/2, MAD2L1BP, BUB1B, or MAD2.

In some embodiments, subjects that have both (i) an insulin resistance disorder or an IR disease (e.g., type 2 diabetes, a monogenic disease affecting β-cell function, a genetic IR disease, type A insulin resistance, Donohue syndrome, Rabson-Mendenhall syndrome) and (ii) a cancer, may be treated with a SHP2 inhibitor (e.g., an allosteric inhibitor of SHP2 or an inhibitory RNA as described herein). In some embodiments, the cancer may have a mutation in the INSR gene and/or in the PTPN11 gene. In some embodiments, the cancer is Juvenile Myelomonocytic Leukemia (JMML), acute myeloid leukemia (AML), MDS, B cell acute lymphoblastic leukemia (B-ALL), neuroblastoma, esophageal cancer, breast cancer, lung cancer, colon cancer, gastric cancer, head and neck cancer, liver cancer, or pancreatic cancer.

A. Type 2 Diabetes

In some embodiments, a SHP2 inhibitor is administered to a subject to treat type 2 diabetes. Type 2 diabetes is characterized by high blood sugar and, frequently, insulin resistance. Several genes have been associated with increased risk of type 2 diabetes, including TCF7L2, ABCC8, CAPN10, GLUT2, and GCGR. Type 2 diabetes treatments that may be administered in combination with a SHP2 inhibitor include, e.g., metformin, sulfonylureas, meglitinides, DPP-4 inhibitors, GLP-1 receptor agonists, SGLT2 inhibitors, and insulin therapy.

B. Monogenic Diseases Affecting β-Cell Function

In some instances, it may be possible to alleviate one or more symptom in a subject associated with a genetic disease that adversely affects β-cell function by administering SHP2 inhibitor. Genetic defects affecting β-cell function include mutations on chromosome 12 in the HNF-1α (formerly MODY3) gene, chromosome 7 in the GCK gene (formerly MODY2) gene, chromosome 20 in the HNF-4α (formerly MODY1) gene, or in mitochondrial DNA. These mutations have been found to be the primary cause of maturity onset diabetes in young patients. For example, if a patient is heterozygous for a mutation affecting B-cell function, then strengthening IR signaling via administration of a SHP2 inhibitor may provide a therapeutic benefit.

C. Genetic Insulin Receptor Diseases

In some embodiments, a SHP2 inhibitor as described herein can be administered to a subject to treat a disease resulting from a IR mutation. Mutations in the insulin receptor gene, INSR, can result in a variety of diseases ranging from type A insulin resistance syndrome to more severe diseases including Rabson-Mendenhall syndrome and Donohue syndrome. These diseases are generally characterized by the body's failure to respond to the hormone insulin, resulting in very high blood sugar. Examples of mutations in the INSR gene that can result in a disease that may be treated in various embodiments are provided below in Table 2.

TABLE 2

Characterization of IR mutations found in human patients

| Class | Mutation | Localization* | Kinase** | Level** | Phenotype |
|---|---|---|---|---|---|
| I | P997T | PM | Active | +++ | Rabson-Mendenhall syndrome |
| | V1012M | PM | NT | NT | Type 2 diabetes |
| | A1055V | PM | Weak | +++ | Insulin resistance |
| | K1095E | PM | NT | NT | Type 2 diabetes |
| | R1119Q | PM | NT | NT | Leprechaunism |
| | H1157R | PM | ND | ++ | Insulin resistance |
| | R1191Q | PM | NT | NT | Type 2 diabetes |
| | Y1361C | PM | NT | NT | Type 2 diabetes |
| | R1378Q | PM | Active | +++ | Insulin resistance |
| II | R1020Q | IC | Active | +++ | Insulin resistance |
| | V1054M | IC | Active | + | Leprechaunism |
| | A1075D | IC | Active | + | Insulin resistance |
| | V1086E | IC | Active | + | Type 2 diabetes |
| | I1143T | IC | Active | ++ | Rabson-Mendenhall syndrome |
| III | A1162E | ER/Golgi | NT | NT | Insulin resistance |
| | W1220L | ER/Golgi | ND | + | Insulin resistance |

*The cellular localization of IR-GFP in the basal, unstimulated state. PM, plasma membrane; IC, intracellular compartment; ER/Golgi, endoplasmic reticulum/Golgi apparatus.
**To determine the kinase activities and levels of mature IRβ proteins, HepG2 cell lines stably expressing IR-GFP mutants were serum starved for 14 h and treated without or with 100 nM insulin for 5 min. Total cell lysates were blotted with anti-IR, anti-IR pY1189/1190, and anti-ACTIN antibodies. The relative levels of total IRβ-GFP proteins and their autophosphorylation were compared with those of endogenous IR.
NT, not tested;
ND, not detected.

1. Type A Insulin Resistance

The mutations in the INSR gene that cause type A insulin resistance result in the production of insulin receptors that are unable to transmit signals properly, regardless of the amount of the insulin receptor present or its level of autophosphorylation. Subjects with type A insulin resistance typically experience dysregulation of blood sugar levels and eventually develop diabetes mellitus.

2. Donohue Syndrome

Donohue syndrome, also known as Leprechaunism, is a genetic disease that results from homozygous mutations in the INSR gene. Nucleotide mutations in the INSR gene which result in Donohue syndrome include: c.126C>A, c.164T>C, c.172G>A, c.338G>C, c.356C>T, c.425G>T, c.442A>T, c.451G>T, c.659C>T, c.707A>G, c.895C>T, c.902G>A, c.1177G>A, c.1246C>T, c.1316G>C, c.1459A>G, c.1975T>C, c.2095C>T, c.2201A>C, c.2437C>T, c.2453A>C, c.2621C>T, c.2668C>T, c.2770C>T, c.2774T>C, c.2776C>T, c.2810C>T, c.2971C>A, c.3160G>A, c.3356G>A, c.3355C>T, c.3601C>T, and c.3616G>A (Ardon et al., 2014). Other splice site, insertion/deletion, and arrangement mutations in the INSR gene can also result in Donohue syndrome, including: change of splice site at G2682A, change of splice site at G3794T, deletion of the A at base 404, deletion of bases 444-446, deletion of bases 927-929, deletion of bases 1084-1086, deletion of bases 1998-2001, deletions of bases 2944-2945, deletion of G 3048, single G insertion between 2050-2051, single A insertion between 2125-2126, a >12 kb deletion including exons 10-13, deletion of the entire gene, deletion of 2630-2642 with a 5 base insertion. Donohue syndrome is the most severe of the diseases associated with mutations in INSR, and those born with Donohue syndrome typically do not live longer than one year following birth (Longo et al., 2002).

3. Rabson-Mendenhall Syndrome

Rabson-Mendenhall syndrome is another genetic disease that results from mutations in the INSR gene. The mutations associated with Rabson-Mendenhall syndrome are typically homozygous nonsense or missense mutations in the INSR gene, though splice variants have also been described. Previously reported nucleotide changes in the INSR gene which result in Rabson-Mendenhall syndrome include: c.90C>A, c.121C>T, c.557G>T, c.712G>A, c.766C>T, c.932G>A, c.1156G>A, c.2621C>T, c.2989C>A, c.3220G>C, c.3428T>C, c.3472C>T (Ardon et al., 2014). Mutations which alter splicing include: c.1268+2T>C, and a 12 base insertion between nucleotides 866 and 867 (Ardon et al., 2014). Most of these of mutations result in changes in amino acids located on the intracellular domain of the protein (Longo et al., 2002).

4. Other Genetic Diseases

In some embodiments, a SHP2 inhibitor as described herein may be administered to treat a patient with Noonan syndrome. Noonan syndrome is one of the most common autosomal dominant developmental disorders (Keilhack et al., 2005; Fragale et al., 2004; Araki et al., 2009; Krenz, et al., 2008; Nakamura et al., 2009; Binder et al., 2005; Limal et al., 2006). About half of patient with Noonan syndrome carry a mutation in the PTPN11 gene (SHP2), resulting in hyperactivation of SHP2 catalytic activity.

Systemic lupus erythematousus (SLE) is an autoimmune disease in which the body's immune system actively attacks healthy tissue in many parts of the body (Wang et al., 2016). In some embodiments, a SHP2 inhibitor as described herein may be administered to treat a patient with SLE.

IV. Pharmaceutical Compositions

In some embodiments, there are provided pharmaceutically acceptable compositions which comprise a therapeutically-effective amount of a SHP2 inhibitor as described herein, a SHP2 antibody, and/or a RNAi or siRNA directed to SHP2, formulated together with one or more pharmaceutically acceptable carriers (additives) and/or diluents. As described in detail below, the pharmaceutical compositions may be specially formulated for administration in solid or liquid form, for administration by any means known in the art.

The phrase "therapeutically-effective amount" as used herein means that amount of a compound, material, or composition comprising a SHP2 inhibitor (e.g. an allosteric inhibitor of SHP2, a SHP2 antibody, or an inhibitory nucleic acid targeted to SHP2) which is effective for producing some desired therapeutic effect in at least a sub-population of cells in an animal at a reasonable benefit/risk ratio applicable to any medical treatment.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In some aspects, a SHP2 inhibitor may be formulated for oral or parenteral administration, such as by injection. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a SHP2 inhibitor (e.g. an allosteric inhibitor of SHP2, a SHP2 antibody, or an inhibitor nucleic acid targeted to SHP2). In certain embodiments, an aforementioned formulation renders orally bioavailable a SHP2 inhibitor.

Methods of preparing these formulations or compositions include the step of bringing into association a SHP2 inhibitor of the present invention with the carrier and, optionally, one or more accessory ingredients. In general, the formulations are prepared by uniformly and intimately bringing into association a SHP2 inhibitor with liquid carriers, or finely divided solid carriers, or both, and then, if necessary, shaping the product.

Formulations suitable for oral administration may be in the form of boluses, capsules, cachets, drenches, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a SHP2 inhibitor as an active ingredient.

In solid dosage forms for oral administration (capsules, tablets, pills, dragees, powders, granules, trouches and the like), a SHP2 inhibitor is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of SHP2 inhibitors, such as capsules, pills, dragees, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of SHP2 inhibitors include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of SHP2 inhibitors suitable for parenteral administration, such as subcutaneous, intramuscular, or intravenous injection, comprise one or more SHP2 inhibitors of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. Additionally, other antimicrobial agents such as penicillins, cephalosporins, aminoglycosides and glycopeptides may be added. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention (e.g., containing an allosteric SHP2 inhibitor) may be given orally or parenterally. They are of course given in forms suitable for each administration route. For example, they are administered in tablets or capsule form, by injection or infusion. Oral administrations are preferred. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally and parenterally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the SHP2 inhibitors in the pharmaceutical compositions of this invention may be varied so as to obtain an amount of the active ingredient which is effective to achieve the desired therapeutic response or therapeutic effect for a particular patient, composition, and mode of administration, without being toxic to the patient.

The selected dosage level will depend upon a variety of factors including the activity of the particular SHP2 inhibitor employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In some aspects, a SHP2 inhibitor can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutic effects of the first administered one is not entirely disappeared when the subsequent is administered.

Microemulsification technology can improve bioavailability of some lipophilic (water insoluble) pharmaceutical agents. Examples include Trimetrine (Dordunoo et al., 1991) and REV 5901 (Sheen et al., 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize SHP2 inhibitors and microemulsify them at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of $C_{1-6}$ to $C_{1-20}$. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use with SHP2 inhibitors are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 Daltons up to about 5,000 or 10,000 Daltons, and more preferably from about 300 Daltons to about 5,000 Daltons. In a particularly preferred embodiment, the polymer is polyethyleneglycol having a molecular weight of from about 100 to about 5,000 Daltons, and more preferably having a molecular weight of from about 300 to about 5,000 Daltons. Polymers may also be defined by the number of monomers therein; in some embodiments, polymers of at least about three monomers, such PEG polymers consisting of three monomers (approximately 150 Daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation comprising a SHP2 inhibitor comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The release characteristics of a formulation a SHP2 inhibitor depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. Other agents which alter the resident time of the composition include mucosal adhesive polymer, such as chitosan, celluloses, and especially polyacrylates (as used herein, polyacrylates refers to polymers including acrylate groups and modified acrylate groups such as cyanoacrylates and methacrylates).

A. Liposomes or Nanoparticles

In some embodiments, the SHP2 inhibitor (e.g., the allosteric SHP2 inhibitor, or the SHP2 siRNA or RNAi) may be associated with a lipid complex such as, for example, liposomes or other lipid-based nanoparticles such as a lipid-based vesicle (e.g., a DOTAP:cholesterol vesicle). In further embodiments, the SHP2 inhibitor may be encapsulated within a liposome, such as a mulitlamellar, vesicular, or multivesicular liposome. These liposomes may be targeted for liver delivery.

Liposomes are vesicular structures characterized by a phospholipid bilayer membrane and an inner aqueous medium. They form spontaneously when phospholipids are suspended in an excess of aqueous solution. The lipid components may undergo self-rearrangement before the formation of closed structures and entrap water and dissolved solutes between the lipid bilayers (Ghosh and Bachhawat, 1991). Liposomes may be characterized by membrane type and by size. Small unilamellar vesicles (SUVs) have a single membrane and typically range between 0.02 and 0.05 am in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles. Multilamellar liposomes have multiple lipid layers separated by aqueous medium.

In some aspects, the present disclosure provides formulations comprising liposomes containing a SHP2 inhibitor, such as an allosteric inhibitor of SHP2, a SHP2 antibody, or an RNAi or siRNA directed to SHP2. Alternatively, or in addition, the compounds disclosed herein may be contained within, or adsorbed onto, the liposome bilayer of the liposome. A SHP2 inhibitor, such as an allosteric inhibitor of SHP2, and any associated nucleic acids may be aggregated with a lipid surfactant and carried within the liposome's internal space; in these cases, the liposome membrane is formulated to resist the disruptive effects of the active agent-surfactant aggregate.

In some embodiments, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

In some embodiments, SHP2 inhibitors (e.g. an allosteric inhibitor of SHP2, a SHP2 antibody, or a SHP2 RNAi or siRNA) contained within liposomes are in solubilized form. In some aspects, aggregates of surfactant and active agent (such as emulsions or micelles containing the active agent of interest) may be entrapped within the interior space of liposomes. A surfactant may act to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. In some aspects, the surfactants have CMCs in the micromolar range; higher CMC surfactants may be utilized to prepare micelles entrapped within liposomes, however, micelle surfactant monomers could affect liposome bilayer stability and would be a factor in designing a liposome of a desired stability.

Liposomes may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In some aspects, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

A SHP2 inhibitor as described herein, or a SHP2 RNAi or siRNA molecule, may be delivered to a target cell via receptor mediated delivery vehicles. These approaches can take advantage of the selective uptake of macromolecules by receptor mediated endocytosis in a target cell.

The receptor mediated targeting vehicle may comprise a cell receptor specific ligand, such as liver targeting ligands, and a nucleic acid binding agent. In some embodiments, the vehicle comprises a cell receptor specific ligand to which the nucleic acid to be delivered has been operatively attached.

Several ligands have may be used for receptor mediated gene transfer such as, e.g., those described in Wu and Wu, 1987; Wagner et al., 1990; Perales et al., 1994; Myers, or EPO 0273085. Such receptor mediated targeting vehicles may selectively target a variety of mammalian cell types. The ligand may selectively bind a receptor expressed on the surface of a target cell population such as, e.g., a liver cell or a cancerous cell.

In other embodiments, a SHP2 inhibitor targeting vehicle may comprise a specific binding or liver targeting ligand in combination with a liposome. The SHP2 inhibitors to be delivered may be housed within the liposome and the specific binding ligand is functionally incorporated into the liposome membrane. The liposome will thus specifically bind to the receptor(s) of a target cell and deliver the contents to a cell. In particular, the SHP2 inhibitors may be targeted to the liver. Liver delivery of SHP2 inhibitors may use liposome delivery systems, such as small unilamellar vesicles, large unilamellar vesicles and multilamellar vesicles. The liposomes may be formed from a variety of phospholipids, such as cholesterol, stearylamine, phophatidylcholines (e.g., lecithin), etc. Liver delivery of SHP2 inhibitors may also be accomplished using monoclonal antibodies as individual carriers to which the SHP2 inhibitors may be coupled, or the SHP2 inhibitors may be coupled with liver targeting ligands to provide targetable drug carriers (e.g., for the liver). Liver targeting ligands include, for example, mannose-6-phosphate, cyclic arginine-glycine-asparagine, platelet derived growth factor, human serum albumin, galactoside, galactosamine, linoleic acid, apolipoprotein A-I, acetyl CKNEKKNKIERNNKLKQPP-amide (SEQ ID NO: 17), pre-S1 and glycyrrhizin. In still further embodiments, the SHP2 inhibitor delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present disclosure can be specifically delivered into a target cell in a similar manner.

In some embodiments, a SHP2 inhibitory nucleic acid such as a SHP2 siRNA is comprised in a modular degradable dendrimer or a dendrimer nanoparticle. Modular degradable dendrimers are described, e.g., in Zhou et al., 2016. Dendrimers may be synthesized using sequential, orthogonal reactions where ester degradability is systematically integrated with chemically diversified cores, peripheries, and generations. In some embodiments, the modular degradable dendrimer is 5A2-SC8 (Zhou et al., 2016). The modular degradable dendrimer may be used to target the siRNA to the liver and/or reduce siRNA delivery to non-liver tissues.

V. Combination Therapies

A SHP2 inhibitor (e.g., an allosteric SHP2 inhibitor, or a SNP2 siRNA or RNAi) may be administered before, during, after, or in various combinations relative to an additional diabetes or cancer therapy. The administrations may be in intervals ranging from concurrently to minutes to days to weeks. In embodiments where the SHP2 inhibitor is provided to a patient separately from an additional therapeutic agent, one would generally ensure that a significant period of time did not expire between the time of each delivery, such that the two compounds would still be able to exert an advantageously combined effect on the patient. In some embodiments, the second therapy is a diabetes therapy such as metformin, a sulfonylurea, a meglitinide, a thiazolidinedione, a DPP-4 inhibitor, a GLP-1 receptor agonist (e.g., Byetta), a SGLT2 inhibitor, insulin, or MEK inhibitors. In some embodiments, the second therapy is an anti-cancer therapy such as a chemotherapy, an immunotherapy, a radiotherapy, a gene therapy, or a surgery. Anti-cancer therapies that may be utilized in various embodiments include alkylating agents, e.g., altretamine, busulfan, carboplatin, carmustine, chlorambucil, cisplatin, cyclophosphamide, dacarbazine, lomustine, melphalan, oxaliplatin, temozolomide, or thiotepa; mitotic inhibitors e.g., a taxane, a vinca alkaloid, paclitaxel, docetaxel, vincristine, vinblastine, vinorelbine or vinflunine; or other anticancer agents, e.g., 5-fluorouracil (5-FU), or 5-fluoro-2-4(1H,3H)-pyrimidinedione, 6-mercaptopurine (6-MP), capecitabine, cytarabine, floxuridine, fludarabine, flutamide, gemcitabine, hydroxyurea, methotrexate, pemetrexed, daunorubicin, doxorubicin, epirubicin, idarubicin, actinomycin-D, bleomycin, mitomycin-C, mitoxantrone, topotecan, irinotecan, etoposide, or teniposide; and MEK inhibitors e.g., PD0325901, GSK1120212, U0126-EtOH, AZD6244.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In Vitro Determination of the Mechanism of R Endocytosis

A. Mechanism of IR Endocytosis

Two sequence motifs in Insulin Receptor (IR)—the NPE999Y and di-leucine (1025LL) motifs—have previously been implicated in AP2 binding and IR endocytosis (Backer et al., 1990; Backer et al., 1991; Haft et al., 1994; Hamer et al., 1997) (FIG. 1A). The MAD2-interacting motif (MIM, 1372RILTL) of IR binds to the MAD2-BUBR1 module, which in turn recruits AP2 (Choi et al., 2016). HepG2 cell lines stably expressing IR-GFP WT, the MIM mutant (4A), Y999F, or L1025A/L1026A (AA) were generated, and the subcellular localization of these IR-GFP proteins were examined (FIGS. 5A-B). Without insulin treatment, IR WT, 4A, and Y999F localized to the plasma membrane, but IR L1025A/L1026A was enriched in intracellular compartment (IC). A large fraction of IR L1025A/L1026A co-localized with RAB7 (a late endosome marker), indicating that IR L1025A/L1026A underwent unscheduled endocytosis and accumulated in late endosomes (FIG. 5C). Thus, instead of promoting IR endocytosis, the di-leucine motif actually prevents it. Because this motif is located in a P strand of the IR kinase domain (FIG. 5D) and because the IR kinase activity is required for its endocytosis (Backer et al., 1991; Carpentier et al., 1993), it is possible that this mutation might cause spontaneous activation of IR and premature internalization.

IR Y999F, 4A, and Y999F/4A mutants were less efficiently internalized after insulin stimulation (FIG. 1B). As Y999 is phosphorylated in the activated IR (White et al., 1998), defective endocytosis of IR Y999F suggests that phosphorylation of Y999 (pY999) is required for timely IR internalization. The IR Y999F/4A double mutant was not significantly more defective than the single mutants (FIG. 1B), suggesting that the MIM and pY999 might promote insulin-activated IR endocytosis in the same pathway.

The phosphotyrosine-binding (PTB) domain of IRS1 and IRS2 directly binds to phosphorylated NPE999Y motif in activated IR (Eck et al., 1996; Gustafson et al., 1995; He et al., 1995; He et al., 1996; Wolf et al., 1995). Co-depletion of IRS1/2 blocked IR endocytosis induced by insulin, whereas depletion of either had no effect (FIG. 1C, FIGS. 6A-B). Expression of RNAi-resistant IRS1 restored IR endocytosis in cells depleted of both IRS1/2. Thus, IRS1/2 act redundantly to promote IR endocytosis.

Figure 1D:
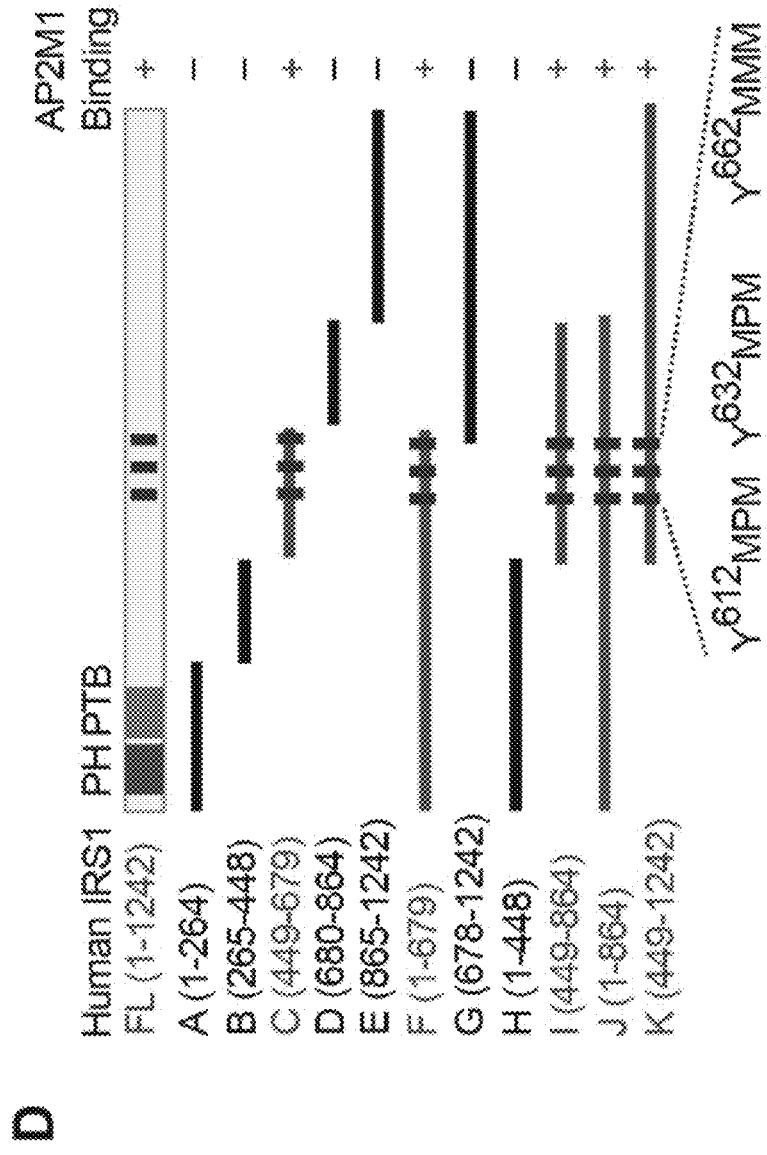
Figure 1E:
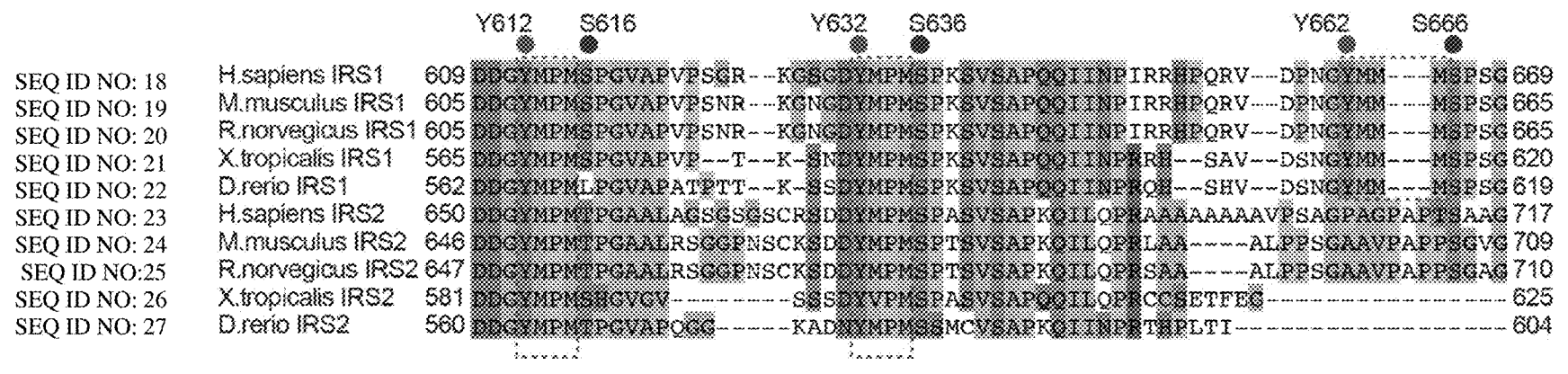

IRS1 interacts with AP1M1 through multiple YXXΦ (X, any amino acids; Φ, bulky hydrophobic residues) motifs in its central region (Yoneyama et al., 2013). This interaction regulates the intracellular localization of IRS1 itself. Because AP1M1 and AP2M1 share high sequence homology (Edeling et al., 2006), IRS1 interaction with AP2M1 was tested. In vitro translated Myc-IRS1 full-length and the YXXΦ-containing central region (residues 449-679) bound to GST-AP2M1 (FIG. 1D, FIGS. 6C and D). IRS2 is highly homologous to IRS1 and also has two conserved YXXΦ motifs (FIG. 1E) (Taniguchi et al., 2006). AP2M1 binds to YXXΦ motifs and promotes clathrin-mediated endocytosis (Traub et al., 2009). Thus, IRS1/2 contribute to IR endocytosis through bridging an interaction between AP2 and activated IR.

Figure 1F:
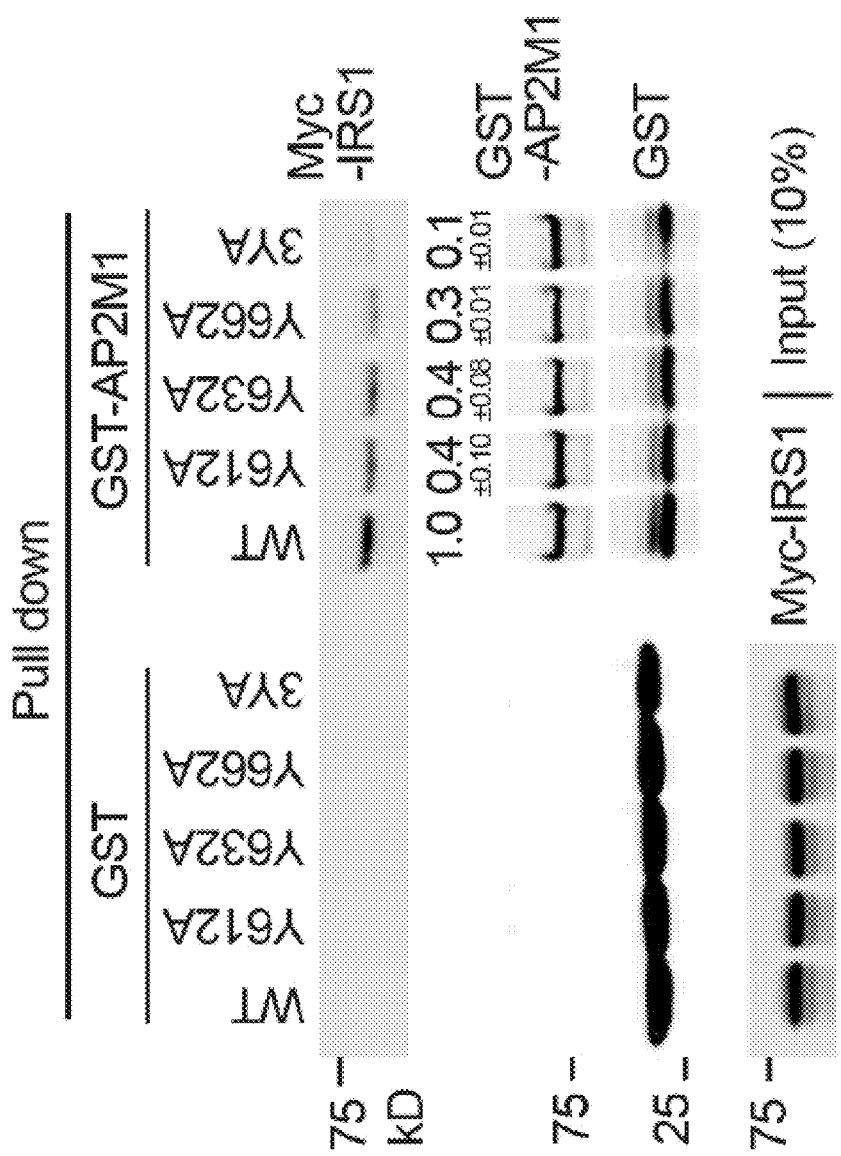
Figure 6E:
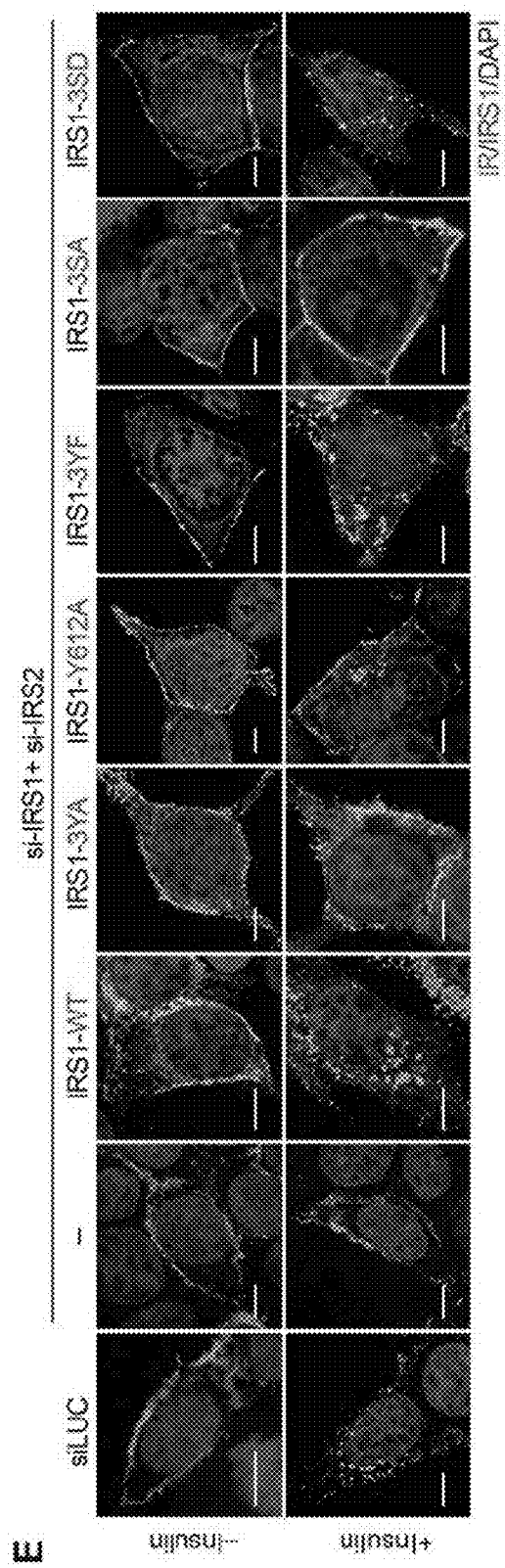

The AP2M1-binding region of IRS1 has 3 YXXΦ motifs (FIG. 1E), so mutations of YXXΦ motifs in IRS1 were tested for disruption of AP2M1 binding. In vitro translated IRS1 (residues 449-864) bound to GST-AP2M1 (FIG. 1F), but single YA mutant significantly reduced the IRS1-AP2M1 interaction, and 3YA (Y612A/Y632A/Y662A) further reduced it (FIG. 1F). RNAi-resistant IRS1 Y612A and 3YA mutants could not restore IR endocytosis in 293FT cells depleted of IRS1/2 (FIG. 1G and FIG. 6E). Failure of these mutants to functionally complement indicates that the IRS1/2-AP2M1 interaction is required for insulin-activated IR endocytosis. Endogenous IRS1 interacted with the AP2 complex in 293FT cells stimulated with insulin, but not in untreated cells (FIG. 1H). Thus, IRS1/2 bind to AP2 through canonical YXXΦ motifs in vitro and in human cells, and promote insulin-activated IR endocytosis.

B. Feedback Regulation of IR Endocytosis

Figure 2A:
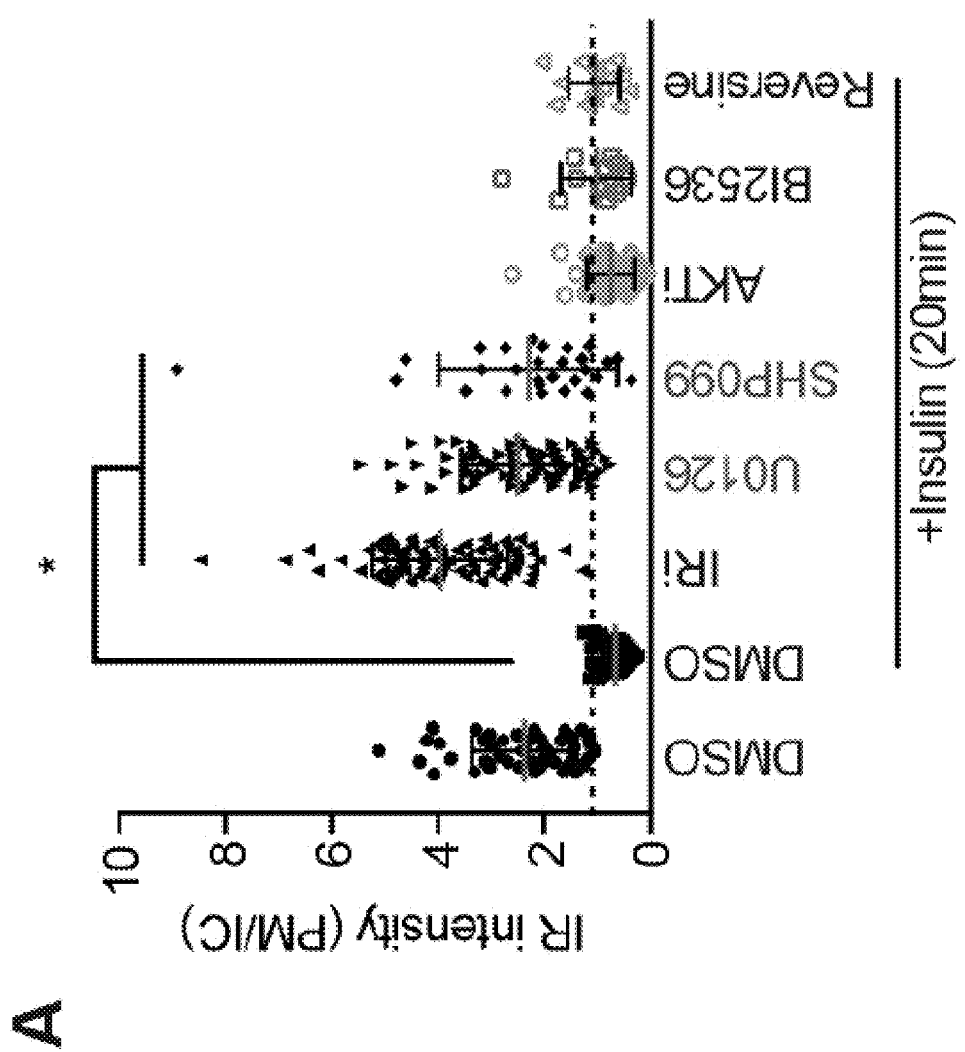

To test whether the MAPK pathway and SHP2 might regulate the IRS1/2-AP2 interaction and IR endocytosis through modulating IRS1/2 phosphorylation patterns, the effects of inhibiting SHP2 or the MAPK pathway on insulin-activated IR endocytosis were examined (FIG. 2A and FIG. 7A). The IR inhibitor (BMS536924) expectedly blocked IR endocytosis, as did the MEK inhibitor (U0126) and the SHP2 inhibitor (SHP099) (FIG. 2A). By contrast, the AKT inhibitor (AKTi, VIII) did not affect IR endocytosis, indicating a specific requirement for the MAPK pathway and SHP2. As controls, inhibitors of MPS1 (Reversine) and PLK1 (BI2546) did not appreciably inhibit IR endocytosis, ruling out the involvement of these mitotic kinases in this process.

Figure 2B:
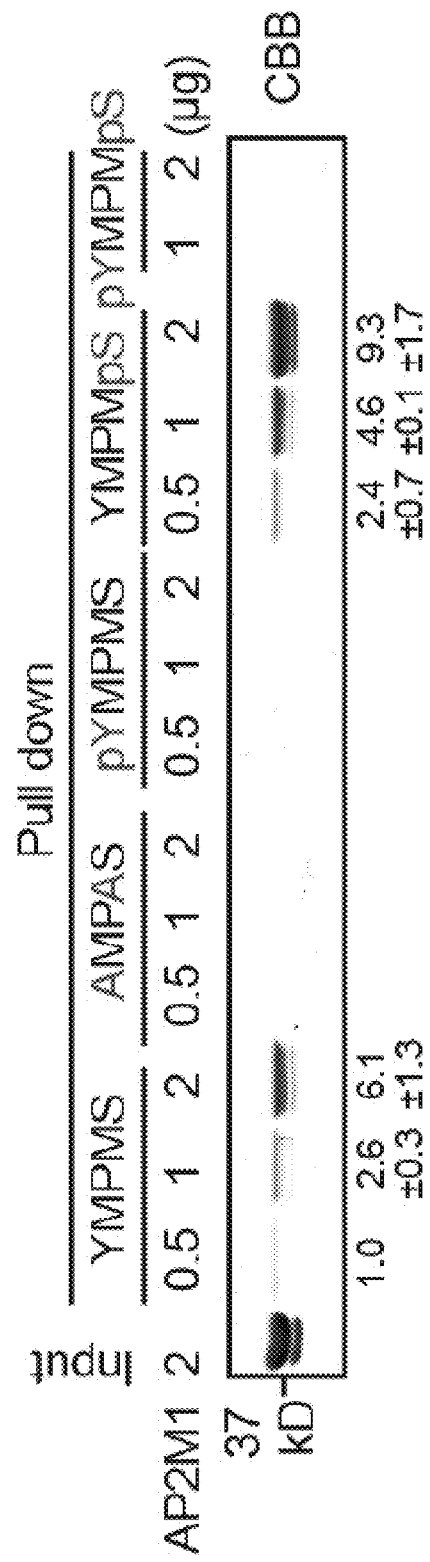
Figure 2C:
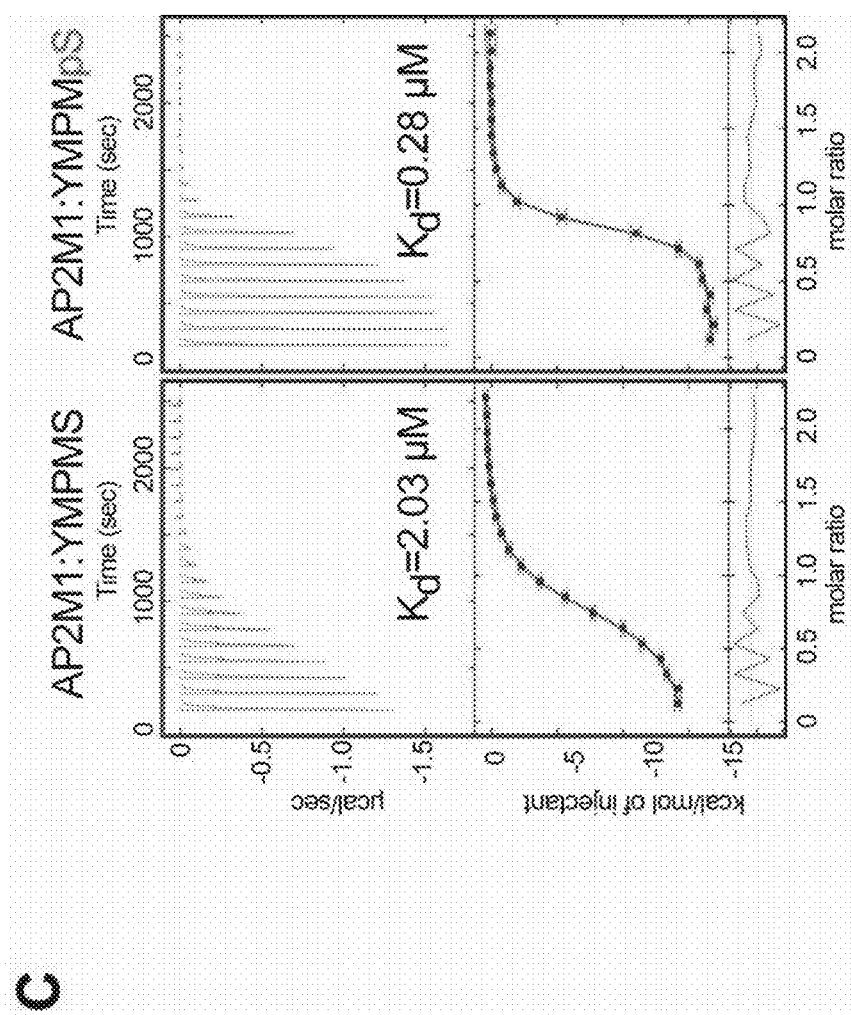

The unphosphorylated and phosphorylated IRS1 peptides containing 612YMPMS (SEQ ID NO:7) FIG. 7B) were chemically synthesized and used for in vitro pull-down assays to examine their binding to AP2M1 (FIG. 2B). The unphosphorylated IRS1 peptide (YMPMS (SEQ ID NO:7)) bound to AP2M1, but the mutant peptide with Y612 and M615 replaced by alanine (AMPAS (SEQ ID NO:9)) did not. Phosphorylation of the serine in the YMPMS motif (YMPMpS (SEQ ID NO:13)) enhanced AP2M1 binding. Isothermal titration calorimetry (ITC) measurements confirmed that the phospho-serine IRS1 peptide (pS-IRS1) indeed bound to AP2M1 with higher affinity ($K_d$=280 nM), as compared to the unphosphorylated peptide ($K_d$=2.03 μM) (FIG. 2C). Thus, phosphorylation of IRS1 by ERK1/2 enhances IRS1 binding to AP2M1. Phosphorylation of the tyrosine in the YMPMS motif (pYMPMS (SEQ ID NO: 11) and pYMPMpS (SEQ ID NO: 15)) abolished AP2M1 binding (FIG. 2B), suggesting that SHP2-dependent tyrosine dephosphorylation of IRS1 is required for AP2M1 binding.

To assess whether serine phosphorylation (pS616) of the YMPMS motif (SEQ ID NO:13) promotes dephosphorylation of pY612 by SHP2, its dephosphorylation kinetics were examined. Comparison of the dephosphorylation kinetics of singly (pYMPMS (SEQ ID NO: 11)) or doubly (pYMPMpS (SEQ ID NO: 15)) phosphorylated IRS1 peptides revealed that pS616 on IRS1 indeed promoted pY612 dephosphorylation by SHP2 in vitro (FIGS. 2D-E). Decreased IRS1 pS616 has been correlated with increased pY608 in vivo (Bard-Chapeau et al., 2005), and therefore, aside from directly augmenting the IRS1-AP2M1 interaction, ERK1/2-dependent phosphorylation of IRS1 indirectly promotes AP2M1 binding through enhancing the dephosphorylation of IRS1 by SHP2. Consistent with a role of ERK1/2-dependent phosphorylation of IRS1 in IR endocytosis, expression of the RNAi-resistant IRS1 phospho-mimicking mutant (3SD), but not the phospho-deficient mutant (3SA), restored IR endocytosis in 293FT cells depleted of IRS1/2 (FIG. 1G and FIG. 6E).

These results support a mechanism for insulin-activated IR endocytosis, in which the activated IR phosphorylates the tyrosine residues in YXXΦS motifs and the C-terminal SHP2-docking sites of IRS1/2, and stimulates the PI3K-AKT and MAPK pathways (FIG. 2F). In a negative feedback mechanism, activated ERK1/2 phosphorylate the serines in YXXΦS motifs on IRS1/2 and assist SHP2 to dephosphorylate IRS1/2 (FIG. 2F). The IRS1/2 YXXΦS motifs with the serine phosphorylated and tyrosine dephosphorylated bind to AP2 with optimal affinities, promoting clathrin-mediated endocytosis of IR (FIG. 2F).

C. Structural Basis of the Phospho-Regulation of IR Endocytosis

To understand better the phospho-regulation of the AP2-IRS1 interaction, the crystal structure of AP2M1 (residues 160-435) bound to the serine-phosphorylated YXXΦS motif from IRS1 (pS-IRS1) was determined (Table 2, FIG. 2G).

The overall structure of the AP2M1-pS-IRS1 complex was similar to those of previously determined structures of AP2M1 bound to other YXXD motifs. AP2M1 contained two interlinked β-sandwich subdomains: subdomain 1 (11-6 and 17-19) and subdomain 2 (37-16) (FIG. 2G). The pS-IRS1 peptide binds at the edges of strands 118 and 317 in subdomain 1, and interacts with residues from strands 31, 117, and 118 (FIG. 2G and FIG. 2H). In particular, Y612 and M615 make extensive hydrophobic interactions with AP2M1. The RNAi-resistant IRS1 3YF mutant with tyrosines in the YXXΦS motifs replaced by phenylalanines could not fully restore IR endocytosis in 293FT cells depleted of IRS1/2 (FIG. 1G and FIG. 6E). The hydroxyl group of Y612 forms a hydrogen bond with D176 in 31, providing an explanation for why phenylalanines cannot functionally substitute for tyrosines. Phosphorylation of Y612 is expected to introduce both static hindrance and unfavorable electrostatic interactions with D176, explaining why tyrosine phosphorylation of YXX(S motifs disrupts the IRS1-AP2 interaction.

Well-defined electron density for pS616 in IRS1 was not observed, despite its ability to enhance the IRS1-AP2 interaction. pS616 is located in the vicinity of a positively charged patch on AP2M1 formed by residues K405, H416, and K420 (FIG. 2I), suggesting that the phospho-serine might engage in favorable electrostatic interactions with this basic patch. Mutations of H416 and K420 did not, however, reduce IRS1 binding (FIG. 7C-E). Mutation of K405 destabilized the AP2M1 protein and reduced its binding to both the phosphorylated (pS612) and unphosphorylated IRS1 peptides. Thus, consistent with the lack of electron density, pS616 does not make defined electrostatic interactions with specific acceptor residues, and interacts with the positively charged patch as one structural entity.

Example 2

Endocytosis of IR In Vivo

A. SHP2 Inhibition Improves Insulin Sensitivity in Mice

The allosteric SHP2 inhibitor, SHP099, stabilizes the inactive conformation of SHP2, thus inhibiting its phosphatase activity (Chen et al., 2016). Wild type mice maintained on a HFD were treated with SHP099 (60 mg/kg body weight) by daily oral gavage for 6 days and then tested for glucose and insulin tolerance. SHP099 administration markedly increased glucose tolerance and insulin sensitivity in HFD-fed mice (FIGS. 3A and B). SHP099 did not change the body weight of these mice (FIG. 8A). The IR staining at the PM in liver sections from mice fed with HFD was weak, and insulin stimulation further reduced it and caused IR endocytosis (FIGS. 3C and D). SHP099 administration elevated the IR signal at the PM in the absence of insulin, and blocked insulin-activated IR endocytosis. These results establish a requirement for SHP2 in promoting IR endocytosis in vivo.

To examine the effect of SHP2 inhibition on insulin signaling in freshly isolated primary hepatocytes, the activating phosphorylation of IR (pY1189/1190), AKT (pT308), and ERK1/2 (pT202/Y204, pERK1/2) in the hepatocytes was monitored (FIG. 3E and FIG. 8B). SHP099 inhibited the activation of the MAPK pathway by insulin in primary hepatocytes. By contrast, insulin-triggered activating phosphorylation of IR and AKT was significantly increased and prolonged in SHP099-treated primary hepatocytes. These results suggest that targeting SHP2 can block the feedback regulation of IR endocytosis by selectively inhibiting the MAPK pathway. Signaling through the PI3K-AKT pathway, which regulates metabolism and does not depend on SHP2, is prolonged as a result of suppressed IR endocytosis.

B. Dysregulation of IR Endocytosis in Human Insulin Resistance Syndromes.

To test whether IR internalization was involved in human insulin resistance syndromes, the IR PM levels in liver biopsies from human patients were examined. Because of the challenges of collecting liver biopsies from normal healthy individuals, liver biopsies of patients with hepatocellular carcinoma that contained normal (non-malignant) and malignant hepatocytes were used, and only normal hepatocytes were analyzed. Immunohistochemistry (IHC) with anti-IR and anti-ZO1 (as a PM marker) antibodies on 51 non-diabetic and 19 type 2 diabetes patient samples was performed to analyze IR PM levels. IR PM signals in the liver biopsies from type 2 diabetes patients were significantly weaker than those in non-diabetic patients (FIGS. 4A-B), suggesting that reduced IR PM levels might contribute to insulin resistance in human patients.

Figure 9D:
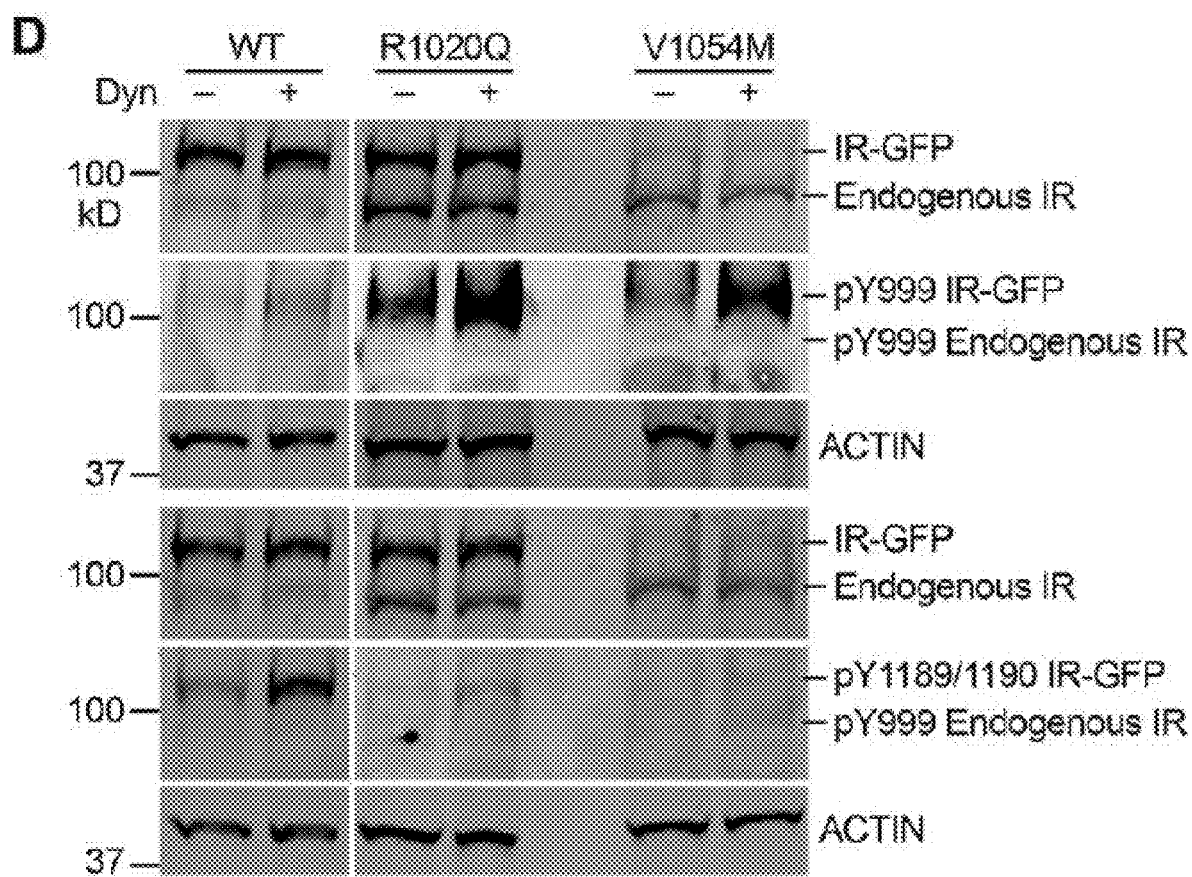

Mutations of IR are known to cause inherited severe insulin resistance syndromes, but the mechanisms by which these mutations affect IR function have not been systematically explored. HepG2 cell lines were generated which stably expressed IR mutants fused to GFP, and the subcellular localization of these IR-GFP proteins was examined (FIGS. 9A-C and Table 1).

Figure 4D:
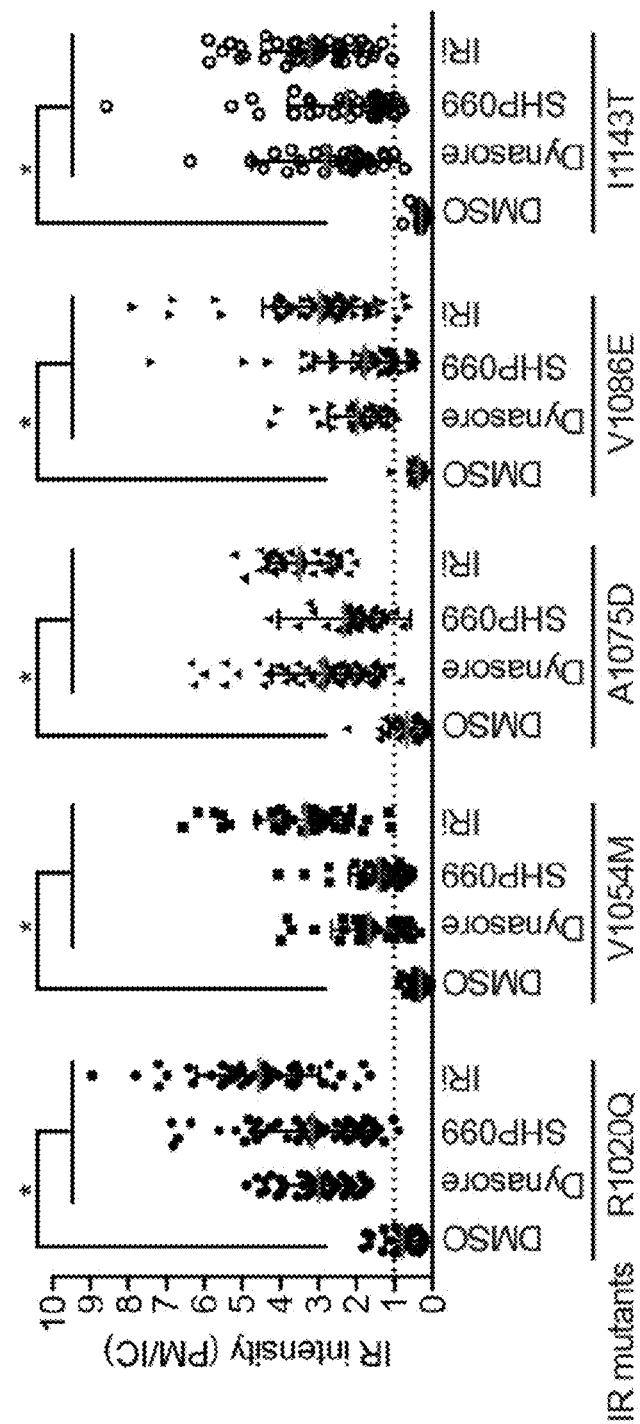
Figure 4E:
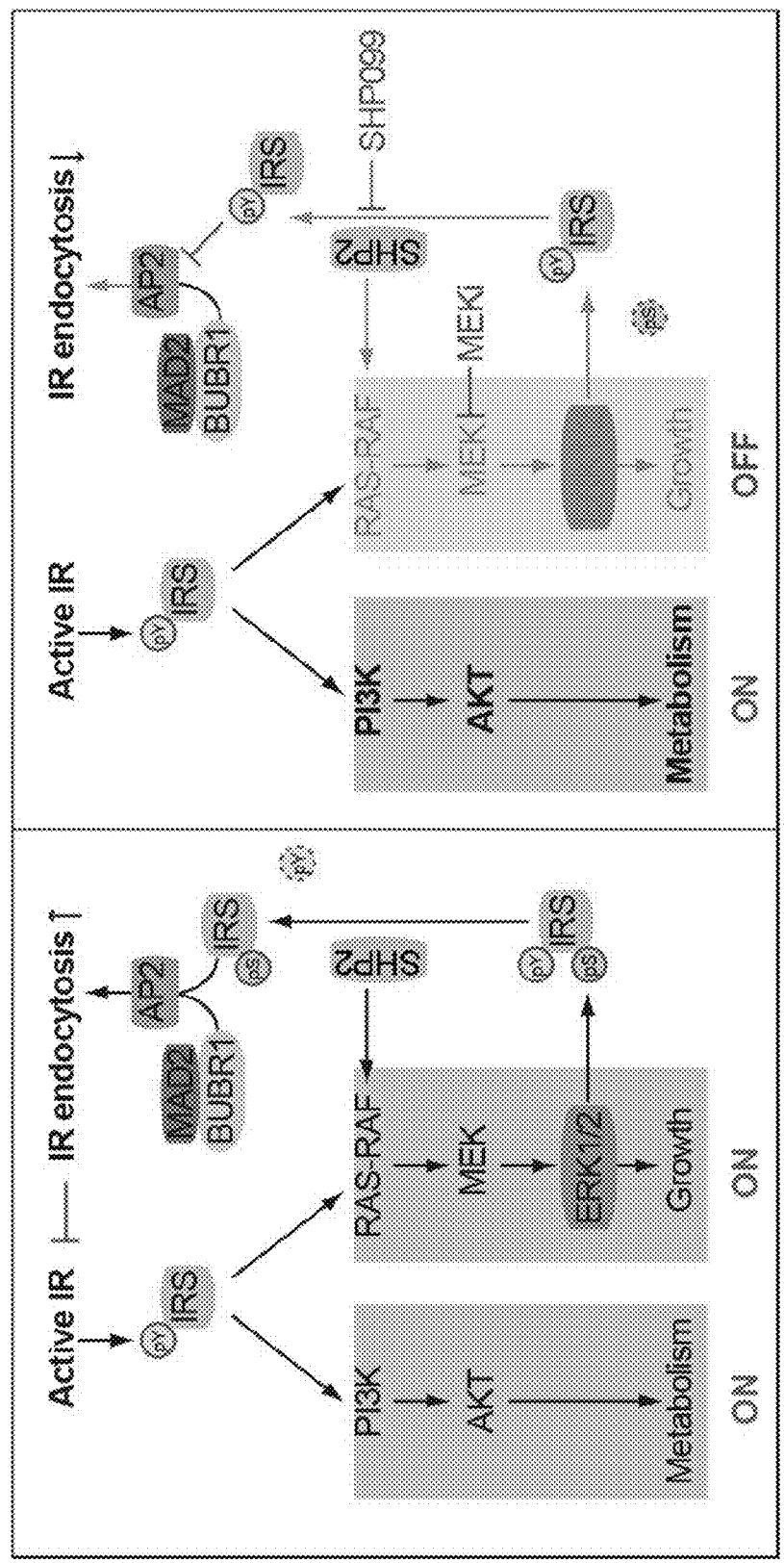

There were three distinct classes of IR mutants based on their subcellular localization in the unstimulated state. Class I mutants localized to the PM. Class II mutants showed reduced signals at the PM, and were enriched in RAB7-positive intracellular compartments (FIGS. 4C-D). Class III mutants stayed in the ER and the Golgi apparatus, indicating that Class III mutations affect IR processing and trafficking. Addition of dynasore, an inhibitor of dynamin, elevated the IR signal of Class II mutants at the PM (FIGS. 4C-D), suggesting that Class II mutations cause premature clathrin-mediated endocytosis of IR prior to insulin stimulation. The IR inhibitor restored Class II IR mutants at the PM. Moreover, pY999 (a docking site for IRS1/2), but not pY1189/1190 (in the catalytic domain), of IR R1020Q or V1054M was significantly increased in the absence of insulin stimulation, as compared to IR WT and endogenous IR (FIG. 9D), which suggests that unscheduled activation of their kinase activity might underlie their premature internalization. Thus, certain IR mutations found in human insulin resistance syndromes perturbs IR kinase regulation and causes premature IR endocytosis.

Cellular localization of IR mutants was examined after inhibiting the SHP2 or MAPK pathways (FIGS. 4C-D, and FIGS. 9A-C). SHP099 or U0126 treatment significantly enhanced the PM levels of Class II IR mutants, but not those of Class I and III IR mutants. These results support the use of a SHP2 inhibitor to reduce IR endocytosis and/or alleviate insulin resistance, e.g., in patients with a class II IR mutation or type 2 diabetes.

Example 3

Materials and Methods

A. Animal Methods

All animals were maintained in a specific antigen-free barrier facility with 12 h light/dark cycles (6 AM on and 6 PM off). Mice were fed a standard rodent chow (2016 Teklad Global 16% protein rodent diet, Harlan Laboratories). For inducing insulin resistance, C57BL/6J (Stock No. 000664, Jackson laboratory) were fed a high-fat (60%) diet (Open-Source Diets, Cat. No. D12492). For in vivo pharmacological assays, 6-8-weeks-old male mice were fed high-fat diet (HFD) for 5 weeks. Two days before drug administration, mice were switched to normal chow. SHP099 (MedChem Express) was dissolved in DMSO and diluted into a 0.5% hypromellose and 0.1% Tween-80 solution. 60 mg/kg of SHP099 was administered by daily oral gavage for 6 days. For glucose tolerance test, mice were fasted for 14 h, and their blood glucose levels (T=0) were measured with tail bleeding using a glucometer (AlphaTRAK®). Then, 2 g of glucose/kg of body weight was injected intraperitoneally. Blood glucose levels were measured at 15, 30, 60, and 120 min after glucose injection. For insulin tolerance test, mice fasted for 4 h were injected intraperitoneally with recombinant human insulin (Eli Lilly) at 1 U/kg body weight, and their blood glucose levels were measured at 0, 15, 30 and 60 min after injection.

B. Reagents

Generation of rabbit polyclonal antibodies against GST was described previously (Choi et al., 2016). The following antibodies were purchased from commercial sources: anti-ZO-1/TJP1 and anti-ACTIN (MA137018; Thermo Scientific®); anti-IR-pY1150/1151 (19H7; labeled as pY1189/1190 IR in this study), anti-AKT (40D4), anti-pT308 AKT (D25E6), anti-ERK1/2 (L34F12), anti-pERK1/2 (197G2) and anti-RAB7 (D95F2, Cell Signaling Technology®); anti-IRS1-pY612, anti-IR-pY972 (labeled as pY999 IR in this study) and anti-IR (CT-3, Millipore®); anti-AP2B1 (BD Biosciences®); anti-IRS2 (EPR904) and anti-AP2M1 (EP2695Y, Abcam®); anti-GFP and anti-MYC (9E10; Roche®); anti-IRS1 (A301-158A, Bethyl laboratory).

The small interfering RNAs (siRNAs) were synthesized by Dharmacon® (Lafayette, Colo.) and had the following sequences: human IRS1 (GAA CCU GAU UGG UAU CUA C dTdT, SEQ ID NO:5); human IRS2 (On-TARGETplus® human IRS2 (8660) siRNA-SMARTpool®); siLUC (UCA UUC CGG AUA CUG CGA U, SEQ ID NO:6). The cDNAs encoding human IRS1 and human AP2M1 were purchased from Thermo Scientific®. The siRNA-resistant and YXXΦ motif mutants of IRS1 were generated by site-directed mutagenesis (Agilent Technologies®). IRS1 peptides (YMPMS (SEQ ID NO:7), CHTDDGYMPMSPGVA (SEQ ID NO:8); AMPAS (SEQ ID NO:9), CHTDDGAM-PASPGVA (SEQ ID NO:10); pYMPMS (SEQ ID NO:11), CHTDDGpYMPMSPGVA (SEQ ID NO:12); YMPMpS (SEQ ID NO:13), CHTDDGYMPMpSPGVA (SEQ ID NO:14); pYMPMpS (SEQ ID NO:15), CHTDDGpYMPMpSPGVA (SEQ ID NO:16)) were chemically synthesized at KareBay™ Biochem, Inc.

For testing the effects of kinase inhibitors on IR endocytosis, the cells were serum starved for 14 h and inhibitors were added at 2 h before insulin treatment. Inhibitors used in this study were as follows: the IR kinase inhibitor, BMS536924 (2 µM; Tocris®), the MEK inhibitor, U0126 (40 µM; Cell Signaling Technologies®), the SHP2 inhibitor, SHP099 (40 µM; Medchem Express®), the AKT inhibitor VIII (5 µM, Calbiochem®), the PLK1 inhibitor, BI2536 (200 nM, Selleck® Chemicals), and the MPS1 inhibitor, Reversine (1 µM, Sigma®).

C. Cell Culture, Transfection, and Viral Infection

293FT and HepG2 cells were cultured in high-glucose DMEM supplemented with 10% (v/v) FBS, 2 mM L-glutamine, and 1% penicillin/streptomycin. Plasmid transfections into 293FT and HepG2 cells were performed with Lipofectamine® 2000 (Invitrogen®). siRNA transfections were performed with Lipofectamine® RNAiMAX (Invitrogen®).

In order to generate 293FT or HepG2 cells expressing IR-GFP WT, cDNAs encoding IR mutants were cloned into the pBabe-GFP-puro vector. The vectors were co-transfected with viral packaging vectors into 293FT cells, and the viral supernatants were collected at 2 days and 3 days after transfection. The concentrated viruses were added to 293FT and HepG2 cells with 4 µg/ml of polybrene. Cells were selected with puromycin (1 µg/ml for 293FT and 2 µg/ml for HepG2) at 3 days after infection and sorted by FACS to collect cells expressing similar levels of IR-GFP.

Primary hepatocytes were isolated from 2-month-old female mice with a standard two-step collagenase perfusion procedure. Cells were plated on collagen-coated dishes and incubated in attachment medium (Williams' E Medium supplemented with 5% (v/v) FBS, 10 nM insulin, 10 nM dexamethasone, and 1% (v/v) penicillin/streptomycin). After 2-4 h, the medium was changed to low-glucose DMEM supplemented with 5% (v/v) FBS, 10 nM dexamethasone, 10 nM insulin, 100 nM triiodothyronine, and 1% (v/v) penicillin/streptomycin. After 1 day, the cells were serum starved for 14 h and treated with dimethyl sulfoxide (DMSO) or SHP099 for the indicated times.

D. Tissue Histology and Immunohistochemistry

The fixation, histological analysis, and immunohistochemistry of mouse tissues were performed as described previously (Choi et al., 2016). For human patient sample analysis, the deparaffinized sections were subjected to antigen retrieval with 10 mM sodium citrate (pH 6.0), incubated with 0.3% $H_2O_2$, blocked with 0.3% BSA, and then incubated first with anti-IR (CT3, Millipore®, 1:100) and anti-ZO1 (Thermo Scientific®, 1:200) antibodies and then with secondary antibodies (AlexaFluor® 568 goat anti-mouse and AlexaFluor® 488 goat anti-rabbit; Molecular Probes®). The slides were counterstained with DAPI. Five to nine images (depends on the percentage of normal hepatocytes) were randomly taken under 40× magnification. The total cell numbers and numbers of IR PM-positive cells were counted at least twice for individual images. Over 100 cells were analyzed for each patient samples. All immunohistochemistry and scoring were performed blinded to the diabetes status.

E. Immunoprecipitation (IP) and Quantitative Western Blots

Cells were incubated with the cell lysis buffer [50 mM HEPES (pH 7.4), 150 mM NaCl, 10% (v/v) Glycerol, 1% (v/v) Triton X-100, 1 mM EDTA, 100 mM sodium fluoride, 2 mM sodium orthovanadate, 20 mM sodium pyrophosphate, 0.5 mM dithiothreitol (DTT), 2 mM phenylmethylsulfonyl fluoride (PMSF)] supplemented with protease inhibitors (Roche®) and PhosSTOP™ (Roche®) on ice for 1 h. The cell lysates were cleared by centrifugation and incubated with antibody-conjugated beads. The beads were washed, and the bound proteins were eluted with the SDS sample buffer and analyzed by SDS-PAGE and Western blotting. For quantitative Western blots, anti-rabbit immunoglobulin G (IgG) (H+L) (Dylight 800 or 680 conjugates) and anti-mouse IgG (H+L) (Dylight 800 or 680 conjugates) (Cell Signaling) were used as secondary antibodies. The membranes were scanned with the Odyssey Infrared Imaging System (LI-COR®, Lincoln, Nebr.).

F. Immunofluorescence

Indirect immunofluorescence microscopy was performed on cells grown on coverslips and fixed in cold methanol at −20° C. for 10 min. The fixed cells were incubated with PBS for 30 min and 3% BSA in 0.1% PBST for 1 h, and then treated with diluted antibodies in 0.3% BSA in 0.1% PBST at 4° C. overnight. After being washed, cells were incubated with fluorescent secondary antibodies and mounted on microscope slides in ProLong Gold Antifade reagent with DAPI (Invitrogen). Images of fixed cells were acquired as a series of 0.4 m stacks with a DeltaVision® system (Applied Precision®, Issaquah, Wash.). Raw images were deconvolved using the iterative algorithm implemented in the softWoRx® software (Applied Precision®, Issaquash, Wash.). The central section of a 0.4 μm z-stack containing 3 contiguous focal planes was used for quantification. The cell edges were defined with Image J. The whole cell signal intensity (WC) and intracellular signal intensity (IC) were measured. The plasma membrane signal intensity (PM) was calculated by subtracting IC from WC. Identical exposure times and magnifications were used for all comparative analyses.

G. Protein Purification

The full-length human AP2M1 was cloned into a pGEX 6P-1, and the plasmid was transformed into *Escherichia coli* strain BL21 (DE3). Protein expression was induced by 0.2 mM isopropyl β-D-1-thiogalactopyranoside (IPTG) at 25° C. overnight. The harvested pellets were lysed in the lysis buffer I (20 mM Tris-HCl, pH 8.0, 150 mM NaCl, 1% (v/v) TritonX-100, 5% (v/v) Glycerol, 1 mM DTT, 1 mM PMSF). After sonication, lysates were cleared by centrifugation at 4° C. The supernatants were filtered by 0.45 μM filter and incubated with pre-equilibrated Glutathione Sepharose 4B beads (GE Healthcare®) The resulting protein-bound beads were washed extensively with lysis buffer I.

The AP2M1 fragment (residues 160-435) was cloned into a modified pET28a that introduced an N-terminal His6-tag followed by a thrombin cleavage site. The plasmid was transformed into BL21(DE3) *E. coli* cells. Protein expression was induced by 0.2 mM IPTG at 20° C. overnight. The harvested pellets were lysed in the lysis buffer II (20 mM Tris-HCl, pH 7.5, 500 mM NaCl, 20 mM Imidazole, 1 mM PMSF). After sonication, lysates were cleared by centrifugation at 4° C. The supernatants were filtered by 0.45 μM filter and incubated with pre-equilibrated Ni2+-NTA beads (Qiagen®). Protein-bound beads were washed with 150 ml of wash buffer I (20 mM Tris-HCl, pH 7.5, 1M NaCl, 20 mM Imidazole) and with 50 ml of wash buffer II (20 mM Tris-HCl, pH 7.5, 100 mM NaCl, 20 mM Imidazole). The proteins were then eluted with the elution buffer (20 mM Tris-HCl, pH 7.5, 100 mM NaCl, 150 mM Imidazole) and incubated with thrombin (Sigma®) at 4° C. overnight. The protein was further purified with a Superdex 200 size exclusion column (GE Healthcare®). The relevant protein fractions were pooled, aliquoted, and snap-frozen for future experiments.

H. Crystallization of the AP2M1-IRS1 Complex

Protein crystallization studies were performed using the following methods. The purified AP2M1 (residues 160-435) was mixed with the pS-IRS1 peptide (CHTDDGYMPMpSPGVA (SEQ ID NO: 14), residues 607-620) at a molar ratio of 1:5 and then crystallized with the hanging-drop vapor diffusion method. The crystals of the AP2M1-pS-IRS1 complex grew within few days after the protein solution was mixed with the reservoir solution (1.0 M sodium malonate, pH 5.0, 0.1 M sodium acetate trihydrate, pH 4.5, 2% (w/v) PEG 20k). All crystals were cryoprotected with the reservoir solution including 15% (w/v) glycerol for data collection.

I. Data Collection and Structure Determination

X-ray diffraction studies of the crystallized proteins were performed as follows. X-ray diffraction datasets were collected at the Advanced Photon Source (APS) beamline Sector 19-ID at a wavelength of 0.97914 Å and at 100K. HKL3000 was used to process the datasets (Minor et al., 2006). The crystal of the AP2M1-pS-IRS1 complex diffracted to a minimum Bragg spacing of 3.2 Å and exhibited the symmetry of space group P64 with cell dimensions of a=b=125.33 Å, c=74.82 Å. There are two molecules in the asymmetric unit, with a 53.4% solvent content.

The structure was determined by molecular replacement with PHASER-MR (McCoy 2007), using the structure of the AP2M-IGN38 complex (PDB ID: 1BXX) as the search model. Structure refinement was performed with COOT and PHENIX (Emsley and Cowtan 2004; Emsley and Lohkamp 2010; Adams et al., 2010). The final Rwork and Rfree were 20.3% and 23.6%, respectively. Data collection and refinement statistics are provided in Table 3. The model quality was validated with Molprobity (Chen et al., 2012). All structural figures were generated with the program PyMOL (pymol.org) with the same color and labeling schemes.

TABLE 3

Data processing and refinement statistics

|  | AP2M1-IRS1 |
|---|---|
| Data collection | |
| Space group | P6$_4$ |
| Cell dimensions | |
| a, b, c (Å) | 125.33, 125.33, 74.82 |
| a, b, g (°) | 90.00, 90.00, 120.00 |
| Resolution (Å) | 32.6-3.20 (3.26-3.20) |
| R$_{merge}$ (%) | 16.1 (29.2) |
| <I>/<s$_I$> | 13.2 (1.4) |
| Completeness (%) | 100 (100) |
| Number of total reflections | 152046 |
| Number of unique reflections | 11485 |
| Redundancy | 12.4 (13.3) |
| Refinement | |
| Resolution (Å) | 27.14-3.20 (3.31-3.20) |
| No. reflections (work/free) | 11157 (1113)/1113 (113) |
| R$_{work}$/R$_{free}$ | 20.3 (29.1)/23.6 (35.9) |
| R.m.s deviations | |
| Bond lengths (Å) | 0.01 |
| Bond angles (°) | 1.30 |
| Completeness (%) | 100 |
| Ramachandran plot | |
| Favored (%) | 91 |
| Allowed (%) | 8.4 |
| Outliers (%) | 0.4 |

*Highest-resolution shell is shown in parenthesis.

J. Protein-Binding Assays

For GST pull-down assays of in vitro translated (IVT) IRS1 proteins, beads bound to GST-AP2M1 or GST were incubated with IVT products diluted in the cell lysis buffer at 4° C. for 2 h. After incubation and washing, proteins bound to beads were eluted with the SDS loading buffer, resolved with SDS-PAGE, and detected with Coomassie staining or immunoblotting with the appropriate antibodies. Peptide pull-down assays were performed as described previously (Choi et al., 2016). The isothermal titration calorimetry (ITC) assays were performed with a MicroCal Omega ITC200 titration calorimeter (GE Life Sciences®) at 20° C. with minor modifications (Ji et al., 2017). Briefly, the recombinant AP2M1 protein (residues 160-435) and peptides were dialyzed into the HEPES buffer (25 mM HEPES, pH 7.5, 50 mM NaCl). For each titration, 300 μl of AP2M1 (50 μM) were added to the calorimeter cell. IRS1 peptides (YMPMS, 528.9 μM or YMPMpS, 507.4 μM) were injected with an injection syringe in nineteen 2.0-μl portions. Raw data were processed and fitted with the NITPIC software package (Keller et al., 2012).

K. In Vitro Phosphatase Assays

Active SHP2 (2.9 μM, SignalChem) diluted in the phosphatase dilution buffer (50 mM imidazole, pH 7.2, 0.2% 2-mercaptoethanol, 65 ng/μl BSA) was incubated with IRS1 peptides (2.6 mM) at 37° C. for the indicated time points. Two microliters of reaction products were spotted onto 0.45 m nitrocellulose membrane (BioRad) and dried completely. The membrane was blocked with 5% nonfat milk in TBS for 1 h, and washed once with TBS-T (0.02% Tween 20). The membrane was incubated with anti-IRS1-pY612 antibodies diluted in TBS-T at 4° C. overnight. After washing with TBS-T, the anti-rabbit immunoglobulin G (IgG) (H+L) Dylight 800 conjugates (Cell Signaling) were applied as secondary antibodies. The membranes were scanned with the Odyssey Infrared Imaging System (LI-COR, Lincoln, Nebr.) for quantification.

L. Statistical Analyses

Prism was used for the generation of all curves and graphs and for statistical analyses. Results are presented as mean±SEM or mean±SD. Two-tailed unpaired t tests were used for pairwise significance analysis. Sample sizes were determined on the basis of the maximum number of mice that could be bred in similar ages to maintain well-matched controls. Power calculations for sample sizes were not performed. We monitored weight and health conditions of mice, and excluded mice from experiments if the animal was unhealthy and the body weight was more than two standard deviations from the mean. Randomization and blinding methods were not used, and data were analyzed after the completion of all data collection in each experiment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,506,559
U.S. Pat. No. 6,573,099
U.S. Pat. No. 3,453,259
U.S. Pat. No. 3,459,731
U.S. Pat. No. 3,453,257
U.S. Pat. No. 3,420,788
U.S. Pat. No. 3,426,011
U.S. Pat. No. 5,134,127
U.S. Pat. No. 4,235,871
U.S. Pat. No. 4,737,323
U.S. Pub. No. 2003/0051263
U.S. Pub. No. 2003/0055020
U.S. Pub. No. 2004/0265839
U.S. Pub. No. 2002/0168707
U.S. Pub. No. 2003/0159161
U.S. Pub. No. 2004/0064842
U.S. Pub. No. 2017/0015680
U.S. Pub. No. 2017/0001975
U.S. Pub. No. 2017/0204080
U.S. Pub. No. 20170015680
U.S. Pub. No. 20170001975
U.S. Pub. No. 20170204080
EPO 0273085
WO 2016/203404
WO 96/14057
Adams et al., *Acta Crystallogr. D Biol. Crystallogr.* 66, 213-221, 2010.

American Diabetes Association, *Diabetes Care,* 32: S62-S67, 2009.
Araki T, et al., Mouse model of Noonan syndrome reveals cell type- and gene dosage-dependent effects of Ptpn11 mutation. Nat Med 10:849-857, 2004.
Araki T, et al., Noonan syndrome cardiac defects are caused by PTPN11 acting in endocardium to enhance endocardial-mesenchymal transformation. Proc Natl Acad Sci USA 106:4736-4741, 2009.
Ardon et al., *Mol. Genet. Metab. Rep.,* 1: 71-84, 2014.
Backer et al., *J. Biol. Chem.,* 265: 16450-16454, 1990.
Backer et al., *J. Cell Biol.,* 115: 1535-1545, 1991.
Banks et al., *Nature,* 517: 391-395, 2015.
Bard-Chapeau et al., *Nat. Med.,* 11: 567-571, 2005.
Binder et al., PTPN11 mutations are associated with mild growth hormone resistance in individuals with Noonan syndrome. *J Clin Endocrinol Metab.,* 90:5377-5381, 2005.
Bost et al., *Diabetes,* 54: 402-411, 2005.
Boucher et al., *Cold Spring Harb. Perspect. Biol.,* 6, a009191, 2014.
Bouzakri et al., *Diabetes,* 52: 1319-1325, 2003.
Carlson et al., *Diabetes,* 52: 634-641, 2003.
Carpentier et al., *J. Cell Biol.,* 122: 1243-1252, 1993.
Challis and Semple, Curr. Obes. Rep., 2:293, 2013.
Chen et al., *Acta Crystallogr. D Biol. Crystallogr.* 66, 12-21, 2010.
Chen et al., *Nature,* 535: 148-152, 2016.
Choi et al., *Cell,* 166: 567-581, 2016.
Dordunoo et al., *Drug Development and Industrial Pharmacy,* 17(12), 1991.
Eck et al., *Cell,* 85: 695-705, 1996.
Edeling et al., *Nat. Rev. Mol. Cell Biol,* 7: 32-44, 2006.
Emsley and Cowtan, *Acta Crystallogr. D Biol. Crystallogr.* 60, 2126-2132, 2004.
Emsley and Lohkamp, W. G. Scott, K. Cowtan, *Acta Crystallogr. D Biol. Crystallogr.* 66, 486-501, 2010.
Feng and Pawson, *Trends Genet.,* 10:54-58, 1994.
Fragale et al., Noonan syndrome-associated SHP2/PTPN11 mutants cause EGF-dependent prolonged GAB 1 binding and sustained ERK2/MAPK1 activation. *Hum Mutat* 23:267-277, 2004.
Ghosh and Bachhawat, 1991.
Gogg et al., *Diabetes,* 58: 2238-2245, 2009.
Gustafson et al., *Mol. Cell. Biol.,* 15: 2500-2508, 1995.
Haft et al., *J. Biol. Chem.,* 269: 26286-26294, 1994.
Hamer et al., *J. Biol. Chem.,* 272: 21685-21691, 1997.
Stahl and Wermuth (Eds.), *Handbook of Pharmaceutical Salts: Properties, and Use,* 2002.
He et al., *J. Biol. Chem.,* 270: 23258-23262, 1995.
He et al., *J. Biol. Chem.,* 271: 11641-11645, 1996.
Hirosumi et al., *Nature,* 420: 333-336, 2002.
Hof et al., *Cell,* 92: 441-450, 1998.
Ji et al., *eLife,* 6: e22513, 2017.
Keilhack et al., Diverse biochemical properties of Shp2 mutants. Implications for disease phenotypes. J Biol Chem 280:30984-30993, 2005.
Keller et al., *Anal. Chem.,* 84: 5066-5073, 2012.
Krenz M, et al., Role of ERK1/2 signaling in congenital valve malformations in Noonan syndrome. Proc Natl Acad Sci USA 105:18930-18935, 2008.
Lasic D D, Liposomes from physics to applications, Elsevier Science Publishers BV, Amsterdam, 1993.
Liamis et al., *World J Clin Cases,* 2(20):488-496, 2014.
Limal J M, et al., Noonan syndrome: Relationships between genotype, growth, and growth factors. J Clin Endocrinol Metab 91:300-306, 2006.
Longo et al., *Hum. Mol. Genet.,* 11(12): 1465-75, 2002.
Minor, et al., *Acta Crystallogr. D Biol. Crystallogr.* 62, 859-866, 2006.
McCoy, *Acta Crystallogr. D Biol. Crystallogr.* 63, 32-41, 2007.
Smith, *March's Advanced Organic Chemistry: Reactions, Mechanisms, and Structure, 7th edition* 2013.
Nakamura, et al., Mediating ERK 1/2 signaling rescues congenital heart defects in a mouse model of Noonan syndrome. J Clin Invest 117:2123-2132, 2007.
Nakamura et al., Noonan syndrome is associated with enhanced pERK activity, the repression of which can prevent craniofacial malformations. Proc Natl Acad Sci USA 106:15436-15441, 2009.
New RRC, Liposomes: A practical approach, IRL Press, Oxford, pages 33-104, 1990.
Nicolau et al., *Methods Enzymol,* 149:157-76, 1987.
Lasic D D, Liposomes from physics to applications, Elsevier Science Publishers BV, Amsterdam, 1993.
Perales et al., *Eur J. Biochem.,* 226(2): 255-66, 1994.
Perales et al., *Proc. Natl. Acad. Sci. U.S.A.,* 91(9):4086-90, 1994.
Anderson, *Practical Process Research & Development—A Guide for Organic Chemists* (2012)
Samuel and Shulman, *Cell,* 148: 852-871, 2012.
Sheen et al., *J. Pharm Sci.,* 80(7):712-14 1991.
Soutschek et al., *Nature,* 432(7014):173-8, 2004.
Taniguchi et al., *Nat. Rev. Mol. Cell Biol.,* 7: 85-96, 2006.
Traub et al., *Nat. Rev. Mol. Cell Biol,* 10: 583-596, 2009.
Wadhwa et al., 2004.
Wagner et al., *Proc. Nat. Acad. Sci. U.S.A.,* 87(9):3410-3414, 1990.
Wang et al., Inhibition of SHP2 ameliorates the pathogenesis of systemic lupus erythematosus. J Clin Invest. 126(6): 2077-2092, 2016.
Wenz, *Agnew. Chem. Int. Ed. Engl.,* 33:803-822 (1994).
White et al., *Cell,* 54: 641-649, 1988.
White et al., *Curr Top Microbiol Immunol.,* 228:179-208, 1998.
White, *Science,* 302:1710-1711, 2003.
Wilcox, C. S. *Semin Nephrol.,* 19(6):557-68, 1999.
Wolf et al., *J. Biol. Chem.,* 270: 27407-27410, 1995.
Wu and Wu, *J. Biol. Chem.,* 262:4429-4432, 1987.
Yoneyama et al., *Mol. Cell. Biol.,* 33: 1991-2003, 2013.
Zhou et al., Modular degradable dendrimers enable small RNAs to extend survival in an aggressive liver cancer model, 113:520-525, 2016.

What is claimed is:

1. A method of treating a disease in a mammalian subject comprising administering a therapeutically effective amount of a compound to the subject;
wherein the disease is Rabson-Mendenhall syndrome, insulin resistance, Donohue syndrome or Leprechaunism, or type II diabetes, and
wherein the compound has the structure:

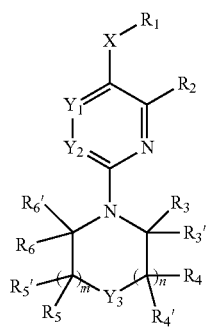

(I)

wherein:
$R_1$ is cycloakyl$_{(C3-12)}$, cycloalkenyl$_{(C5-12)}$, aryl$_{(C6-12)}$, heteroaryl$_{(C3-12)}$, heterocycloalkyl$_{(C3-12)}$, or a substituted version of any of these groups;
X is a covalent bond, O, NR$_{10}$, S(O)$_p$, C(O), COR$_{11}$, CR$_{10}$R$_{10}$'; wherein:
p is 0, 1, or 2;
$R_{10}$ and $R_{10}$' are each independently hydrogen, halo, alkyl$_{(C1-6)}$, or substituted alkyl$_{(C1-6)}$;
$R_{11}$ is alkanediyl$_{(C1-6)}$ or substituted alkanediyl$_{(C1-6)}$;
$Y_1$ and $Y_2$ are each independently N or CR$_9$, wherein:
$R_9$ is hydrogen, amino, cyano, halo, hydroxy, alkyl$_{(C1-6)}$, substituted alkyl$_{(C1-6)}$, alkoxy$_{(C1-6)}$, substituted alkoxy$_{(C1-6)}$, amido$_{(C1-6)}$, substituted amido$_{(C1-6)}$, acyl$_{(C1-6)}$, substituted acyl$_{(C1-6)}$, thioacyl$_{(C1-6)}$, substituted thioacyl$_{(C1-6)}$, alkylsulfinyl$_{(C1-6)}$, substituted alkylsulfinyl$_{(C1-6)}$, alkylsulfonyl$_{(C1-6)}$, substituted alkylsulfonyl$_{(C1-6)}$, —C(X$_1$)R$_a$, or —NR$_b$C(X$_2$)R$_c$, wherein:
X$_1$ and X$_2$ are each independently O, S, or NR$_d$, wherein R$_d$ is hydrogen, alkyl$_{(C1-6)}$, or substituted alkyl$_{(C1-6)}$; and
R$_a$ and R$_c$, are each independently alkyl$_{(C1-6)}$, substituted alkyl$_{(C1-6)}$, alkoxy$_{(C1-6)}$, substituted alkoxy$_{(C1-6)}$, alkylamino$_{(C1-6)}$, substituted alkylamino$_{(C1-6)}$, dialkylamino$_{(C2-6)}$, substituted dialkylamino$_{(C2-6)}$; and R$_b$ is hydrogen, alkyl$_{(C1-6)}$, or substituted alkyl$_{(C1-6)}$;

R$_2$ is amino, alkylamino$_{(C1-8)}$, substituted alkylamino$_{(C1-8)}$, dialkylamino$_{(C2-8)}$, or substituted dialkylamino$_{(C2-8)}$;

R$_3$, R$_3$', R$_4$, R$_4$', R$_5$, R$_5$', R$_6$, or R$_6$' are each independently hydrogen, amino, halo, hydroxy, alkyl$_{(C1-6)}$, substituted alkyl$_{(C1-6)}$, cycloalkyl$_{(C3-6)}$, substituted cycloalkyl$_{(C3-6)}$, alkoxy$_{(C1-6)}$, substituted alkoxy$_{(C1-6)}$, alkylamino$_{(C1-6)}$, substituted alkylamino$_{(C1-6)}$, dialkylamino$_{(C2-6)}$, or substituted dialkylamino$_{(C2-6)}$; or R$_3$ and R$_3$', R$_4$ and R$_4$', R$_5$ and R$_5$' or R$_6$ and R$_6$' are taken together and are oxo; or any two of R$_3$, R$_3$', R$_4$, R$_4$', R$_5$, R$_5$', R$_6$, R$_6$', and R$_7$ are taken together and form a cycloalkane$_{(C3-12)}$, cycloalkene$_{(C5-12)}$, arene$_{(C6-12)}$, heteroarene$_{(C3-12)}$, heterocycloalkane$_{(C3-12)}$, or a substituted version of any of these groups;

m and n is 0, 1, or 2; and

Y$_3$ is N or CR$_7$R$_8$, wherein:

R$_7$ and R$_8$ are each independently hydrogen, amino, or alkyl$_{(C1-12)}$, cycloalkyl$_{(C3-12)}$, aryl$_{(C6-12)}$, heteroaryl$_{(C3-12)}$, alkylamino$_{(C1-12)}$, dialkylamino$_{(C2-12)}$, or a substituted version of any of these groups; or R$_7$ and R$_8$ are taken together and form a cycloalkane$_{(C1-12)}$, cycloalkene$_{(C3-12)}$, arene$_{(C6-12)}$, heteroarene$_{(C3-12)}$, heterocycloalkane$_{(C3-12)}$, or a substituted version of any of these groups; or R$_7$ and R$_8$ are taken together and for a heterocycloalkane$_{(C3-12)}$ or a substituted heterocycloalkane$_{(C3-12)}$ which is further optionally substituted with an oxo group, an acyloxy$_{(C1-8)}$ group, or a substituted acyloxy$_{(C2-8)}$ group;

or a pharmaceutically acceptable salt thereof.

2. The method of claim 1, wherein the compound has the structure:

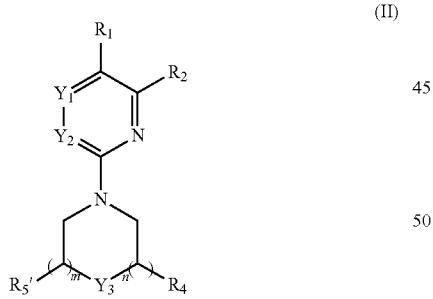

(II)

wherein:

R$_1$ is cycloakyl$_{(C3-12)}$, cycloalkenyl$_{(C5-12)}$, aryl$_{(C6-12)}$, heteroaryl$_{(C3-12)}$, heterocycloalkyl$_{(C3-12)}$, or a substituted version of any of these groups;

Y$_1$ and Y$_2$ are each independently N or CR$_9$, wherein:

R$_9$ is hydrogen, amino, cyano, halo, hydroxy, alkyl$_{(C1-6)}$, substituted alkyl$_{(C1-6)}$, alkoxy$_{(C1-6)}$, substituted alkoxy$_{(C1-6)}$, amido$_{(C1-6)}$, substituted amido$_{(C2-6)}$, acyl$_{(C1-6)}$, substituted acyl$_{(C1-6)}$, thioacyl$_{(C1-6)}$, substituted thioacyl$_{(C1-6)}$, alkylsulfinyl$_{(C1-6)}$, substituted alkylsulfinyl$_{(C1-6)}$, alkylsulfonyl$_{(C1-6)}$, substituted alkylsulfonyl$_{(C1-6)}$, —C(X$_1$)R$_a$, or —NR$_b$C(X$_2$)R$_c$, wherein:

X$_1$ and X$_2$ are each independently O, S, or NR$_d$, wherein R$_d$ is hydrogen, alkyl$_{(C1-6)}$, or substituted alkyl$_{(C1-6)}$; and R$_a$ and R$_c$ are each independently alkyl$_{(C1-6)}$, substituted alkyl$_{(C1-6)}$, alkoxy$_{(C1-6)}$, substituted alkoxy$_{(C1-6)}$, alkylamino$_{(C1-6)}$, substituted alkylamino$_{(C1-6)}$, dialkylamino$_{(C2-6)}$, substituted dialkylamino$_{(C2-6)}$; and R$_b$ is hydrogen, alkyl$_{(C1-6)}$, or substituted alkyl$_{(C1-6)}$;

R$_2$ is amino, alkylamino$_{(C1-8)}$, substituted alkylamino$_{(C1-8)}$, dialkylamino$_{(C2-8)}$, or substituted dialkylamino$_{(C2-8)}$;

R$_4$ or R$_5$ are each independently hydrogen, amino, halo, hydroxy, alkyl$_{(C1-6)}$, substituted alkyl$_{(C1-6)}$, cycloalkyl$_{(C3-6)}$, substituted cycloalkyl$_{(C3-6)}$, alkoxy$_{(C1-6)}$, substituted alkoxy$_{(C1-6)}$, alkylamino$_{(C1-6)}$, substituted alkylamino$_{(C1-6)}$, dialkylamino$_{(C2-6)}$, or substituted dialkylamino$_{(C2-6)}$; or m and n is 0, 1, or 2; and Y$_3$ is N or CR$_7$R$_8$, wherein:

R$_7$ and R$_8$ are each independently hydrogen, amino, or alkyl$_{(C1-12)}$, cycloalkyl$_{(C3-12)}$, aryl$_{(C6-12)}$, heteroaryl$_{(C3-12)}$, alkylamino$_{(C1-12)}$, dialkylamino$_{(C2-12)}$, or a substituted version of any of these groups; or R$_7$ and R$_8$ are taken together and form a cycloalkane$_{(C3-12)}$, cycloalkene$_{(C5-12)}$, arene$_{(C6-12)}$, heteroarene$_{(C3-12)}$, heterocycloalkane$_{(C3-12)}$, or a substituted version of any of these groups;

or a pharmaceutically acceptable salt thereof.

3. The method of claim 2, wherein the compound has the structure:

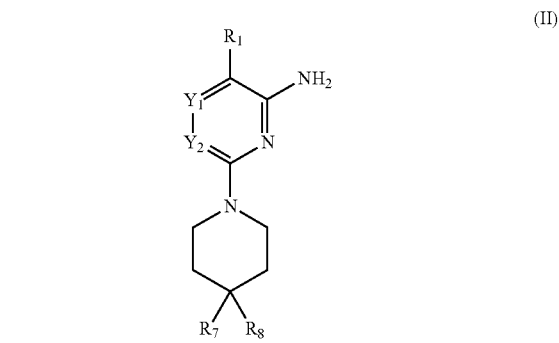

(II)

wherein:

R$_1$ is cycloakyl$_{(C3-12)}$, cycloalkenyl$_{(C5-12)}$, aryl$_{(C6-12)}$, heteroaryl$_{(C3-12)}$, heterocycloalkyl$_{(C3-12)}$, or a substituted version of any of these groups;

Y$_1$ and Y$_2$ are each independently N or CR$_9$, wherein:

R$_9$ is hydrogen, amino, cyano, halo, hydroxy, alkyl$_{(C1-6)}$, substituted alkyl$_{(C1-6)}$, alkoxy$_{(C1-6)}$, substituted alkoxy$_{(C1-6)}$, amido$_{(C1-6)}$, substituted amido$_{(C1-6)}$, acyl$_{(C1-6)}$, substituted acyl$_{(C1-6)}$, thioacyl$_{(C1-6)}$, substituted thioacyl$_{(C1-6)}$, alkylsulfinyl$_{(C1-6)}$, substituted alkylsulfinyl$_{(C1-6)}$, alkylsulfonyl$_{(C1-6)}$, substituted alkylsulfonyl$_{(C1-6)}$, —C(X$_1$)R$_a$, or —NR$_b$C(X$_2$)R$_c$, wherein:

X$_1$ and X$_2$ are each independently O, S, or NR$_d$, wherein R$_d$ is hydrogen, alkyl$_{(C1-6)}$, or substituted alkyl$_{(C1-6)}$; and $R_a$ and $R_c$ are each independently alkyl$_{(C1-6)}$, substituted alkyl$_{(C1-6)}$, alkoxy$_{(C1-6)}$, substituted alkoxy$_{(C1-6)}$, alkylamino$_{(C1-6)}$, substituted alkylamino$_{(C1-6)}$, dialkylamino$_{(C2-6)}$, substituted dialkylamino$_{(C2-6)}$; and $R_b$ is hydrogen, alkyl$_{(C1-6)}$, or substituted alkyl$_{(C1-6)}$; and $R_7$ and $R_8$ are each independently hydrogen, amino, or alkyl$_{(C1-12)}$, cycloalkyl$_{(C3-12)}$, aryl$_{(C6-12)}$, heteroaryl$_{(C3-12)}$, alkylamino$_{(C1-12)}$, dialkylamino$_{(C2-12)}$, or a substituted version of any of these groups; or $R_7$ and $R_8$ are taken together and form a cycloalkane$_{(C3-12)}$, cycloalkene$_{(C5-12)}$, arene$_{(C6-12)}$, heteroarene$_{(C3-12)}$, heterocycloalkane$_{(C3-12)}$, or a substituted version of any of these groups;

or a pharmaceutically acceptable salt thereof.

4. The method of claim 3, wherein the compound has the structure:

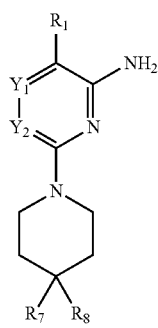

(II)

wherein:

$R_1$ is aryl$_{(C6-12)}$ or substituted aryl$_{(C6-12)}$;

$Y_1$ and $Y_2$ are each independently N or $CR_9$, wherein:
$R_9$ is hydrogen, amino, alkyl$_{(C1-6)}$, substituted alkyl$_{(C1-6)}$, alkoxy$_{(C1-6)}$, substituted alkoxy$_{(C1-6)}$, amido$_{(C1-6)}$, substituted amido $_{(C1-6)}$, acyl$_{(C1-6)}$, or substituted acyl$_{(C1-6)}$;

$R_7$ is hydrogen or alkyl$_{(C1-12)}$, cycloalkyl$_{(C3-12)}$, aryl$_{(C6-12)}$, heteroaryl$_{(C3-12)}$, or a substituted version of any of these groups; and $R_8$ is amino, substituted alkyl$_{(C1-12)}$, alkylamino$_{(C1-12)}$, substituted alkylamino$_{(C1-12)}$, dialkylamino$_{(C2-12)}$, or substituted dialkylamino$_{(C2-12)}$;

or a pharmaceutically acceptable salt thereof.

5. The method of claim 1, wherein $R_1$ is substituted aryl$_{(C6-12)}$.

6. The method of claim 5, wherein $R_1$ is dichlorophenyl.

7. The method of claim 6, wherein $R_1$ is 2,3-dichlorophenyl.

8. The method of claim 1, wherein $Y_1$ is N.

9. The method of claim 1, wherein $Y_2$ is CH.

10. The method of claim 1, wherein $R_7$ is alkyl$_{(C1-12)}$ or substituted alkyl$_{(C1-12)}$.

11. The method of claim 10, wherein $R_7$ is alkyl$_{(C1-6)}$.

12. The method of claim 11, wherein $R_7$ is methyl.

13. The method of claim 1, wherein $R_8$ is amino, aminomethyl, or methylamino.

14. The method of claim 1, wherein $R_8$ is amino.

15. The method of claim 1, wherein the compound is a compound in Table 1.

16. The method of claim 15, wherein the compound is:

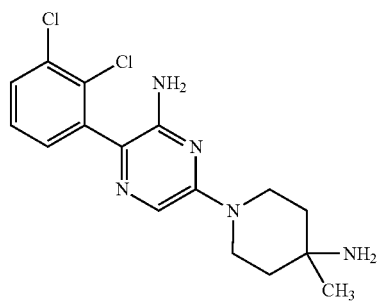 [SMILES: CC1(N)CCN(c2cnc(-c3cccc(Cl)c3Cl)c(N)n2)CC1]

or a pharmaceutically acceptable salt thereof.

17. The method of claim 1, wherein the subject is a human.

18. The method of claim 1, wherein the subject has an insulin receptor disease (IR).

19. The method of claim 1, wherein the subject has type II diabetes.

20. The method of claim 1, wherein the subject has a familial or genetic form of diabetes.

21. The method of claim 20, wherein the subject has Leprechaunism or Rabson-Mendenhall syndrome.

22. The method of claim 18, wherein the subject has a mutation in or affecting the insulin receptor (IR).

23. The method of claim 22, wherein the subject is a human and has a P997T, V1012M, A1055V, K1095E, R1119Q, H1157R, R1191Q, Y1361C, R1378Q, R1020Q, V1054M, A1075D, V1086E, I1143T, A1162E, or W1220L mutation in the insulin receptor.

24. The method of claim 1, wherein a second compound is administered to the subject to treat diabetes.

25. The method of claim 24, wherein the second compound is metformin, a sulfonylurea, a meglitinide, a thiazolidinedione, a DPP-4 inhibitor, a GLP-1 receptor agonist, a SGLT2 inhibitor, or insulin.

* * * * *

UNITED STATES PATENT AND TRADEMARK OFFICE
CERTIFICATE OF CORRECTION

| | | |
|---|---|---|
| PATENT NO. | : 11,426,422 B2 | Page 1 of 1 |
| APPLICATION NO. | : 16/261819 | |
| DATED | : August 30, 2022 | |
| INVENTOR(S) | : Yu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 17 days.

Signed and Sealed this
Fourteenth Day of January, 2025

Derrick Brent
*Acting Director of the United States Patent and Trademark Office*